(12) United States Patent
Hussain et al.

(10) Patent No.: US 9,944,633 B2
(45) Date of Patent: *Apr. 17, 2018

(54) COMPOUNDS AND METHODS FOR THE TREATMENT OF ISOCITRATE DEHYDROGENASE RELATED DISEASES

(71) Applicants: THE BROAD INSTITUTE, INC., Cambridge, MA (US); PRESIDENT & FELLOWS OF HARVARD COLLEGE, Cambridge, MA (US)

(72) Inventors: Mahmud Hussain, Dhaka (BD); Daisuke Ito, Ibaraki (JP); Jason Law, Cambridge, MA (US); Matthias Leiendecker, Trier (DE); Ke Liu, Cambridge, MA (US); Benito Munoz, Newtonville, MA (US); Stuart Schreiber, Boston, MA (US); Alykhan Shamji, Somerville, MA (US); Andrew Stern, Boston, MA (US)

(73) Assignees: The Broad Institute, Inc., Cambridge, MA (US); PRESIDENT & FELLOWS OF HARVARD COLLEGE, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/818,009

(22) Filed: Aug. 4, 2015

(65) Prior Publication Data
US 2016/0102087 A1 Apr. 14, 2016

Related U.S. Application Data

(63) Continuation of application No. 14/037,761, which is a continuation of application No. PCT/US2012/031245, filed on Mar. 29, 2012, now Pat. No. 9,120,810.

(60) Provisional application No. 61/469,054, filed on Mar. 29, 2011.

(51) Int. Cl.
| | |
|---|---|
| *C07D 419/12* | (2006.01) |
| *C07D 413/12* | (2006.01) |
| *C07D 413/14* | (2006.01) |
| *C07D 417/12* | (2006.01) |
| *C07D 417/14* | (2006.01) |
| *C07D 498/04* | (2006.01) |

(52) U.S. Cl.
CPC ......... *C07D 419/12* (2013.01); *C07D 413/12* (2013.01); *C07D 413/14* (2013.01); *C07D 417/12* (2013.01); *C07D 417/14* (2013.01); *C07D 498/04* (2013.01)

(58) Field of Classification Search
None
See application file for complete search history.

(56) References Cited

U.S. PATENT DOCUMENTS 9,120,810 B2 * 9/2015 Hussain ............... C07D 413/12

* cited by examiner

*Primary Examiner* — Noble E Jarrell
(74) *Attorney, Agent, or Firm* — Elmore Patent Law Group, P.C.; Mahreen Hoda; Carolyn Elmore

(57) ABSTRACT

The invention relates to compounds of Formula I or a pharmaceutically acceptable salt, ester or prodrug thereof:

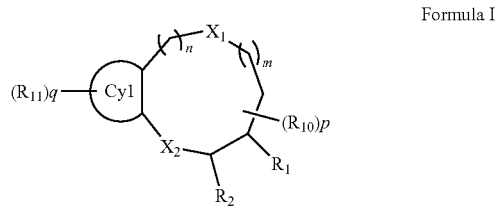

Formula I

30 Claims, 5 Drawing Sheets

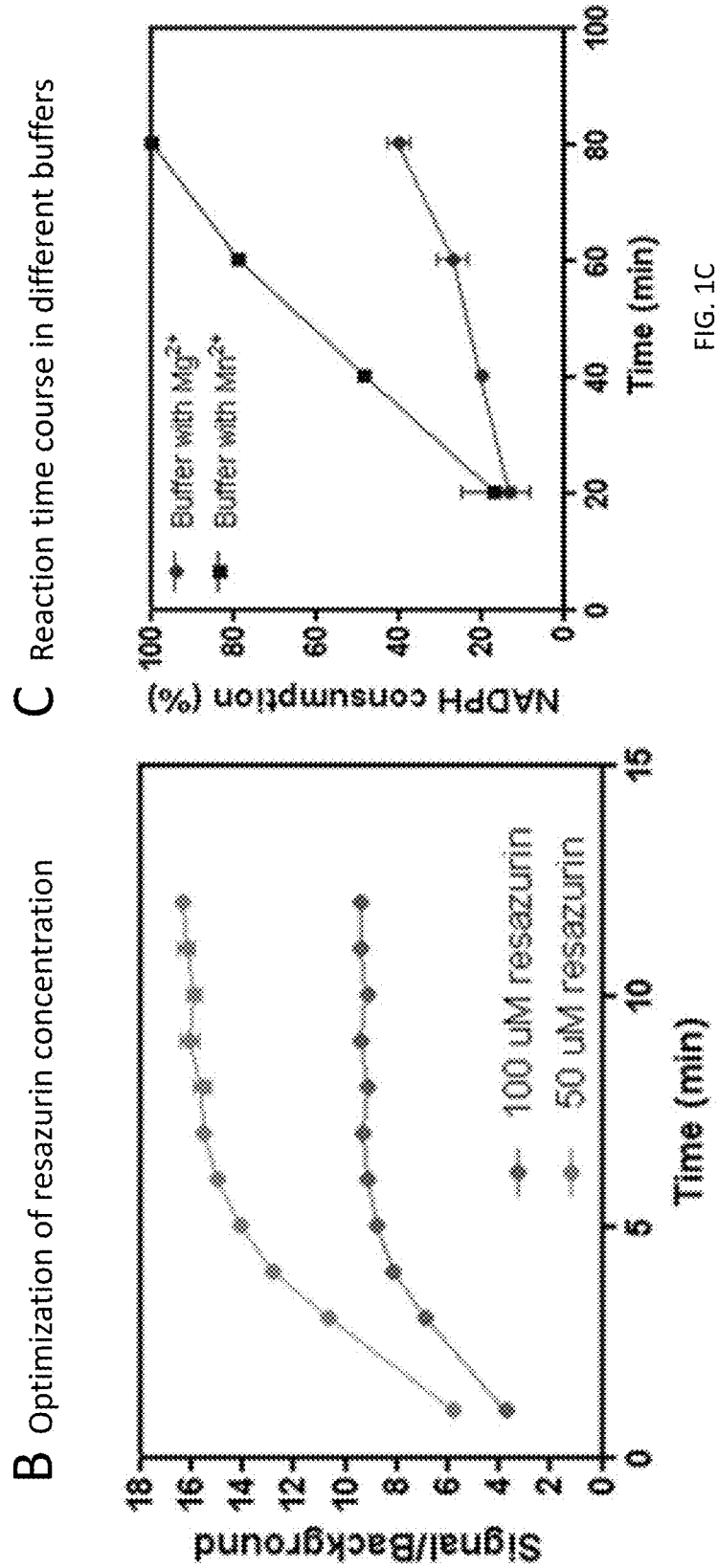

COMPOUNDS AND METHODS FOR THE TREATMENT OF ISOCITRATE DEHYDROGENASE RELATED DISEASES

RELATED APPLICATIONS

This application is a continuation of U.S. application Ser. No. 14/037,761, filed on Sep. 26, 2013, which is a continuation of International Application No. PCT/US2012/031245, which designated the United States and was filed on Mar. 29, 2012, published in English, which claims the benefit of U.S. Provisional Application No. 61/469,054, filed on Mar. 29, 2011. The entire teachings of the above applications are incorporated herein by reference.

GOVERNMENT SUPPORT

This invention was made with government support under Grant No. CA148399 awarded by the National Institutes of Health. The government has certain rights in the invention.

BACKGROUND

Cancer genomics is revealing comprehensively somatic mutations that may constitute the root cause of disease. These findings suggest novel mechanisms for cancer initiation and progression, and new ways we might treat cancer in the future. Recently, a genome-wide sequencing study identified mutations in the metabolic enzyme IDH1 in samples from patients with glioblastoma multiforms, which are among the most lethal cancers with survival of only months after their diagnosis. (Parsons D. W. et al., Science 321, 1807-1812, 2008). Subsequent analyses revealed that mutations in IDH1 are common (70%-80%) in grade II, III gliomas and secondary glioblastomas and that patients lacking IDH1 mutations often harbor mutations in IDH2, which shares 70% identity with IDH1. (Yan H. et al., N Engl J Med 360, 765-773, 2009; Bleeker F. E. et al., Hum Mutat 30, 7-11, 2009; Balss J. et al., Acta Neuropathol 116, 597-602, 2008). More recently, IDH1/2 mutations have been observed in acute myeloid leukemia (AML) and rare cases have been reported in other cancers. (Ward P. S. et al., Cancer Cell 17, 225-234, 2010; Exp. Med. 207, 339-344, 2010; Mardis E. R. et al., N Engl J Med 361, 1058-1066, 2009). Notably, all mutations in IDH1/2 are heterozygous and the majority of them affect a particular codon (R132 in IDH1 and the analogous codon, R172, in IDH2) suggesting the gene may contribute to carcinogenesis as an oncogene rather than a tumor suppressor through a gain of function.

IDH1/2 are NADP+-dependent isocitrate dehydrogenases that normally mediate oxidative decarboxylation of isocitrate to α-ketoglutarate (α-KG) via the conversion of NADP+ to NADPH. Mutations in IDH1/2 appear to have two functional consequences for the enzymes' activities: i) a decreased ability to convert isocitrate to α-KG; and ii) a new ability to reduce α-KG to (R)-2-hydroxyglutarate (2-HG) using NADPH (Ward et al., supra; Dang, L. et al., Nature 462, 739-744, 2009). Indeed 2-HG levels are elevated >50-fold in samples from patients with IDH1/2-mutations. This observation has motivated study of 2-HG as a disease biomarker, as well as deeper study into the molecular mechanism by which this putative 'oncometabolite' might contribute to disease. Indeed, 2-HG could interfere with a wide range of processes, such as those regulated by α-KG-dependent, iron-dependent dioxygenases; these processes include the response to hypoxic stress (mediated by EglN prolyl hydroxylases), DNA modification (mediated by TET2, a 5-methylcytosine hydroxylase), and histone methylation (mediated by JmjC-containing demethylases), among others (Figueroa M. E. et al., Cancer Cell, 18, 553-567, 2010; Christensen, B. C. et al., J. Natl. Cancer Inst. 103, 2, 143-53, 2011; Zhao, S. et al., Science, 324, 261-265, 2009; Xu, W. et al., Cancer Cell, 19, 17-30, 2011). Thus, the development of small molecules that inhibit the 2-HG-generating activity of IDH1/2 mutants in cells is important in cancer cell biology and drug development.

Point mutations IDH1 and IDH2 occur early in the pathogenesis of gliomas. Reitman reports that the study of 200 metabolites in human oligodendroglioma (HOG) cells to determine the effects of expression of IDH1 and IDH2 mutants showed that the levels of amino acids, glutathione metabolites, choline derivatives, and tricarboxylic acid (TCA) cycle intermediates were altered in mutant IDH1- and IDH2-expressing cells. (Reitman Z. J. et al., Proc. Natl. Acad. Sci. 2011, 108(8) 3270-3275). Furthermore, N-acetyl-aspartyl-glutamate (NAAG), a common dipeptide in brain, was 50-fold reduced in cells expressing IDH1 mutants and 8.3-fold reduced in cells expressing IDH2 mutants.

Hartmann et al., (US 20100291590) discloses a method for the diagnosis of a brain tumor using the presence/absence of a particular IDH1 mutation as a marker. Vogelstein et al. (WO 2010/028099) discloses that mutations in IDH1 and IDH2 are related to astrocytomas, oligodendrogliomas and glioblastomas. Dang et al., (WO 2010/105243) discloses methods for the treatment of isocitrate dehydrogenase related proliferative disorders.

Glioblastoma is the most frequent and most malignant human brain tumor. The prognosis remains very poor, with most patients dying within 1 year after diagnosis. (Ohgaki et al. *American Journal of Pathology,* 170(5), 2007, 1445-1453). There exists a need to develop effective treatments against proliferative disorders including glioblastoma and acute myeloid leukemia. Thus, there exists a need to focus on developing compounds that inhibit mutated IDH1/2 with selectivity over wild-type IDH1/2 with the goal of targeting cancer cells selectively over normal cell. That said, there is also a need for advancing compounds that target both mutant and wild-type IDH1/2 since cancer cells which harbor mutant IDH alleles are dependent on the wild-type allele for proliferation, suggesting inhibition of wild-type IDH may also prove valuable for treating cancer (Ward P. S. et al., Cancer Cell 17, 225-234, 2010).

SUMMARY OF THE INVENTION

The invention relates to compounds of Formula I or a pharmaceutically acceptable salt, ester or prodrug thereof and their use in the manufacture of a medicament, in particular, for the treatment of a cell proliferative disease:

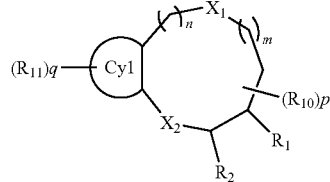

Formula I each n and m is independently 0, 1, 2 or 3;
each p and q is independently 0, 1, 2, 3, 4, 5, 6 or 7;

$X_1$ is —C(O)N($R_A$)—, —C(S)N($R_A$)—, or —S(O)$_2$N($R_A$)—;
  wherein $R_A$ is hydrogen, aliphatic, substituted aliphatic, heteroaryl, substituted heteroaryl, aryl or substituted aryl;

$X_2$ is —S—, —O—, —S(O)$_2$—, —C($R_{20}$)($R_{21}$)— or —N($R_B$)—;
  wherein $R_B$ is hydrogen, aliphatic, substituted aliphatic, heteroaryl, substituted heteroaryl, aryl or substituted aryl;

each $R_1$ and $R_2$ is independently hydrogen, halogen, aliphatic, substituted aliphatic, aryl or substituted aryl;

each $R_{10}$ is independently absent, hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$ groups together with the atoms to which they are attached and any intervening atoms may form an additional optionally substituted, 3, 4, 5, 6 or 7 membered ring;
  wherein each $R_{20}$ and $R_{21}$ is independently hydrogen, halogen, aliphatic, substituted aliphatic, aryl or substituted aryl;

each $R_{11}$ is independently absent, hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{11}$ groups together with the atoms to which they are attached and any intervening atoms may form an additional optionally substituted, 3, 4, 5, 6 or 7 membered ring; and, Cy1 is an optionally substituted aryl or optionally substituted heteroaryl.

The invention further relates to the use of a compound of Formula I in the manufacture of a medicament. The invention further relates to the use of a compound of Formula I for the treatment of a cell proliferative disease and the use of a compound of Formula I in the manufacture of a medicament for the treatment of a cell proliferative disease.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 (E): The effect of DMSO on the IDH1-R132H assay.

FIG. 1 (F): Reaction time course of the IDH1-R132H assay.

FIG. 1 (G): Concentration-response of the IDH1-R132H enzyme. The assay was linear at 8 μm/ml.

DETAILED DESCRIPTION OF THE INVENTION

Figure 1A:
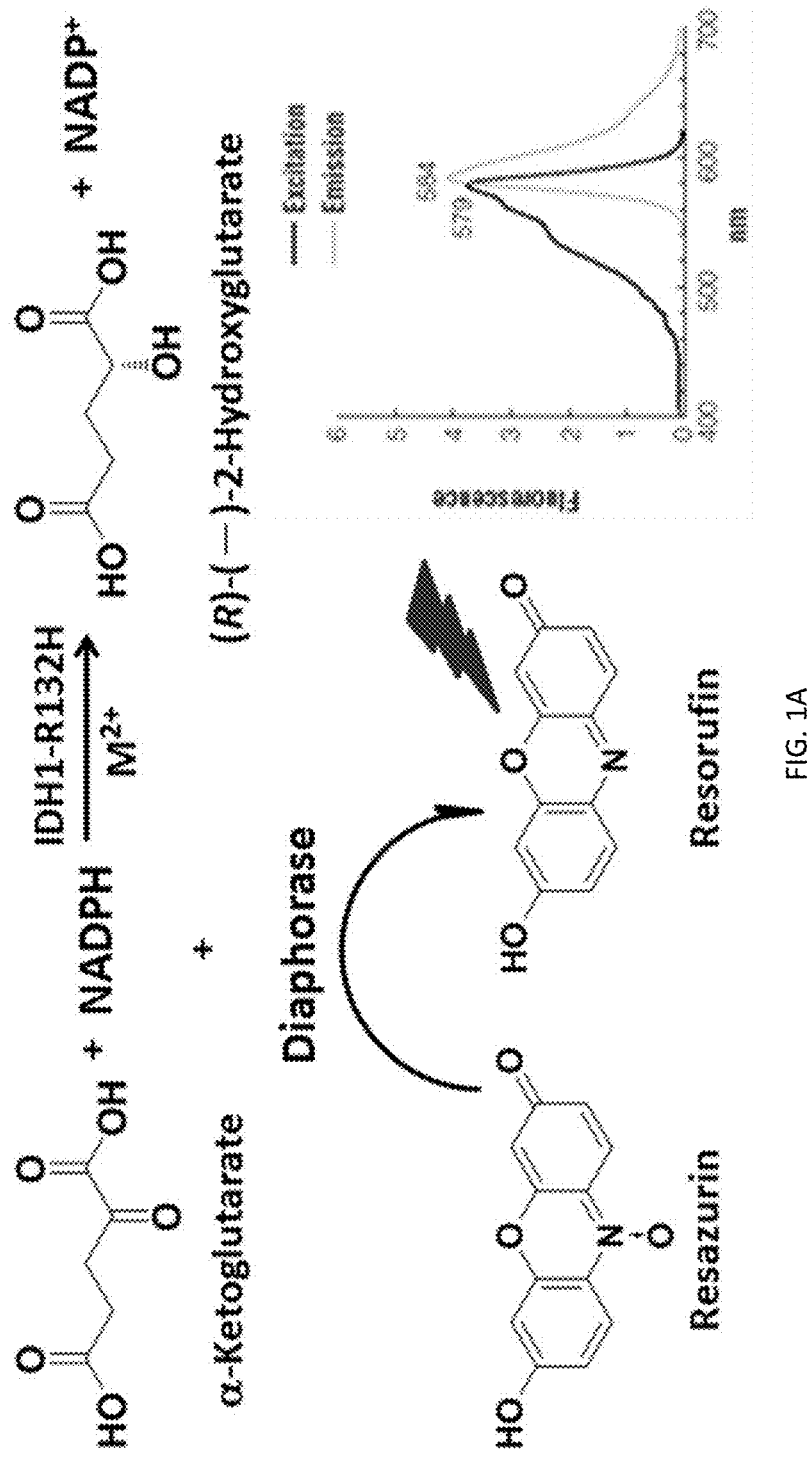
FIG. 1(A): Diagram of the assay principle for the IDH1-R132H enzymatic assay.
Figures 1D, 1E:
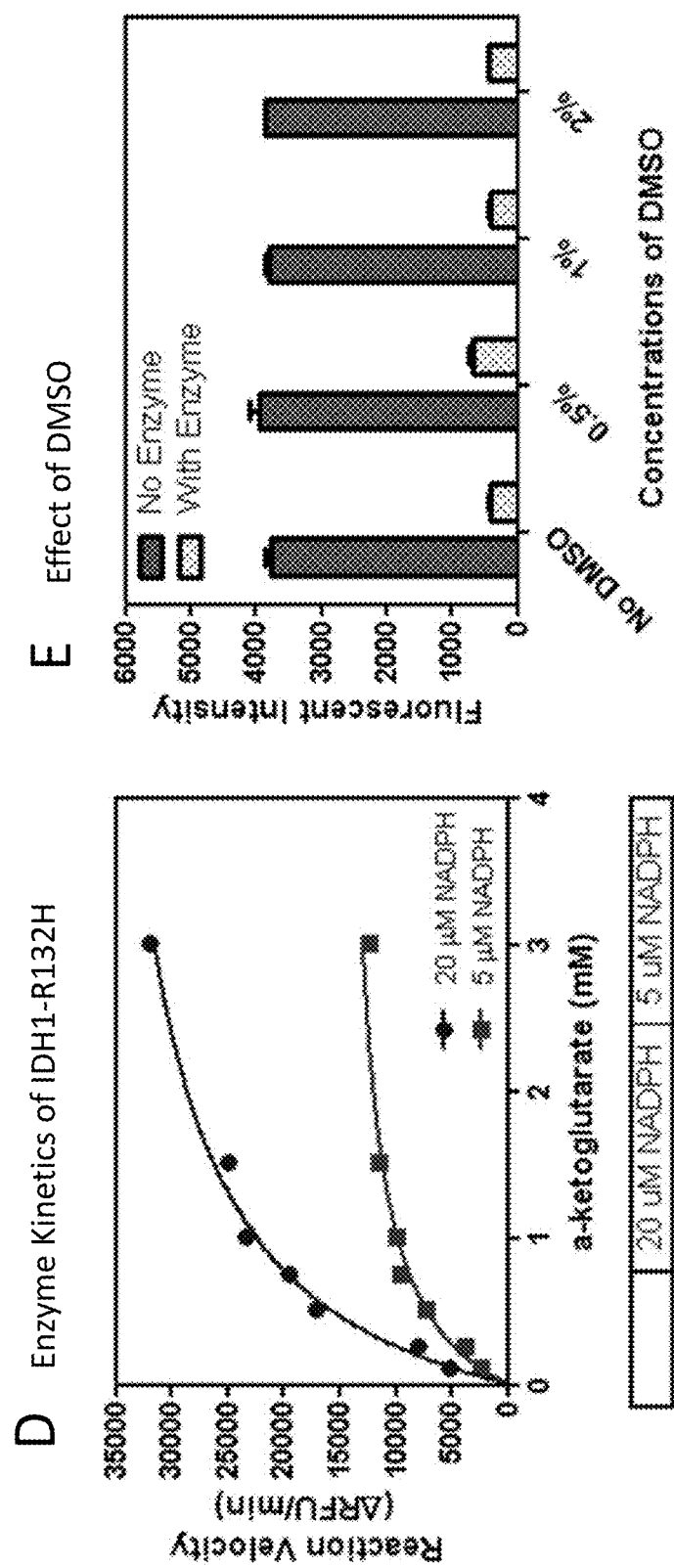
FIG. 1(B): Optimization of resazurin concentration to give the highest signal-to-background ratio.
FIG. 1(C): Reaction time course of the IDH1-R132H enzyme assay in buffers with magnesium or manganese.
FIG. 1 (D): Km of α-Ketoglutarate with 20 μM or 5 μM of NADPH.
Figures 1F, 1G:
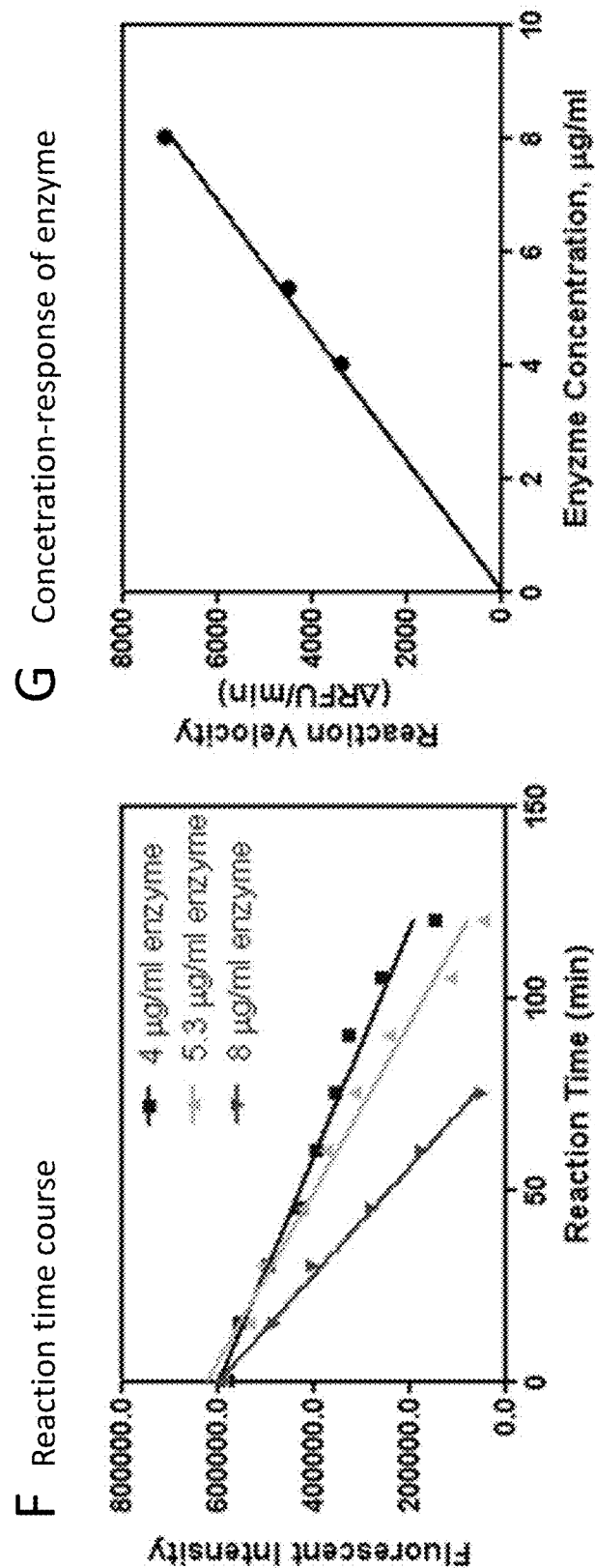

The invention relates to compounds of Formula I or a pharmaceutically acceptable salt, ester or prodrug thereof, and their use in the manufacture of a medicament, in particular, for the treatment of a cell proliferative disease:

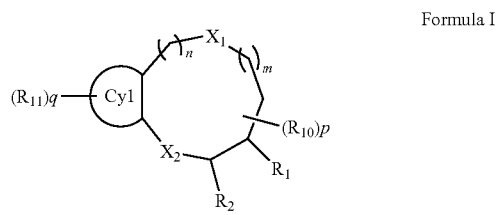

Formula I each n and m is independently 0, 1, 2 or 3;
each p and q is independently 0, 1, 2, 3, 4, 5, 6 or 7;
$X_1$ is —C(O)N($R_A$)—, —C(S)N($R_A$)—, or —S(O)$_2$N($R_A$)—;
  wherein $R_A$ is hydrogen, aliphatic, substituted aliphatic, heteroaryl, substituted heteroaryl, aryl or substituted aryl;

$X_2$ is —S—, —O—, —S(O)$_2$—, —C($R_{20}$)($R_{21}$)— or —N($R_B$)—;
  wherein $R_B$ is hydrogen, aliphatic, substituted aliphatic, heteroaryl, substituted heteroaryl, aryl or substituted aryl;

each $R_1$ and $R_2$ is independently hydrogen, halogen, aliphatic, substituted aliphatic, aryl or substituted aryl;

each $R_{10}$ is independently absent, hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{10}$ groups together with the atoms to which they are attached and any intervening atoms may form an additional optionally substituted, 3, 4, 5, 6 or 7 membered ring;
  wherein each $R_{20}$ and $R_{21}$ is independently hydrogen, halogen, aliphatic, substituted aliphatic, aryl or substituted aryl;

each $R_{11}$ is independently absent, hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two of $R_{11}$ groups together with the atoms to which they are attached and any intervening atoms may form an additional optionally substituted, 3, 4, 5, 6 or 7 membered ring; and, Cy1 is an optionally substituted aryl or optionally substituted heteroaryl.

In one embodiment, the invention relates to a compound of Formula II-III or a pharmaceutically acceptable salt, ester or prodrug thereof:

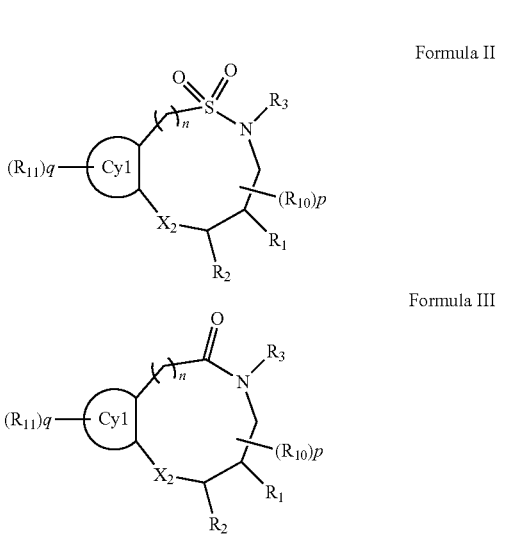

Formula II

Formula III wherein, n, p, q, $X_2$, Cy1, $R_1$, $R_2$, $R_{10}$, and $R_{11}$ are as defined above; and $R_3$ is hydrogen, halogen, aliphatic, substituted aliphatic, aryl or substituted aryl.

In a preferred embodiment, the invention relates to a compound of Formula IIIA:

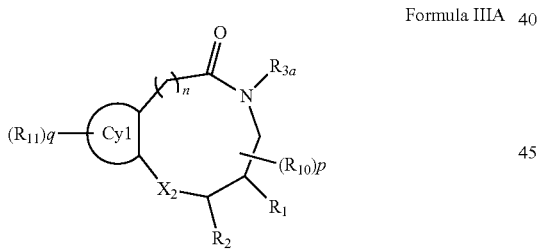

Formula IIIA wherein $R_3$a is selected from alkyl, aryl, alkyl substituted with aryl, straight chain or branched $C_1$-$C_{10}$ alkyl, $C_1$-$C_{10}$ alkenyl, $C_1$-$C_{10}$ alkynyl, $C_1$-$C_{10}$ alkoxy, alkoxy$C_1$-$C_{10}$alkoxy, $C_1$-$C_{10}$alkylamino, alkoxy$C_1$-$C_{10}$alkylamino, $C_1$-$C_{10}$ alkylcarbonylamino, $C_1$-$C_{10}$ alkylaminocarbonyl, aryloxy$C_1$-$C_{10}$ alkoxy, aryloxy$C_1$-$C_{10}$alkylamino, aryloxy$C_1$-$C_{10}$ alkylamino carbonyl, $C_1$-$C_{10}$-alkylaminoalkylaminocarbonyl, $C_1$-$C_{10}$alkyl(N-alkyl)aminoalkyl-aminocarbonyl, alkylaminoalkylamino, alkylcarbonylaminoalkylamino, alkyl(N-alkyl)aminoalkylamino, (N-alkyl)alkylcarbonylaminoalkylamino, alkylaminoalkyl, alkylaminoalkylaminoalkyl, alkylpiperazinoalkyl, piperazinoalkyl, alkylpiperazino, alkenylaryloxy$C_1$-$C_{10}$ alkoxy, alkenylarylamino$C_1$-$C_{10}$ alkoxy, alkenylaryllalkylamino $C_1$-$C_{10}$ alkoxy, alkenylaryloxy$C_1$-$C_{10}$ alkylamino, alkenylaryloxy$C_1$-$C_{10}$alkylaminocarbonyl, piperazinoalkylaryl, heteroaryl$C_1$-$C_{10}$ alkyl, heteroaryl$C_1$-$C_{10}$alkenyl, heteroaryl$C_1$-$C_{10}$ alkynyl, heteroaryl$C_1$-$C_{10}$ alkylamino, heteroaryl$C_1$-$C_{10}$alkoxy, heteroaryloxy$C_1$-$C_{10}$alkyl, heteroaryloxy$C_1$-$C_{10}$ alkenyl, heteroaryloxy$C_2$-$C_{10}$ alkynyl, heteroaryloxy$C_1$-$C_{10}$alkylamino, heteroaryloxy$C_1$-$C_{10}$ alkoxy.

In one embodiment, the invention relates to a compound of Formula IV-V or a pharmaceutically acceptable salt, ester or prodrug thereof:

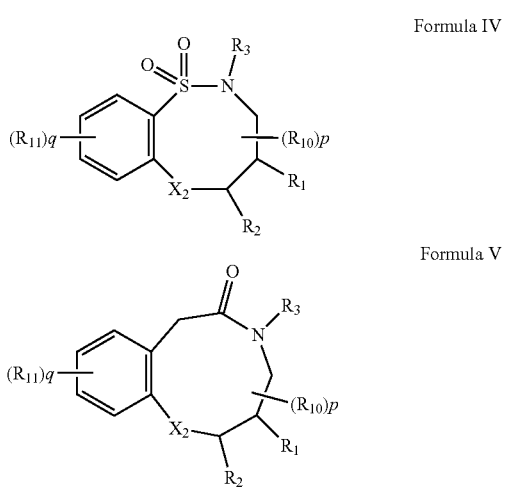

Formula IV

Formula V wherein p, q, $X_2$, $R_1$, $R_2$, $R_3$, $R_{10}$, and $R_{11}$ are as defined above.

In a preferred embodiment, the invention relates to a compound of Formula V wherein $R_3$ is $R_3$a, and $R_3$a is as defined above.

In a preferred embodiment, the invention relates to a compound of Formula I, II, III, IV or V wherein, $R_1$ is an optionally substituted alkyl. In a preferred embodiment, $R_1$ is an optionally substituted $C_1$-$C_6$ alkyl, more preferably selected from methyl, ethyl, propyl, cyclopropyl, isopropyl, n-butyl, tert-butyl, cyclobutyl, n-pentyl, neopentyl, cyclopentyl, n-hex yl and cyclohexyl.

In one embodiment, the invention relates to a compound of Formula I-III wherein Cy1 is selected from Table A:

TABLE A

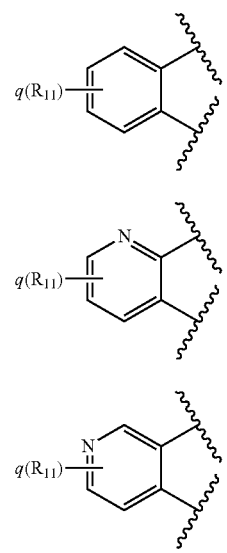

TABLE A-continued
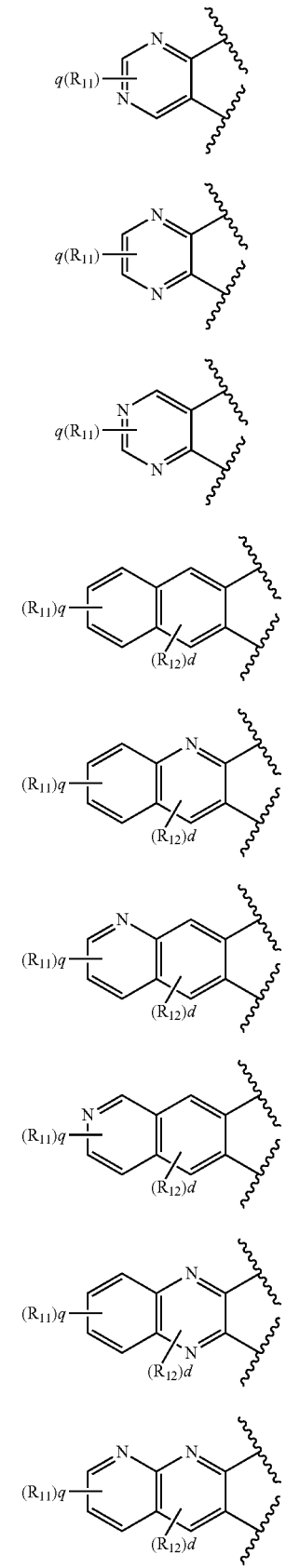
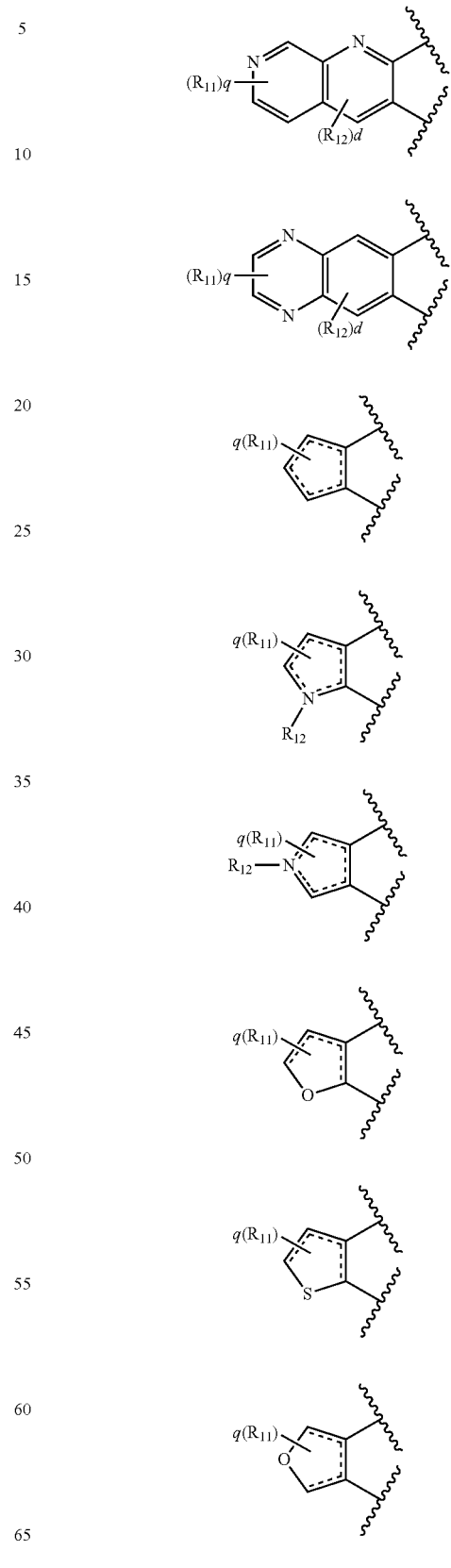

TABLE A-continued
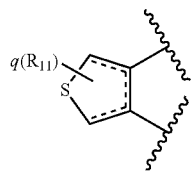
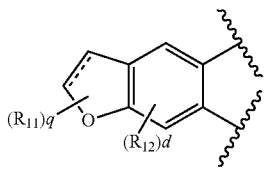
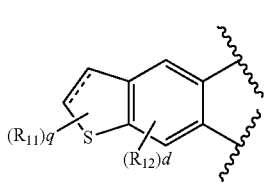
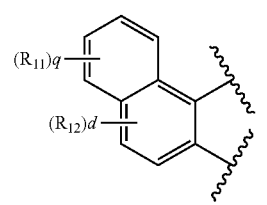
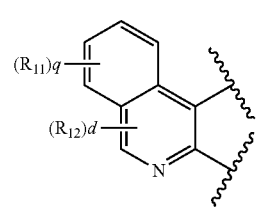
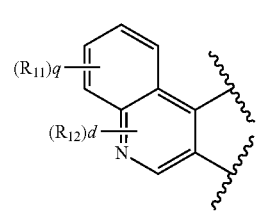
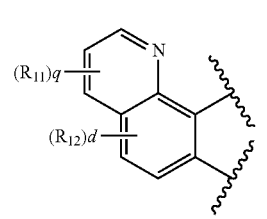
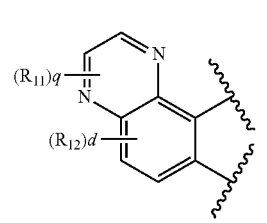
TABLE A-continued
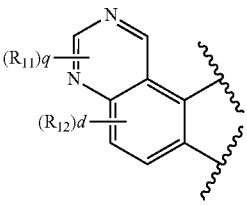
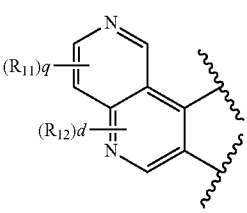
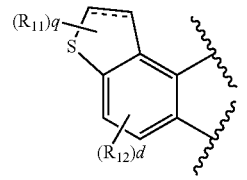
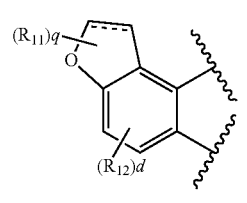
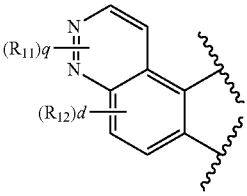
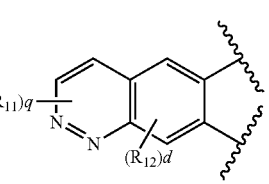
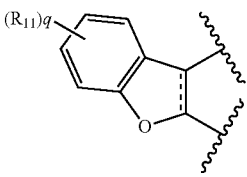
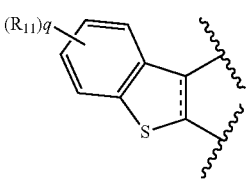
wherein ═══ represents a single or double bond;
each $R_{12}$ is independently absent, hydrogen, —C(O)$R_{20}$, —C(O)O$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl, substituted aryl, heteroaryl or substituted heteroaryl;

d is 0, 1 or 2;

alternatively, two $R_{11}$ and $R_{12}$ groups may form an optionally substituted 3, 4, 5, 6, or 7 membered ring.

In one embodiment the invention relates to a compound of Formula I-V and $R_{11}$ is selected from Table B:

TABLE B

| |
|---|
| $t(R_{13})$— cyclopentenyl |
| $t(R_{13})$— phenyl (dashed) |
| $t(R_{13})$— furan |
| $t(R_{13})$— furan (dashed) |
| $t(R_{13})$— pyridine (2-) |
| $t(R_{13})$— pyridine (3-) |
| $t(R_{13})$— pyridine (4-) |
| $t(R_{13})$— pyrimidine |
| $t(R_{13})$— pyrazine |
| $t(R_{13})$— pyrrole (dashed) |
| $t(R_{13})$— pyrrole N (dashed) |
| $t(R_{13})$— phenyl |

TABLE B-continued

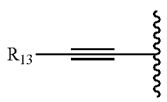

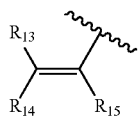

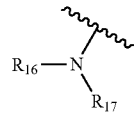

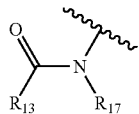

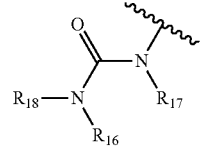

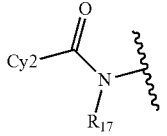

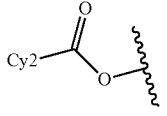

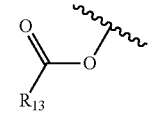

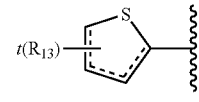

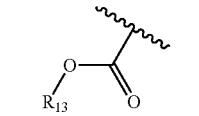

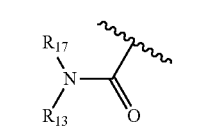

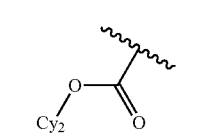

TABLE B-continued

TABLE B-continued

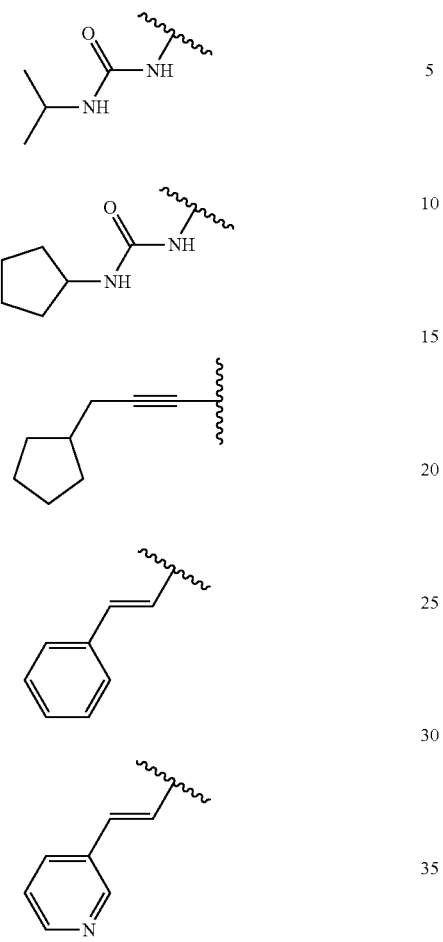

wherein, t is 0, 1, 2, 3, 4, 5, 6 or 7;

Cy2 is an optionally substituted cycloalkyl, optionally substituted cycloalkenyl, optionally substituted heterocyclyl, optionally substituted aryl or optionally substituted heteroaryl;

each $R_{13}$, $R_{14}$ and $R_{15}$ is independently absent, hydrogen, halogen, —$OR_{20}$, —$SR_{20}$, —$NR_{20}R_{21}$, —$CF_3$, —CN, —$NO_2$, —$N_3$, —$C(O)R_{20}$, —$C(O)OR_{20}$, —$C(O)NR_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl; alternatively two $R_{13}$ groups together with the atoms to which they are attached and any intervening atoms may form an additional optionally substituted, 3, 4, 5, 6 or 7 membered ring; and, each $R_{16}$, $R_{17}$ and $R_{18}$ is independently hydrogen, halogen, aliphatic, substituted aliphatic, aryl substituted aryl, heteroaryl or substituted heteroaryl;

alternatively two of $R_{13}$, $R_{14}$, $R_{15}$, $R_{16}$, $R_{17}$ and $R_{18}$ groups together with the atoms to which they are attached, and any intervening atoms may form an optionally substituted 3, 4, 5, 6 or 7 membered ring.

In one embodiment the invention relates to a compound of Formula I-V wherein $R_2$ is selected from Table C:

TABLE C

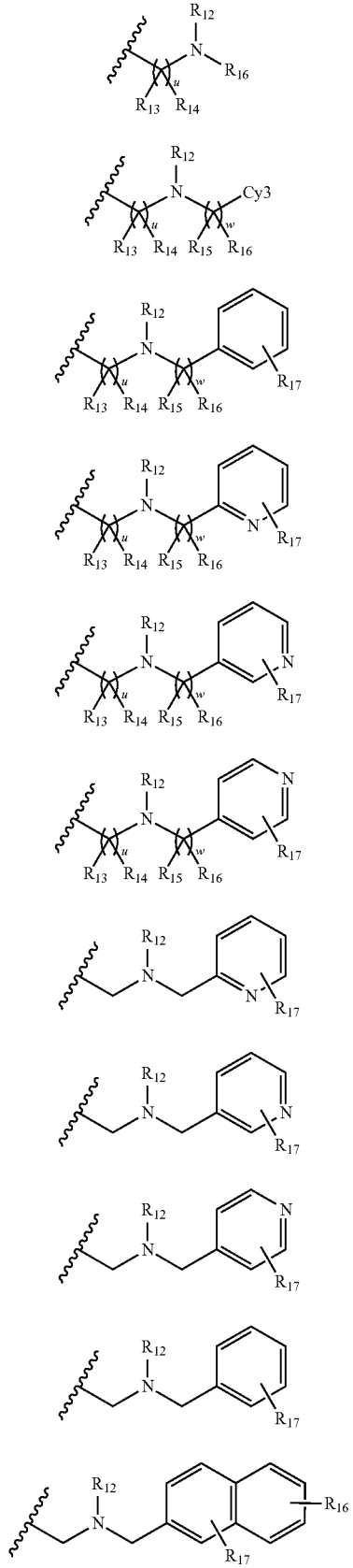

TABLE C-continued

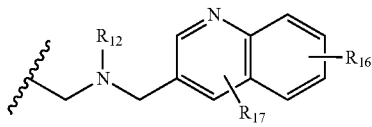

wherein u and w is independently 0, 1, 2, 3, 4, 5 or 6; and, Cy3 is optionally substituted cycloalkyl, optionally substituted cycloalkenyl, optionally substituted heterocyclyl, optionally substituted aryl or optionally substituted heteroaryl.

In a preferred embodiment, u is 1. In a preferred embodiment, w is 1. In a preferred embodiment, Cy3 is an optionally substituted aryl, more preferably an optionally substituted heteroaryl.

In a preferred embodiment, the invention relates to a compound of Formula I-III wherein Cy1 is selected from Table A, q is 1 and $R_{11}$ is selected from Table B, and $R_2$ is selected from Table C.

In one embodiment, the invention relates to a compound of Formula II-III wherein n is 0, $X_2$ is O, and Cy1 is an optionally substituted aryl. In a preferred embodiment, Cy1 is an optionally substituted phenyl ring. In a preferred embodiment Cy1 is a phenyl group and $R_{11}$ is selected from Table B, and $R_2$ is selected from Table C.

In one embodiment the invention relates to a compound of Formula I-V wherein $R_3$ is selected from Table D:

TABLE D

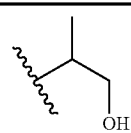

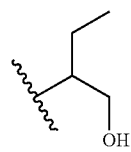 [SMILES: *C(CC)CO]

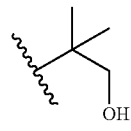 [SMILES: *C(C)(C)CO]

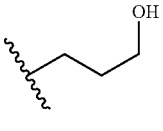 [SMILES: *CCCO]

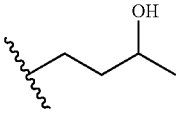 [SMILES: *CCC(C)O]

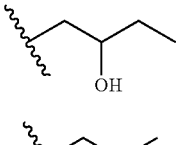

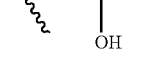

TABLE D-continued

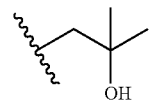 [SMILES: *CC(C)(C)O]

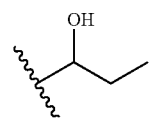

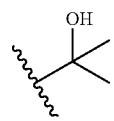

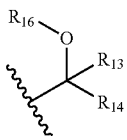

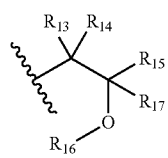

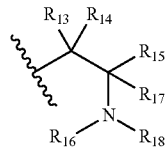

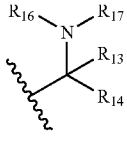

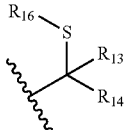

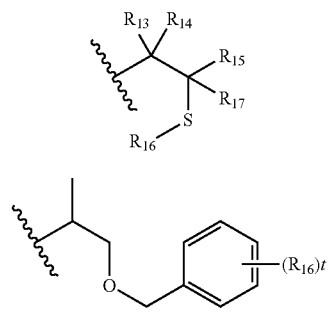

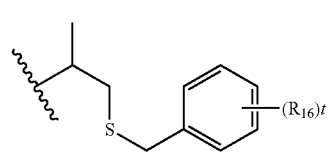

TABLE D-continued
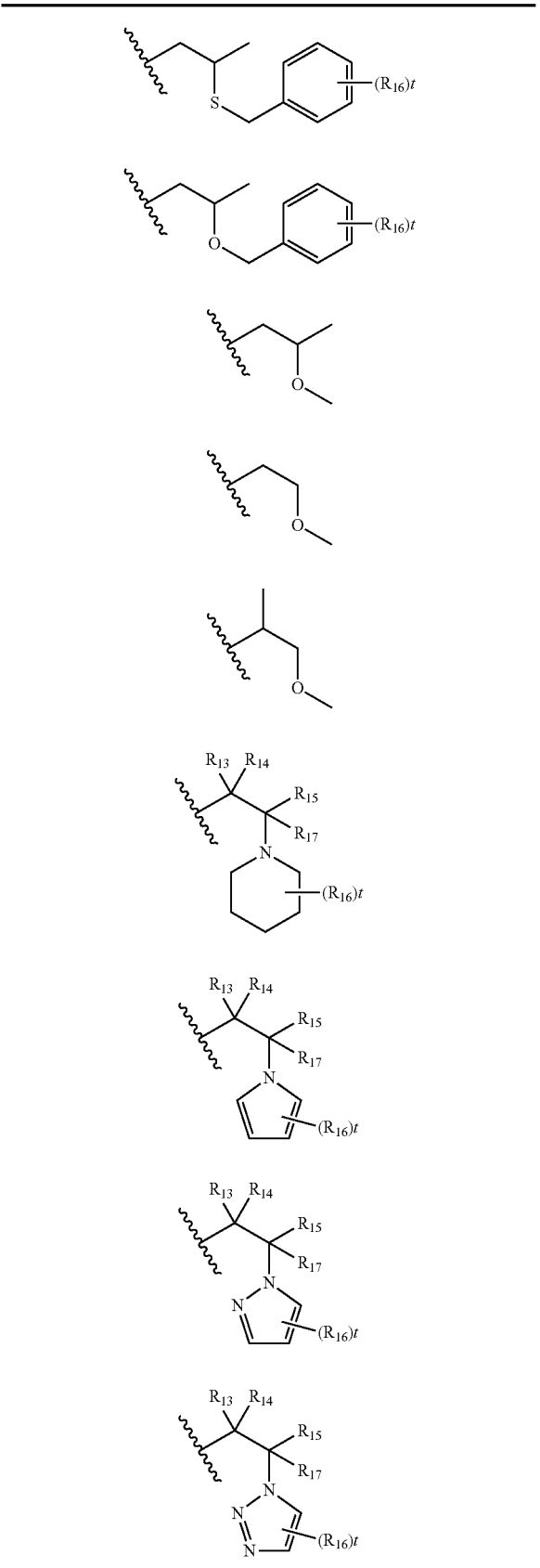
TABLE D-continued
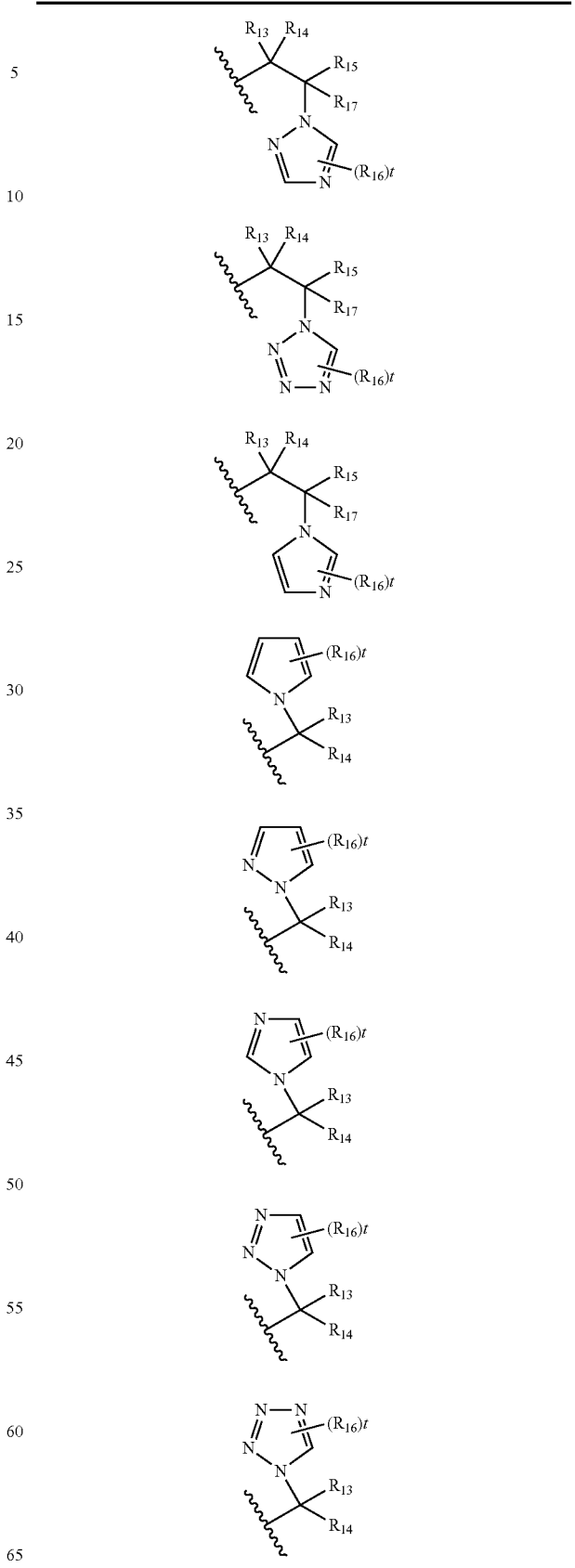

TABLE D-continued

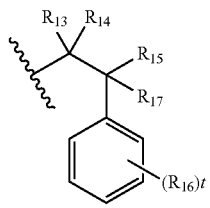

In a preferred embodiment, the invention relates to a compound of Formula I-V wherein Cy1 is selected from Table A, q is 1 and $R_{11}$ is selected from Table B, $R_2$ is selected from Table C, and $R_3$ is selected from Table D. In a more preferred embodiment, $R_4$ is an optionally substituted alkyl group, preferably a C1-C8 alkyl.

In one embodiment the invention relates to a compound of Formula III wherein $R_3$ is selected from Table E:

TABLE E

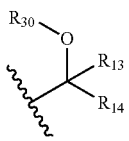

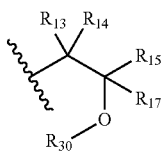

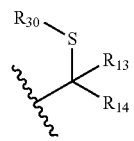

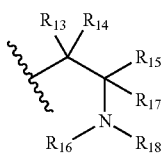

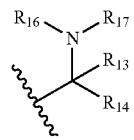

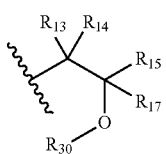

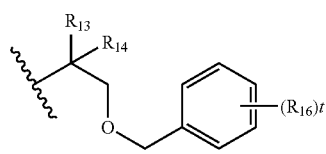

TABLE E-continued

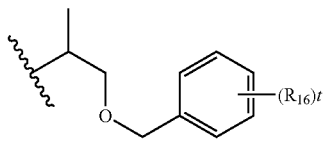

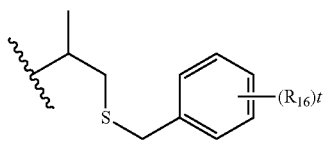

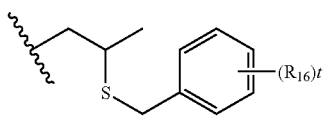

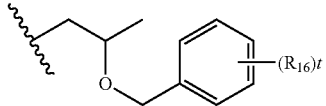

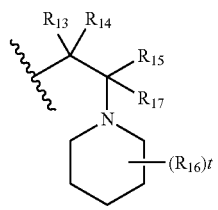

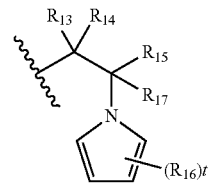

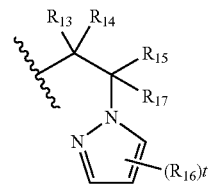

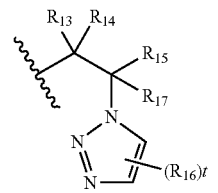

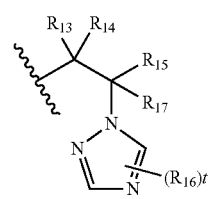

TABLE E-continued
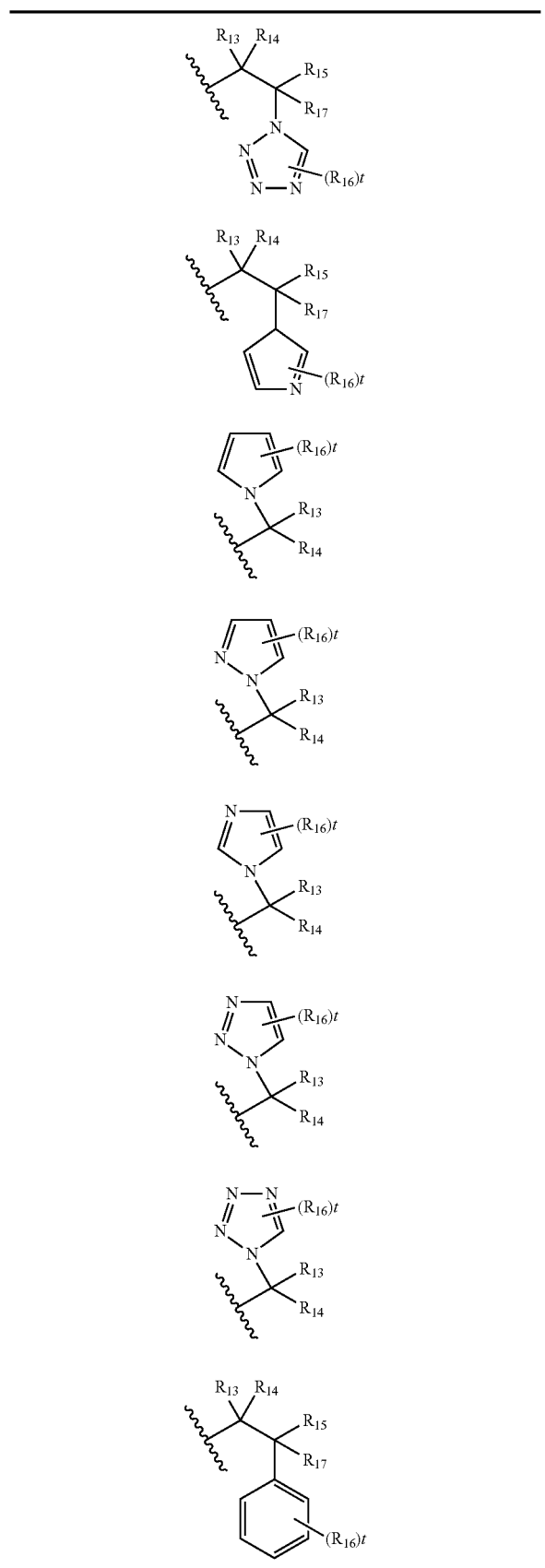
TABLE E-continued
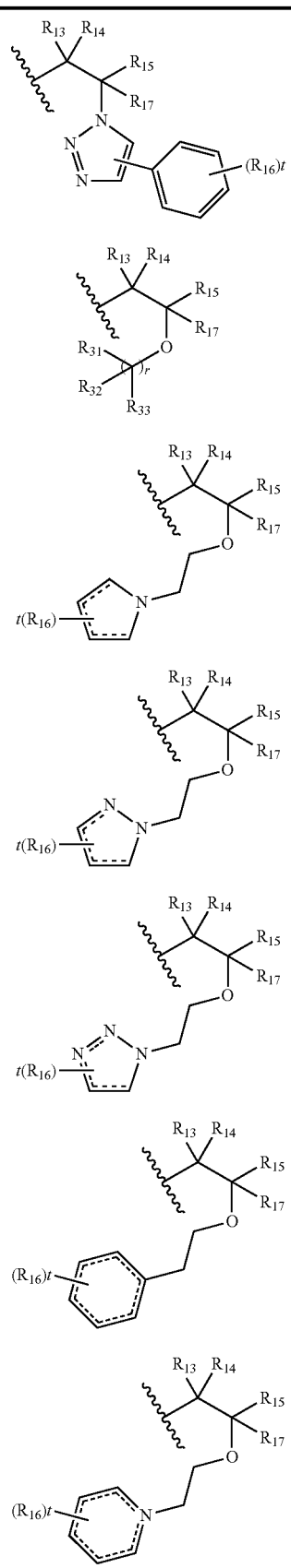

TABLE E-continued

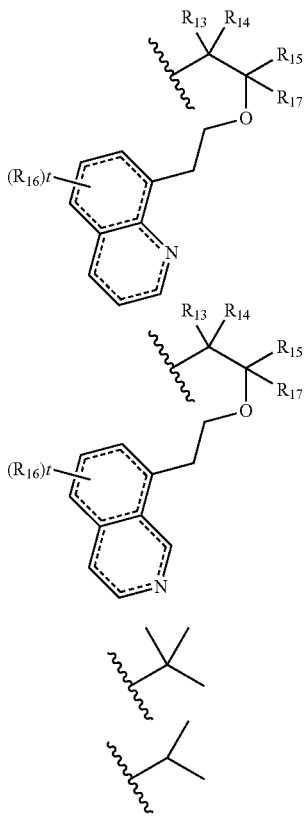

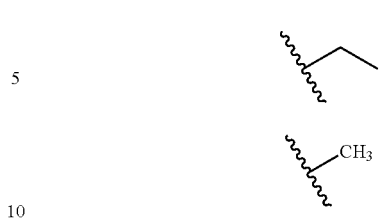

wherein, t, $R_{13}$, $R_{14}$, $R_{15}$, $R_{16}$, $R_{17}$ and $R_{18}$ are as defined above;

r is 1, 2, 3, 4, 5, 6, 7, 8, 9, 10, 11, 12, 13, 14 or 15;

$R_{30}$ is alkyl, substituted alkyl, aryl, substituted aryl, heteroaryl or substituted heteroaryl;

each $R_{31}$, and $R_{32}$ is independently hydrogen, alkyl, substituted alkyl, aryl, substituted aryl, heteroaryl or substituted heteroaryl; and, $R_{33}$ is alkyl, substituted alkyl, aryl, substituted aryl, heteroaryl, substituted heteroaryl, —$OR_{20}$, —$SR_{20}$, —$NR_{20}R_{21}$, —$CF_3$, —CN, —$NO_2$, —$N_3$, —$C(O)OR_{20}$, —$C(O)R_{20}$, —$C(O)NR_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl wherein $R_{20}$ and $R_{21}$ are as defined above.

In a preferred embodiment, $R_{30}$ is $C_1$-$C_{10}$ alkyl, $C_1$-$C_{10}$alkylaryl, or $C_1$-$C_{10}$alkylarylalkoxy.

In a preferred embodiment, $R_{16}$ is aryl, substituted aryl, heteroaryl or substituted heteroaryl.

In a preferred embodiment, a compound of Formula I is selected from Table 1:

TABLE 1

1
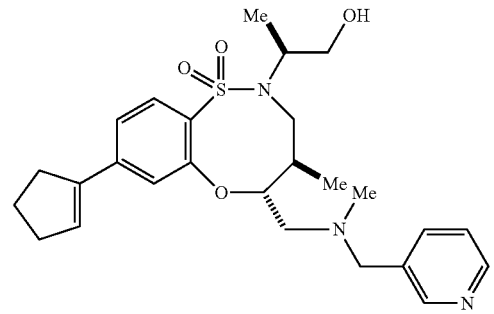 [SMILES: C[C@@H]1CN([C@@H](C)CO)S(=O)(=O)c2ccc(C3=CCCC3)cc2O[C@H]1CN(C)Cc1cccnc1]

(4R,5R)-8-(cyclopent-1-en-1-yl)-2-((S)-1-hydroxypropan-2-yl)-
4-methyl-5-((methyl(pyridin-3-ylmethyl)amino)methyl)-2,3,4,5-
tetrahydrobenzo[b][1,4,5]oxathiazocine 1,1-dioxide 2
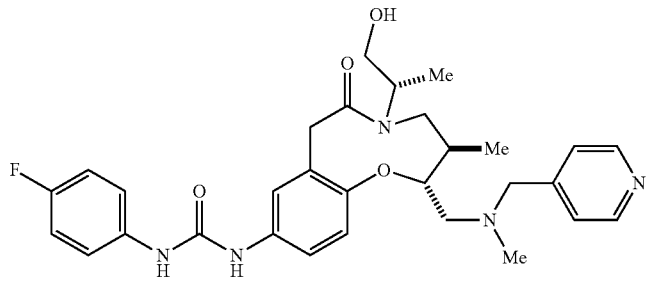 [SMILES: C[C@@H]1CN([C@@H](C)CO)C(=O)Cc2cc(NC(=O)Nc3ccc(F)cc3)ccc2O[C@H]1CN(C)Cc1ccncc1]

1-(4-fluorophenyl)-3-((2R,3R)-5-((S)-1-hydroxypropan-2-yl)-
3-methyl-2-((methyl(pyridin-4-ylmethyl)amino)methyl)-6-oxo-
2,3,4,5,6,7-hexahydrobenzo[h][1,5]oxazonin-9-yl)urea TABLE 1-continued

| 3 | 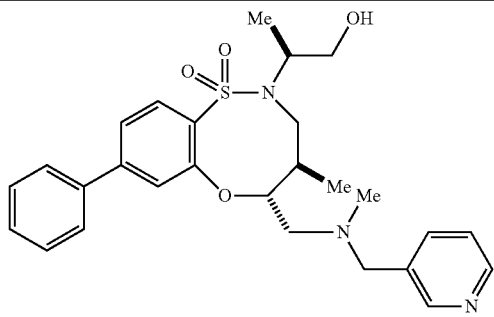
(4R,5R)-2-((S)-1-hydroxypropan-2-yl)-4-methyl-5-
((methyl(pyridin-3-ylmethyl)amino)methyl)-8-phenyl-
2,3,4,5-tetrahydrobenzo[b][1,4,5]oxathiazocine 1,1-dioxide |
| 4 | 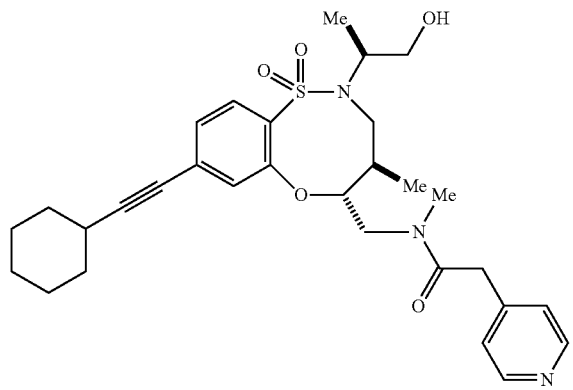 [SMILES: C[C@@H]1CN([C@@H](C)CO)S(=O)(=O)c2ccc(C#CC3CCCCC3)cc2O[C@H]1CN(C)C(=O)Cc1ccncc1]
N-(((4R,5R)-8-(cyclohexylethynyl)-2-((S)-1-hydroxypropan-2-yl)-4-
methyl-1,1-dioxido-2,3,4,5-tetrahydrobenzo[b][1,4,5]oxathiazocin-
5-yl)methyl)-N-methyl-2-(pyridin-4-yl)acetamide |
| 5 | 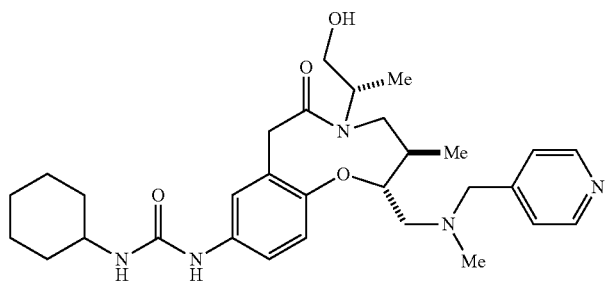 [SMILES: C[C@@H]1CN([C@@H](C)CO)C(=O)Cc2cc(NC(=O)NC3CCCCC3)ccc2O[C@H]1CN(C)Cc1ccncc1]
1-cyclohexyl-3-((2R,3R)-5-((S)-1-hydroxypropan-2-yl)-
3-methyl-2-((methyl(pyridin-4-ylmethyl)amino)methyl)-
6-oxo-2,3,4,5,6,7-hexahydrobenzo[h][1,5]oxazonin-9-yl)urea |
| 6 | 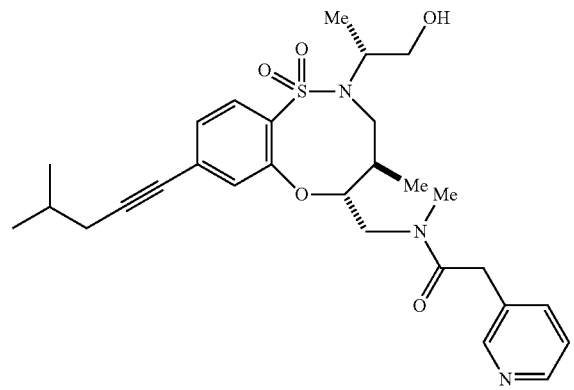 [SMILES: CC(C)CC#Cc1ccc2c(c1)O[C@@H](CN(C)C(=O)Cc1cccnc1)[C@H](C)CN([C@H](C)CO)S2(=O)=O]
N-(((4R,5R)-2-((R)-1-hydroxypropan-2-yl)-4-methyl-8-(4-methylpent-
1-yn-1-yl)-1,1-dioxido-2,3,4,5-tetrahydrobenzo[b][1,4,5]oxathiazocin-
5-yl)methyl)-N-methyl-2-(pyridin-3-yl)acetamide |

TABLE 1-continued

7

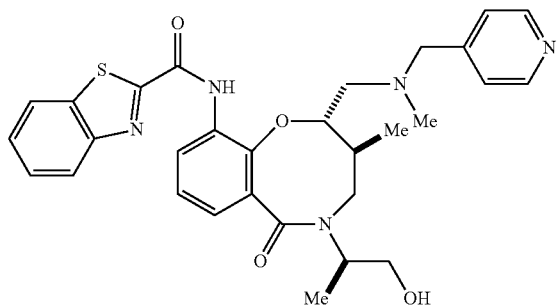 [SMILES: C[C@H](CO)N1C[C@H](C)[C@@H](CN(C)Cc2ccncc2)Oc2c(NC(=O)c3nc4ccccc4s3)cccc2C1=O]

N-((2S,3S)-5-((R)-1-hydroxypropan-2-yl)-3-methyl-2-
((methyl(pyridin-4-ylmethyl)amino)methyl)-6-oxo-3,4,5,6-
tetrahydro-2H-benzo[b][1,5]oxazocin-10-yl)benzo[d]thiazole-2-
carboxamide

8

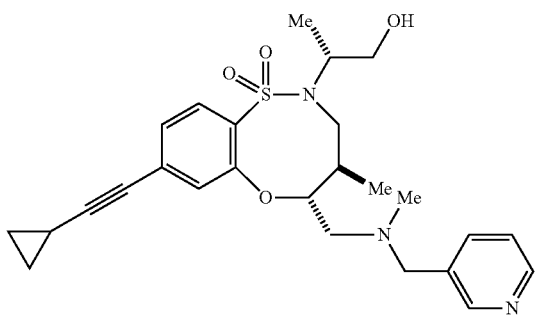 [SMILES: C[C@@H]1CN([C@H](C)CO)S(=O)(=O)c2ccc(C#CC3CC3)cc2O[C@H]1CN(C)Cc1cccnc1]

(4R,5R)-8-(cyclopropylethynyl)-2-((R)-1-hydroxypropan-2-yl)-
4-methyl-5-((methyl(pyridin-3-ylmethyl)amino)methyl)-
2,3,4,5-tetrahydrobenzo[b][1,4,5]oxathiazocine 1,1-dioxide

9

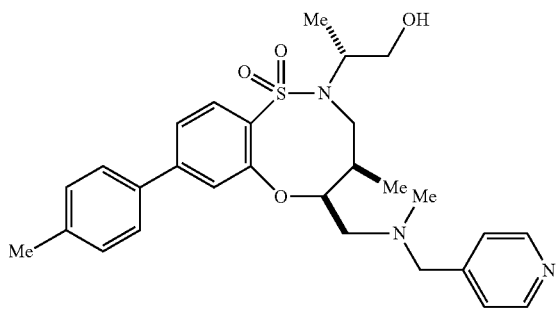 [SMILES: Cc1ccc(-c2ccc3c(c2)O[C@H](CN(C)Cc2ccncc2)[C@H](C)CN([C@H](C)CO)S3(=O)=O)cc1]

(4R,5S)-2-((R)-1-hydroxypropan-2-yl)-4-methyl-5-
((methyl(pyridin-4-ylmethyl)amino)methyl)-8-(p-tolyl)-
2,3,4,5-tetrahydrobenzo[b][1,4,5]oxathiazocine 1,1-dioxide

10

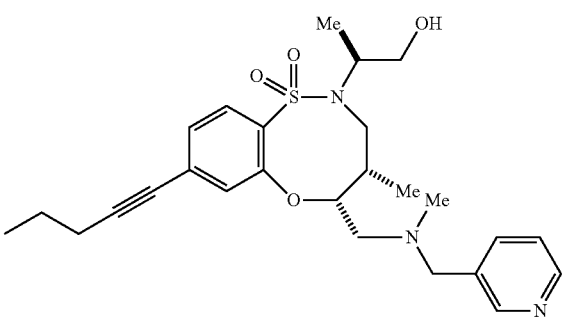 [SMILES: CCCC#Cc1ccc2c(c1)O[C@@H](CN(C)Cc1cccnc1)[C@@H](C)CN([C@@H](C)CO)S2(=O)=O]

(4S,5R)-2-((S)-1-hydroxypropan-2-yl)-4-methyl-5-
((methyl(pyridin-3-ylmethyl)amino)methyl)-8-(pent-1-
yn-1-yl)-2,3,4,5-tetrahydrobenzo[b][1,4,5]oxathiazocine 1,1-dioxide TABLE 1-continued

11

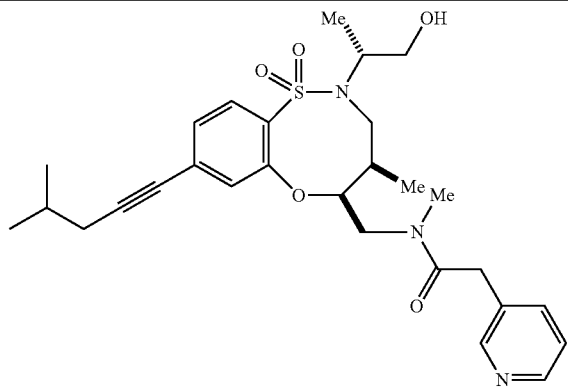

N-(((4R,5S)-2-((R)-1-hydroxypropan-2-yl)-4-methyl-8-(4-methylpent-1-yn-1-yl)-1,1-dioxido-2,3,4,5-tetrahydrobenzo[b][1,4,5]oxathiazocin-5-yl)methyl)-N-methyl-2-(pyridin-3-yl)acetamide

12

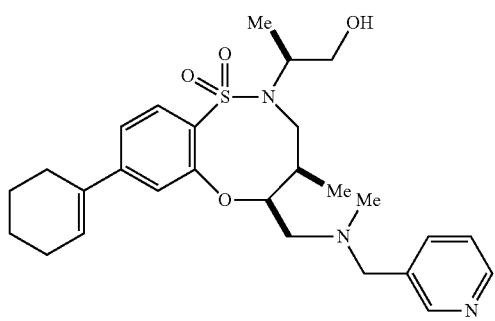 [SMILES: C[C@@H]1CN([C@@H](C)CO)S(=O)(=O)c2ccc(C3=CCCCC3)cc2O[C@@H]1CN(C)Cc1cccnc1]

(4R,5S)-8-(cyclohex-1-en-1-yl)-2-((S)-1-hydroxypropan-2-yl)-4-methyl-5-((methyl(pyridin-3-ylmethyl)amino)methyl)-2,3,4,5-tetrahydrobenzo[b][1,4,5]oxathiazocine 1,1-dioxide

13

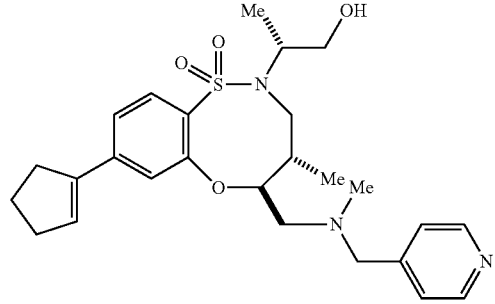 [SMILES: C[C@H](CO)N1C[C@H](C)[C@@H](CN(C)Cc2ccncc2)Oc2cc(C3=CCCC3)ccc2S1(=O)=O]

(4S,5S)-8-(cyclopent-1-en-1-yl)-2-((R)-1-hydroxypropan-2-yl)-4-methyl-5-((methyl(pyridin-4-ylmethyl)amino)methyl)-2,3,4,5-tetrahydrobenzo[b][1,4,5]oxathiazocine 1,1-dioxide

14

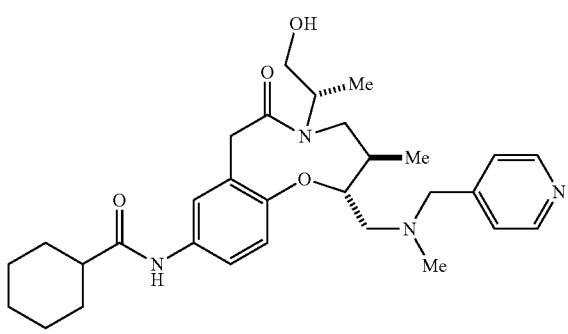 [SMILES: C[C@@H]1CN([C@@H](C)CO)C(=O)Cc2cc(NC(=O)C3CCCCC3)ccc2O[C@H]1CN(C)Cc1ccncc1]

N-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl)cyclohexanecarboxamide TABLE 1-continued

15

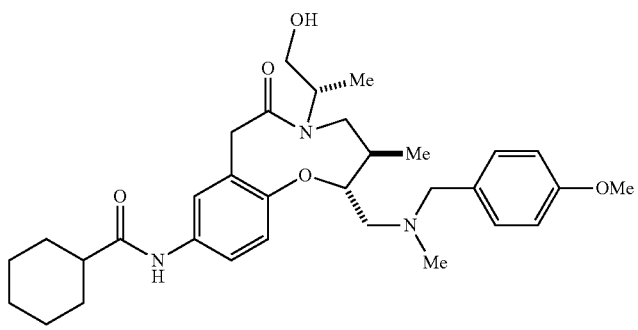 [SMILES: COc1ccc(CN(C)C[C@@H]2Oc3ccc(NC(=O)C4CCCCC4)cc3CC(=O)N([C@@H](C)CO)C[C@H]2C)cc1]

N-((2R,3R)-5-((S)-1-hydroxypropan-2-yl)-2-(((4-methoxybenzyl)
(methyl)amino)methyl)-3-methyl-6-oxo-2,3,4,5,6,7-
hexahydrobenzo[h][1,5]oxazonin-9-yl)cyclohexanecarboxamide

16

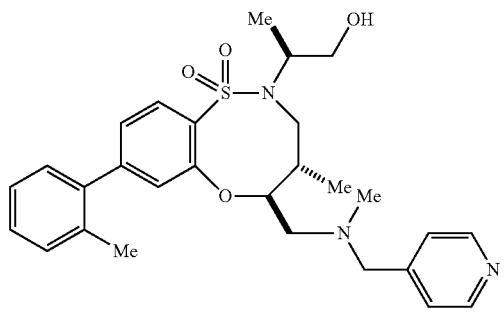 [SMILES: Cc1ccccc1-c1ccc2c(c1)O[C@H](CN(C)Cc1ccncc1)[C@@H](C)CN([C@@H](C)CO)S2(=O)=O]

(4S,5S)-2-((S)-1-hydroxypropan-2-yl)-4-methyl-5-
((methyl(pyridin-4-ylmethyl)amino)methyl)-8-(o-tolyl)-
2,3,4,5-tetrahydrobenzo[b][1,4,5]oxathiazocine 1,1-dioxide

17

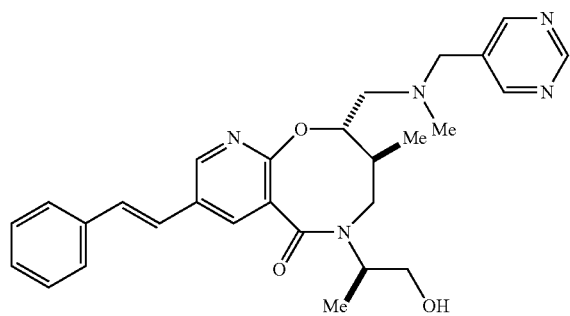 [SMILES: C[C@H](CO)N1C[C@H](C)[C@@H](CN(C)Cc2cncnc2)Oc2ncc(/C=C/c3ccccc3)cc2C1=O]

(2S,3S)-5-((R)-1-hydroxypropan-2-yl)-3-methyl-2-
((methyl(pyrimidin-5-ylmethyl)amino)methyl)-8-((E)-
styryl)-4,5-dihydro-2H-pyrido[2,3-b][1,5]oxazocin-6(3H)-one

18

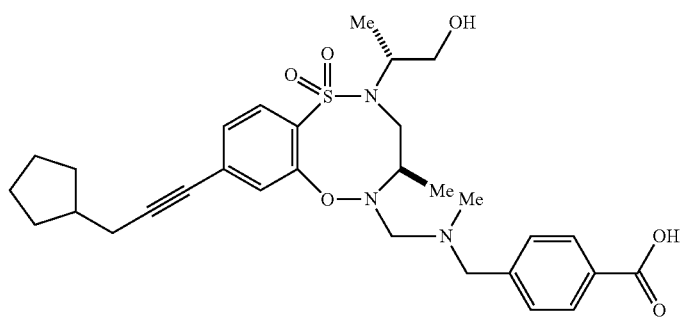 [SMILES: C[C@@H]1CN([C@H](C)CO)S(=O)(=O)c2ccc(C#CCC3CCCC3)cc2ON1CN(C)Cc1ccc(C(=O)O)cc1]

4-(((((4R,5R)-8-(3-cyclopentylprop-1-yn-1-yl)-2-((R)-1-hydroxypropan-2-yl)-
4-methyl-1,1-dioxido-2,3,4,5-tetrahydrobenzo[b][1,4,5]oxathiazocin-
5-yl)methyl)(methyl)amino)methyl)benzoic acid TABLE 1-continued

| 19 | 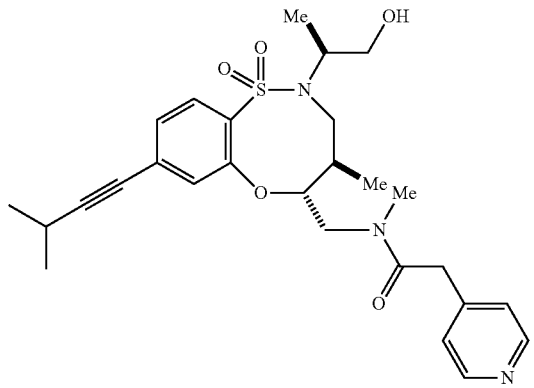 [SMILES: CC(C)C#Cc1ccc2c(c1)O[C@@H](CN(C)C(=O)Cc1ccncc1)[C@H](C)CN([C@@H](C)CO)S2(=O)=O] |

N-(((4R,5R)-2-((S)-1-hydroxypropan-2-yl)-4-methyl-8-(3-methylbut-1-yn-1-yl)-1,1-dioxido-2,3,4,5-tetrahydrobenzo[b][1,4,5]oxathiazocin-5-yl)methyl)-N-methylnicotinamide

| 20 | 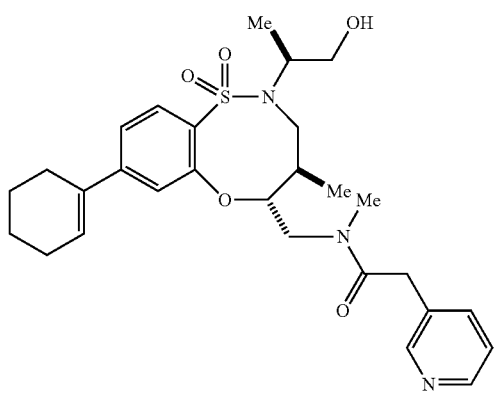 [SMILES: C[C@@H]1CN([C@@H](C)CO)S(=O)(=O)c2ccc(C3=CCCCC3)cc2O[C@H]1CN(C)C(=O)Cc1cccnc1] |

N-(((4R,5R)-8-(cyclohex-1-en-1-yl)-2-((S)-1-hydroxypropan-2-yl)-4-methyl-1,1-dioxido-2,3,4,5-tetrahydrobenzo[b][1,4,5]oxathiazocin-5-yl)methyl)-N-methyl-2-(pyridin-3-yl)acetamide

| 21 | 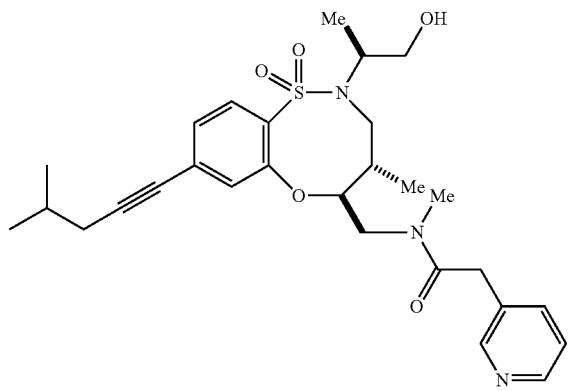 [SMILES: CC(C)CC#Cc1ccc2c(c1)O[C@H](CN(C)C(=O)Cc1cccnc1)[C@@H](C)CN([C@@H](C)CO)S2(=O)=O] |

N-(((4S,5S)-2-((S)-1-hydroxypropan-2-yl)-4-methyl-8-(4-methylpent-1-yn-1-yl)-1,1-dioxido-2,3,4,5-tetrahydrobenzo[b][1,4,5]oxathiazocin-5-yl)methyl)-N-methyl-2-(pyridin-3-yl)acetamide TABLE 1-continued

| 22 | 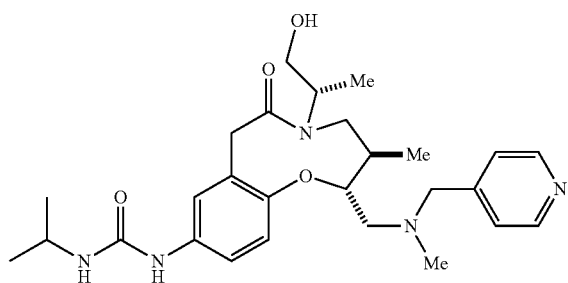 [SMILES: CC(C)NC(=O)Nc1ccc2c(c1)CC(=O)N([C@@H](C)CO)C[C@@H](C)[C@H](CN(C)Cc1ccncc1)O2] |

1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-isopropylurea

| 23 | 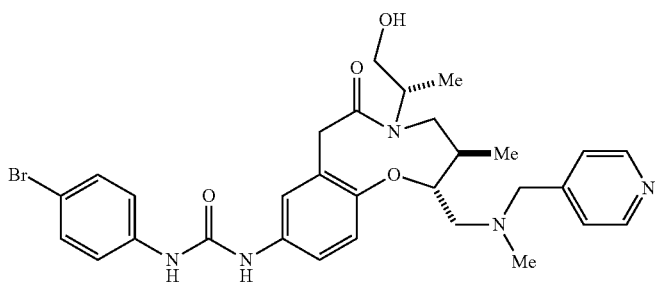 |

1-(4-bromophenyl)-3-((2R,3R)-5-((S)-1-hydroxypropan-2-yl)-3-
methyl-2-((methyl(pyridin-4-ylmethyl)amino)methyl)-6-oxo-
2,3,4,5,6,7-hexahydrobenzo[h][1,5]oxazonin-9-yl)urea

| 24 | 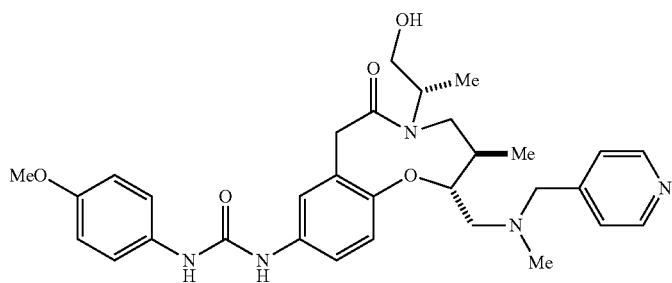 [SMILES: COc1ccc(NC(=O)Nc2ccc3c(c2)CC(=O)N([C@@H](C)CO)C[C@@H](C)[C@H](CN(C)Cc2ccncc2)O3)cc1] |

1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-(4-methoxyphenyl)urea

| 25 | 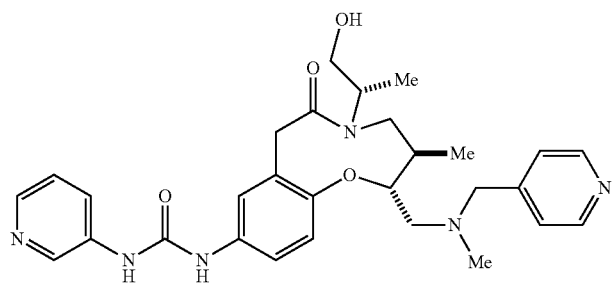 [SMILES: C[C@@H]1CN([C@@H](C)CO)C(=O)Cc2cc(NC(=O)Nc3cccnc3)ccc2O[C@H]1CN(C)Cc1ccncc1] |

1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-(pyridin-3-yl)urea

| 26 | 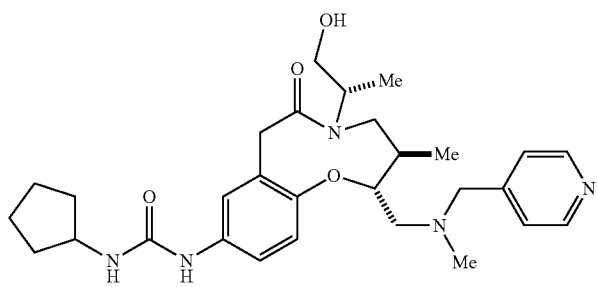 [SMILES: C[C@@H]1CN([C@@H](C)CO)C(=O)Cc2cc(NC(=O)NC3CCCC3)ccc2O[C@H]1CN(C)Cc1ccncc1]
1-cyclopentyl-3-((2R,3R)-5-((S)-1-hydroxypropan-2-yl)-3-methyl-
2-((methyl(pyridin-4-ylmethyl)amino)methyl)-6-oxo-2,3,4,5,6,7-
hexahydrobenzo[h][1,5]oxazonin-9-yl)urea |

| 27 | 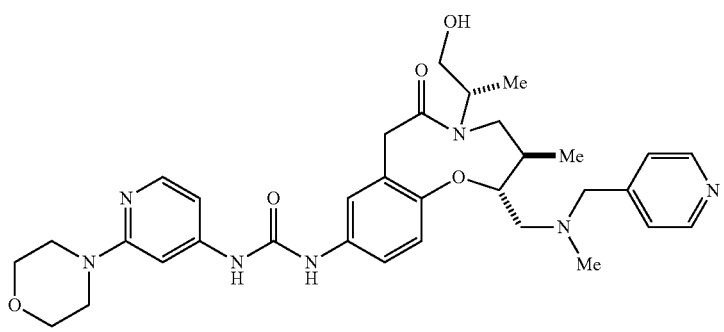 [SMILES: C[C@@H]1CN([C@@H](C)CO)C(=O)Cc2cc(NC(=O)Nc3ccnc(N4CCOCC4)c3)ccc2O[C@H]1CN(C)Cc1ccncc1]
1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-(2-morpholinopyridin-4-yl)urea |

| 28 | 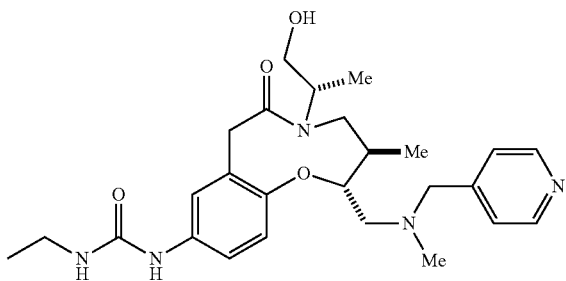 [SMILES: CCNC(=O)Nc1ccc2c(c1)CC(=O)N([C@@H](C)CO)C[C@@H](C)[C@H](CN(C)Cc1ccncc1)O2]
1-ethyl-3-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)urea |

| 29 | 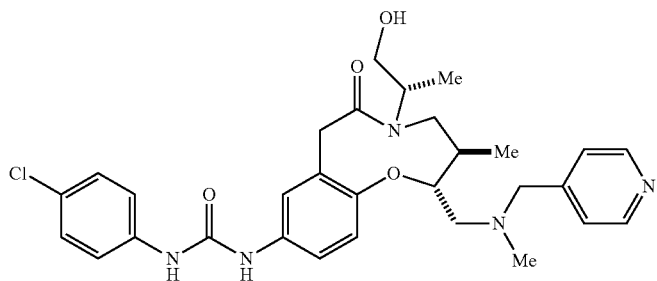 [SMILES: C[C@@H]1CN([C@@H](C)CO)C(=O)Cc2cc(NC(=O)Nc3ccc(Cl)cc3)ccc2O[C@H]1CN(C)Cc1ccncc1]
1-(4-chlorophenyl)-3-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)urea |

TABLE 1-continued

| 30 | 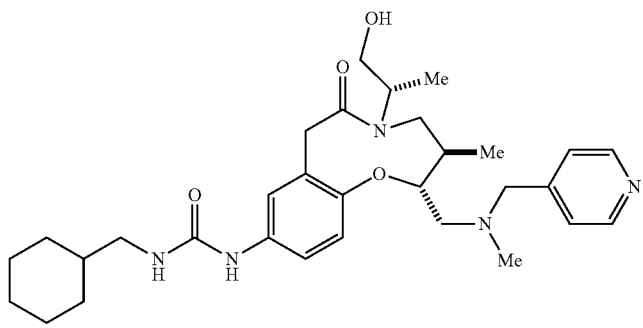 [SMILES: C[C@@H]1CN([C@@H](C)CO)C(=O)Cc2cc(NC(=O)NCC3CCCCC3)ccc2O[C@H]1CN(C)Cc1ccncc1]
1-(cyclohexylmethyl)-3-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl)urea |

| 31 | 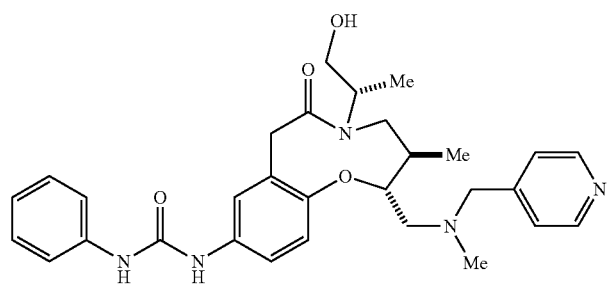 [SMILES: C[C@@H]1CN([C@@H](C)CO)C(=O)Cc2cc(NC(=O)Nc3ccccc3)ccc2O[C@H]1CN(C)Cc1ccncc1]
1-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl)-3-phenylurea |

| 32 | 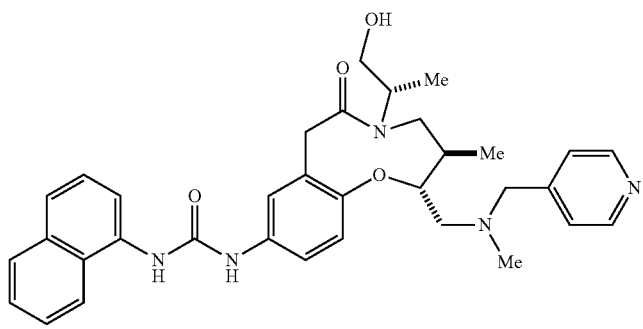 [SMILES: C[C@@H]1CN([C@@H](C)CO)C(=O)Cc2cc(NC(=O)Nc3cccc4ccccc34)ccc2O[C@H]1CN(C)Cc1ccncc1]
1-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl)-3-(naphthalen-1-yl)urea |

| 33 | 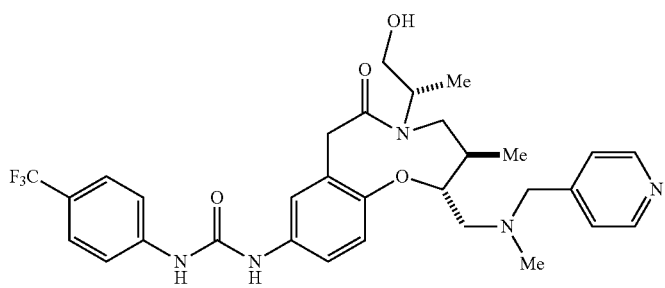 [SMILES: C[C@@H]1CN([C@@H](C)CO)C(=O)Cc2cc(NC(=O)Nc3ccc(C(F)(F)F)cc3)ccc2O[C@H]1CN(C)Cc1ccncc1]
1-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl)-3-(4-(trifluoromethyl)phenyl)urea |

TABLE 1-continued

34

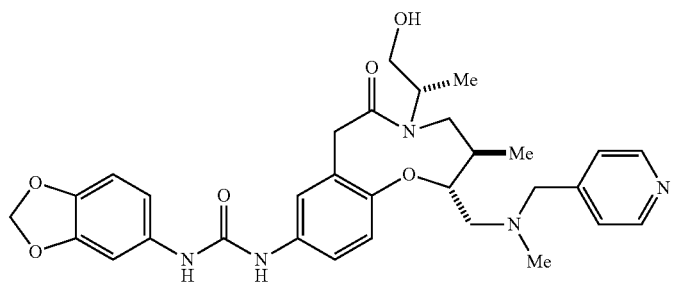 [SMILES: C[C@@H]1CN([C@@H](C)CO)C(=O)Cc2cc(NC(=O)Nc3ccc4c(c3)OCO4)ccc2O[C@H]1CN(C)Cc1ccncc1]

1-(benzo[d][1,3]dioxol-5-yl)-3-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)urea

35

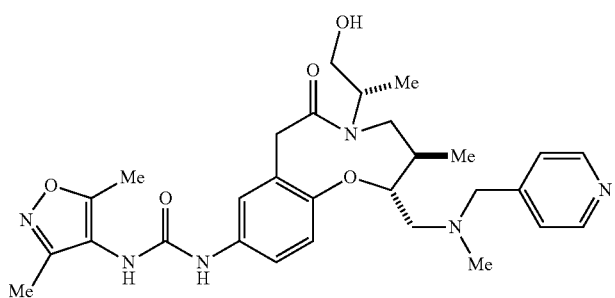 [SMILES: Cc1noc(C)c1NC(=O)Nc1ccc2c(c1)CC(=O)N([C@@H](C)CO)C[C@@H](C)[C@H](CN(C)Cc1ccncc1)O2]

1-(3,5-dimethylisoxazol-4-yl)-3-((2R,3R)-5-((S)-1-hydroxypropan-2-yl)-3-
methyl-2-((methyl(pyridin-4-ylmethyl)amino)methyl)-6-oxo-2,3,4,5,6,7-
hexahydrobenzo[h][1,5]oxazonin-9-yl)urea

36

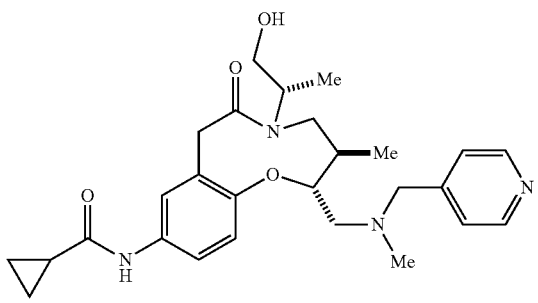 [SMILES: C[C@@H]1CN([C@@H](C)CO)C(=O)Cc2cc(NC(=O)C3CC3)ccc2O[C@H]1CN(C)Cc1ccncc1]

N-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)cyclopropanecarboxamide

37

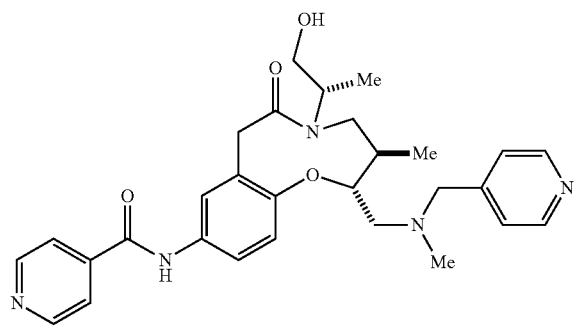 [SMILES: C[C@@H]1CN([C@@H](C)CO)C(=O)Cc2cc(NC(=O)c3ccncc3)ccc2O[C@H]1CN(C)Cc1ccncc1]

N-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)isonicotinamide

TABLE 1-continued

| 38 | 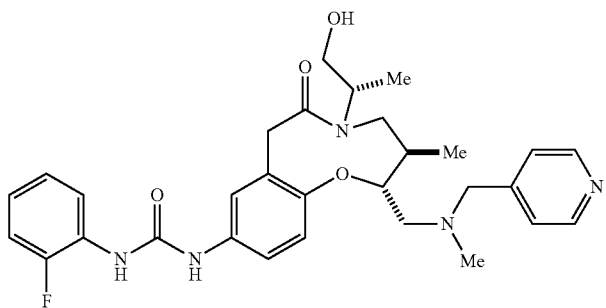 [SMILES: C[C@@H]1CN([C@@H](C)CO)C(=O)Cc2cc(NC(=O)Nc3ccccc3F)ccc2O[C@H]1CN(C)Cc1ccncc1] |

1-(2-fluorophenyl)-3-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)urea

| 39 | 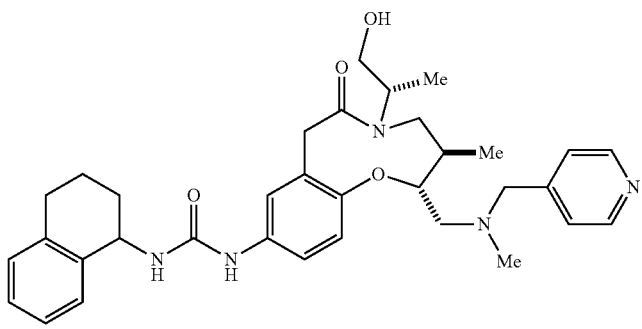 [SMILES: C[C@@H]1CN([C@@H](C)CO)C(=O)Cc2cc(NC(=O)NC3CCCc4ccccc43)ccc2O[C@H]1CN(C)Cc1ccncc1] |

1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-(1,2,3,4-tetrahydronaphthalen-1-yl)urea

| 40 | 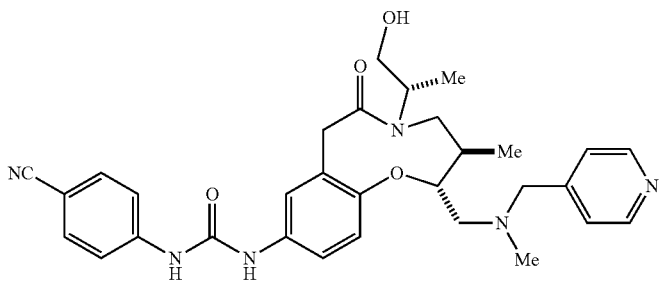 [SMILES: C[C@@H]1CN([C@@H](C)CO)C(=O)Cc2cc(NC(=O)Nc3ccc(C#N)cc3)ccc2O[C@H]1CN(C)Cc1ccncc1] |

1-(4-cyanophenyl)-3-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)urea

| 41 | 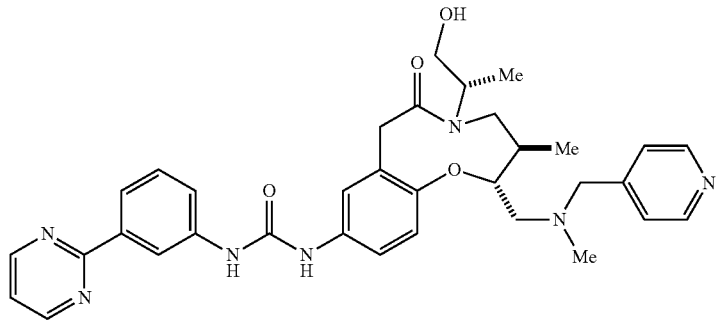 [SMILES: C[C@@H]1CN([C@@H](C)CO)C(=O)Cc2cc(NC(=O)Nc3cccc(-c4ncccn4)c3)ccc2O[C@H]1CN(C)Cc1ccncc1] |

1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-(3-(pyrimidin-2-yl)phenyl)urea TABLE 1-continued

| 42 | 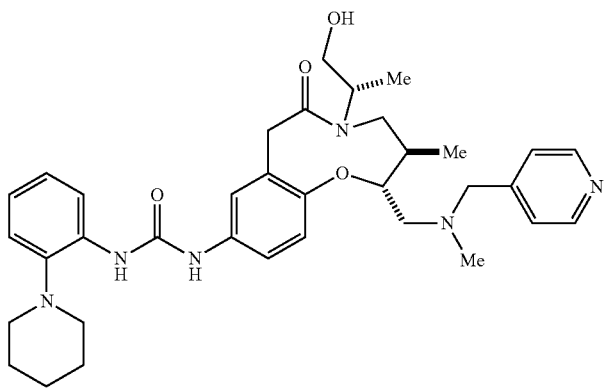 [SMILES: C[C@@H]1CN([C@@H](C)CO)C(=O)Cc2cc(NC(=O)Nc3ccccc3N3CCCCC3)ccc2O[C@H]1CN(C)Cc1ccncc1] |

1-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)-3-(2-(piperidin-1-yl)phenyl)urea

| 43 | 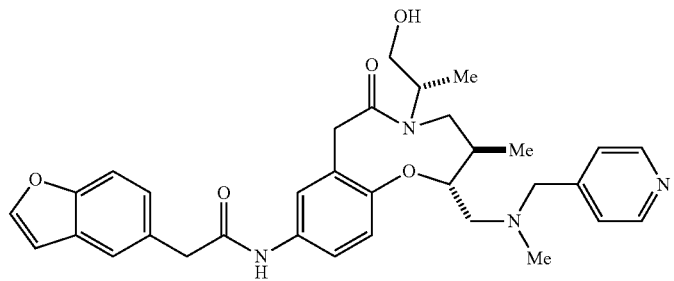 [SMILES: C[C@@H]1CN([C@@H](C)CO)C(=O)Cc2cc(NC(=O)Cc3ccc4occc4c3)ccc2O[C@H]1CN(C)Cc1ccncc1] |

1-(benzofuran-5-yl)-3-((2R,3R)-5-((S)-1-hydroxypropan-2-yl)-3-methyl-2-
((methyl(pyridin-4-ylmethyl)amino)methyl)-6-oxo-2,3,4,5,6,7-
hexahydrobenzo[h][1,5]oxazonin-9-yl)urea

| 44 | 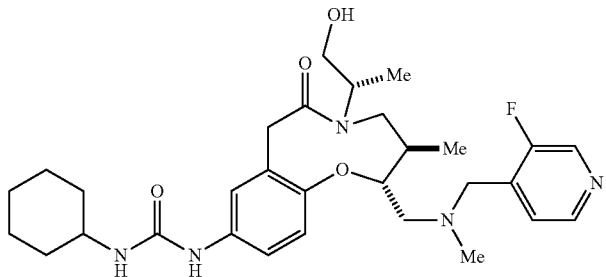 [SMILES: C[C@@H]1CN([C@@H](C)CO)C(=O)Cc2cc(NC(=O)NC3CCCCC3)ccc2O[C@H]1CN(C)Cc1ccncc1F] |

1-cyclohexyl-3-((2R,3R)-2-((((3-fluoropyridin-4-yl)methyl)(methyl)amino)methyl)-
5-((S)-1-hydroxypropan-2-yl)-3-methyl-6-oxo-2,3,4,5,6,7-
hexahydrobenzo[h][1,5]oxazonin-9-yl)urea

| 45 | 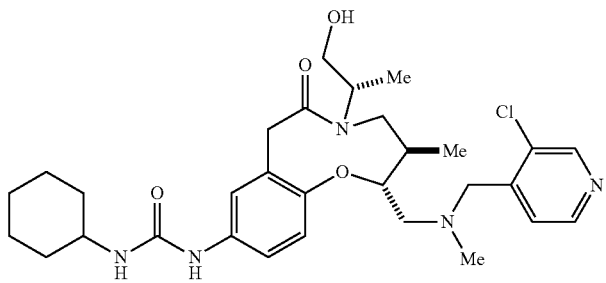 [SMILES: C[C@@H]1CN([C@@H](C)CO)C(=O)Cc2cc(NC(=O)NC3CCCCC3)ccc2O[C@H]1CN(C)Cc1ccncc1Cl] |

1-((2R,3R)-2-((((3-chloropyridin-4-yl)methyl)(methyl)amino)methyl)-
5-((S)-1-hydroxypropan-2-yl)-3-methyl-6-oxo-2,3,4,5,6,7-
hexahydrobenzo[h][1,5]oxazonin-9-yl)-3-cyclohexylurea

TABLE 1-continued

46

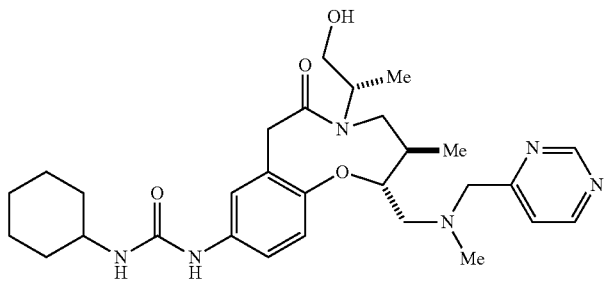 [SMILES: C[C@@H]1CN([C@@H](C)CO)C(=O)Cc2cc(NC(=O)NC3CCCCC3)ccc2O[C@H]1CN(C)Cc1ccncn1]

1-cyclohexyl-3-((2R,3R)-5-((S)-1-hydroxypropan-2-yl)-3-methyl-2-
((methyl(pyrimidin-4-ylmethyl)amino)methyl)-6-oxo-2,3,4,5,6,7-
hexahydrobenzo[h][1,5]oxazonin-9-yl)urea

47

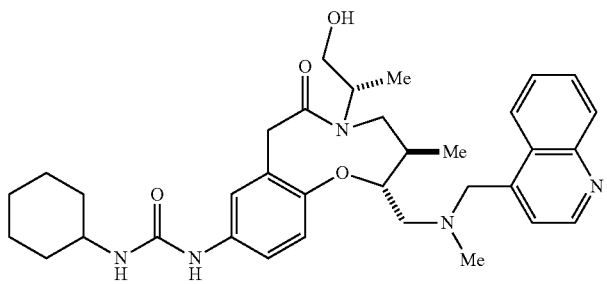 [SMILES: C[C@@H]1CN([C@@H](C)CO)C(=O)Cc2cc(NC(=O)NC3CCCCC3)ccc2O[C@H]1CN(C)Cc1ccnc2ccccc12]

1-cyclohexyl-3-((2R,3R)-5-((S)-1-hydroxypropan-2-yl)-3-methyl-2-
((methyl(quinolin-4-ylmethyl)amino)methyl)-6-oxo-2,3,4,5,6,7-
hexahydrobenzo[h][1,5]oxazonin-9-yl)urea

48

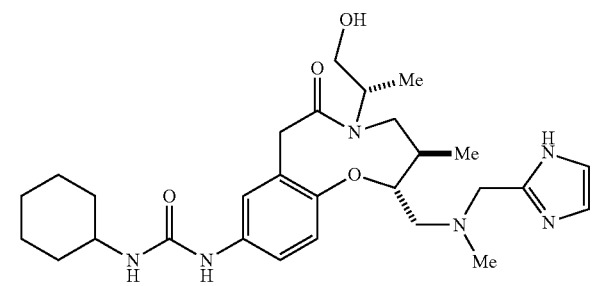 [SMILES: C[C@@H]1CN([C@@H](C)CO)C(=O)Cc2cc(NC(=O)NC3CCCCC3)ccc2O[C@H]1CN(C)Cc1ncc[nH]1]

1-((2R,3R)-2-(((((1H-imidazol-2-yl)methyl)(methyl)amino)methyl)-5-
((S)-1-hydroxypropan-2-yl)-3-methyl-6-oxo-2,3,4,5,6,7-
hexahydrobenzo[h][1,5]oxazonin-9-yl)-3-cyclohexylurea

49

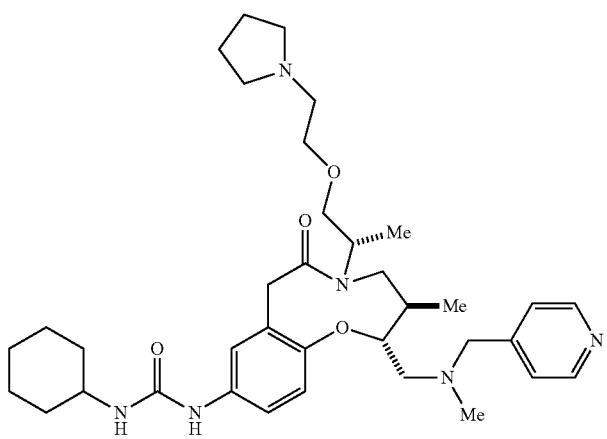 [SMILES: C[C@@H]1CN([C@@H](C)COCCN2CCCC2)C(=O)Cc2cc(NC(=O)NC3CCCCC3)ccc2O[C@H]1CN(C)Cc1ccncc1]

1-cyclohexyl-3-((2R,3R)-3-methyl-2-((methyl(pyridin-4-ylmethyl)amino)methyl)-
6-oxo-5-((S)-1-(2-(pyrrolidin-1-yl)ethoxy)propan-2-yl)-2,3,4,5,6,7-
hexahydrobenzo[h][1,5]oxazonin-9-yl)urea TABLE 1-continued

50

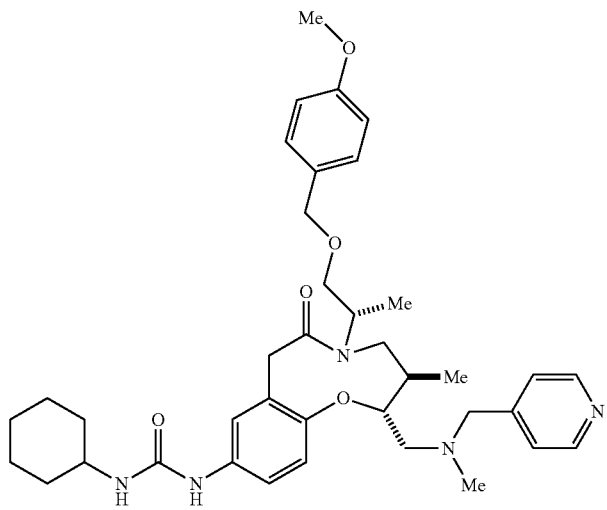 [SMILES: COc1ccc(COC[C@H](C)N2C[C@@H](C)[C@H](CN(C)Cc3ccncc3)Oc3ccc(NC(=O)NC4CCCCC4)cc3CC2=O)cc1]

1-cyclohexyl-3-((2R,3R)-5-((S)-1-((4-methoxybenzyl)oxy)propan-2-yl)-3-
methyl-2-((methyl(pyridin-4-ylmethyl)amino)methyl)-6-oxo-2,3,4,5,6,7-
hexahydrobenzo[h][1,5]oxazonin-9-yl)urea

51

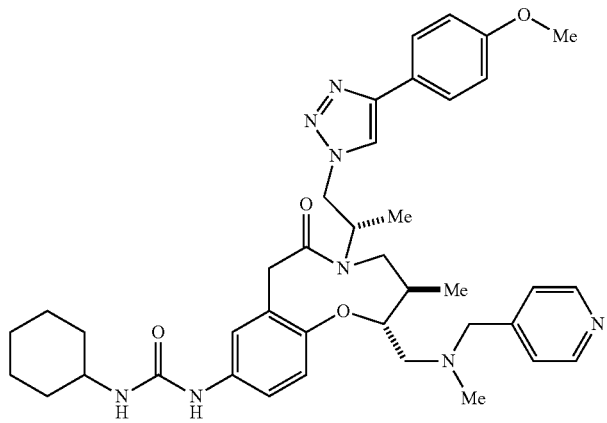 [SMILES: COc1ccc(-c2cn(C[C@H](C)N3C[C@@H](C)[C@H](CN(C)Cc4ccncc4)Oc4ccc(NC(=O)NC5CCCCC5)cc4CC3=O)nn2)cc1]

1-cyclohexyl-3-((2R,3R)-5-((S)-1-(4-(4-methoxyphenyl)-1H-1,2,3-triazol-1-yl)propan-
2-yl)-3-methyl-2-((methyl(pyridin-4-ylmethyl)amino)methyl)-6-oxo-2,3,4,5,6,7-
hexahydrobenzo[h][1,5]oxazonin-9-yl)urea

52

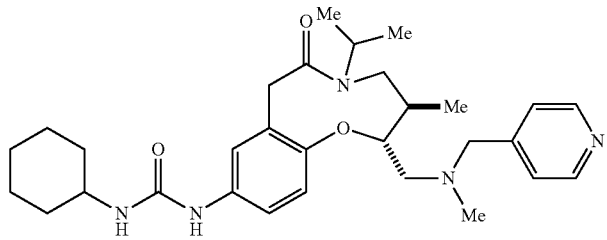 [SMILES: CC(C)N1C[C@@H](C)[C@H](CN(C)Cc2ccncc2)Oc2ccc(NC(=O)NC3CCCCC3)cc2CC1=O]

1-cyclohexyl-3-((2R,3R)-5-isopropyl-3-methyl-2-
((methyl(pyridin-4-ylmethyl)amino)methyl)-6-oxo-
2,3,4,5,6,7-hexahydrobenzo[h][1,5]oxazonin-9-yl)urea

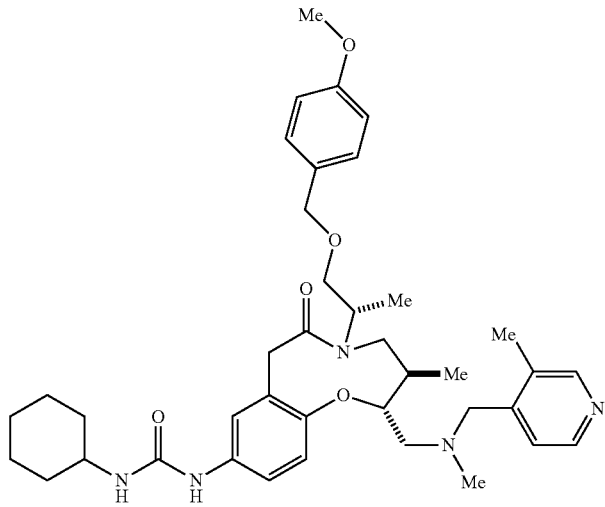 [SMILES: COc1ccc(COC[C@H](C)N2C[C@@H](C)[C@H](CN(C)Cc3ccncc3C)Oc3ccc(NC(=O)NC4CCCCC4)cc3CC2=O)cc1]

1-cyclohexyl-3-((2R,3R)-5-((S)-1-((4-methoxybenzyl)oxy)propan-2-yl)-3-methyl-2-((methyl((3-methylpyridin-4-yl)methyl)amino)methyl)-6-oxo-2,3,4,5,6,7-hexahydrobenzo[h][1,5]oxazonin-9-yl)urea The invention further relates to a process for preparing compounds of Formula I-V. Scheme 1 shows a general methodology for the synthesis of medium-sized ring scaffolds from a common linear intermediate used for the synthesis of final compounds.

Scheme 1: General protocol for synthesis of compounds of Formula I

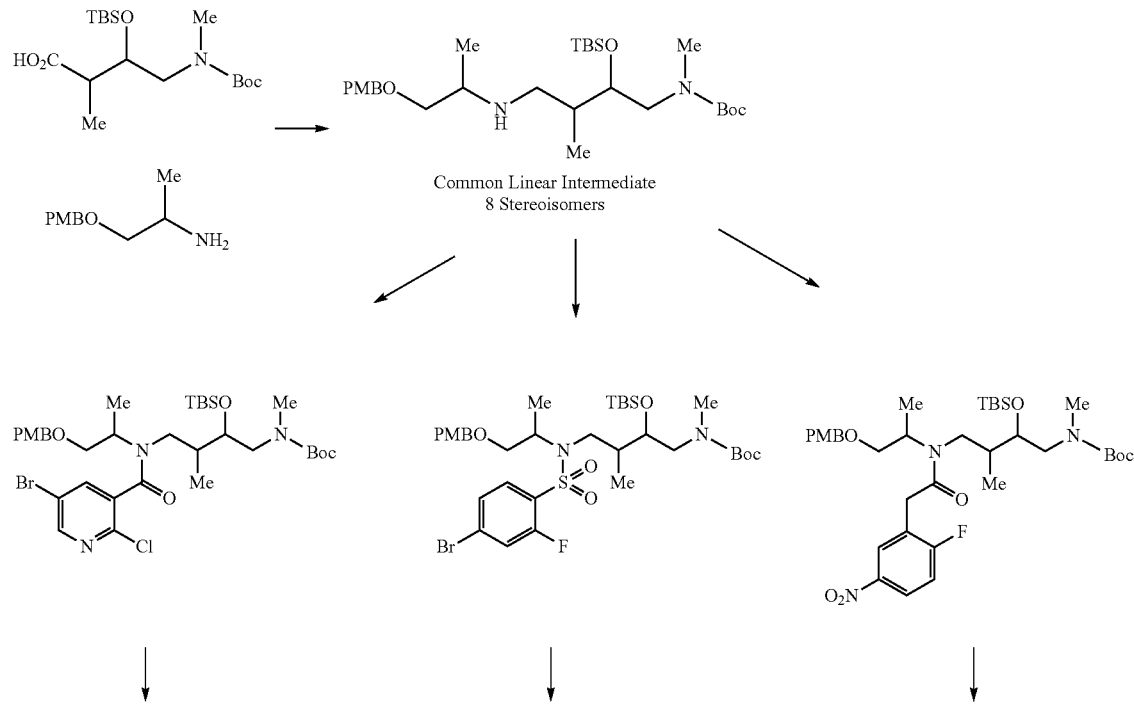

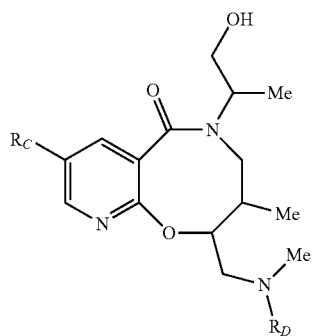

8 Stereoisomers

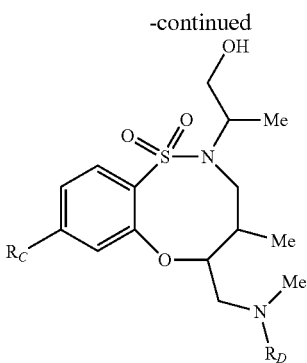

8 Stereoisomers

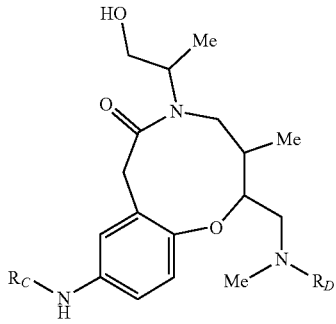

8 Stereoisomers $R_c$ and $R_D$ are each independently hydrogen, halogen, —$OR_{20}$, —$SR_{20}$, —$NR_{20}R_{21}$, —$CF_3$, —CN, —$NO_2$, —$N_3$, —$C(O)R_{20}$, —$C(O)OR_{20}$, —$C(O)NR_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl.

For this synthetic route (Scheme 1), intermediates and medium-sized ring scaffolds were synthesized using the procedures similar to Marcaurelle, L. A. et al., *J. Am. Chem. Soc.* 2010, 132, 16962-16976.

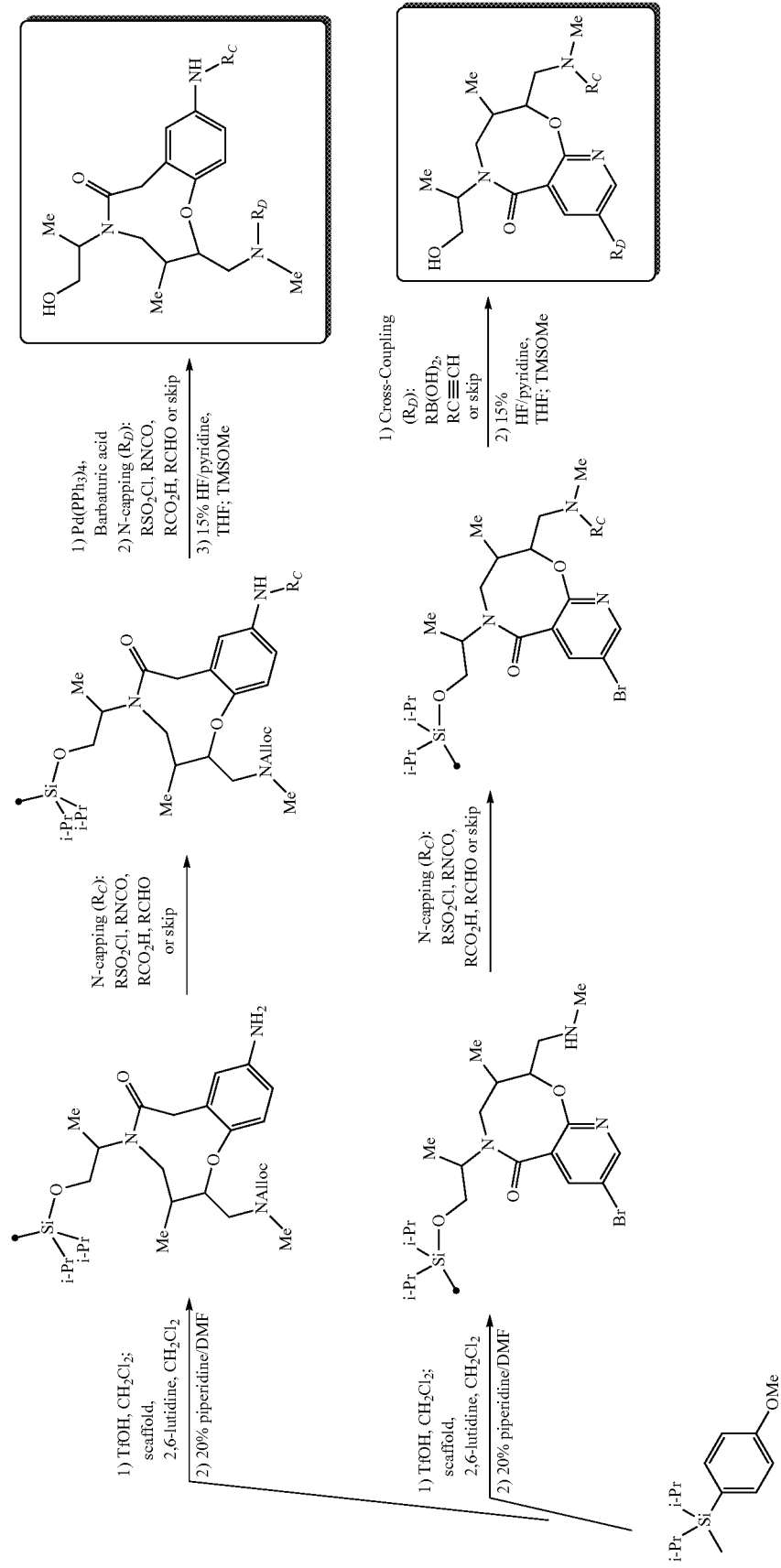
Scheme 2. Synthesis of intermediates and final compounds.

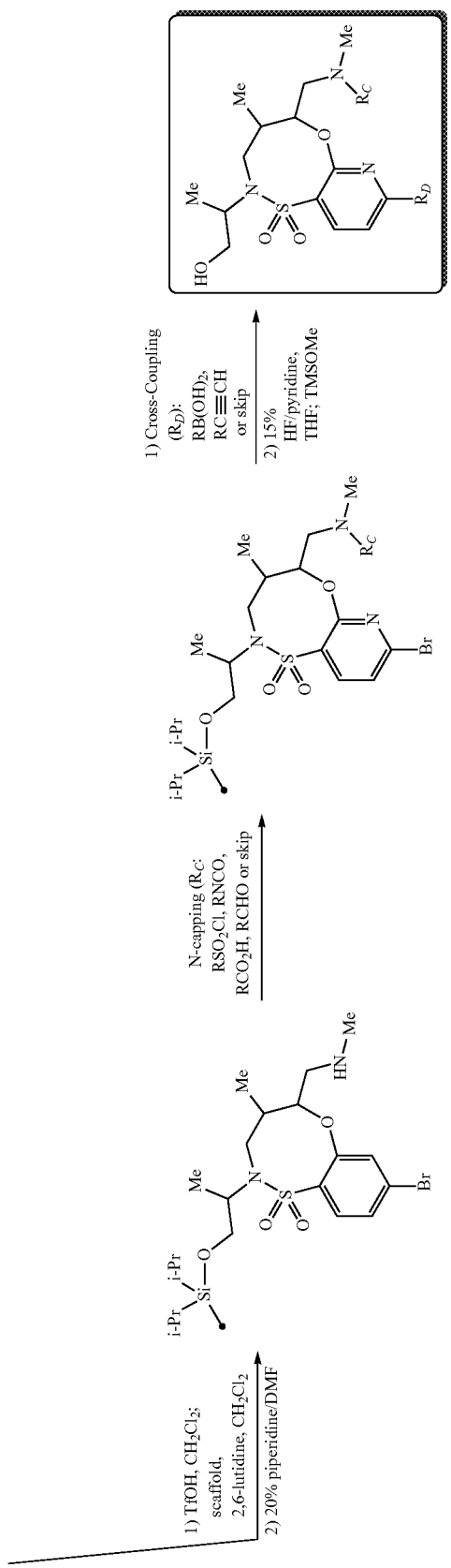

The compounds shown in the synthetic route (Scheme 2), intermediates and final compounds were synthesized using a procedure similar to that reported in Marcaurelle, L. A. et al., J. Am. Chem. Soc. 2010, 132, 16962-16976.

Abbreviations

Abbreviations which may appear in the synthetic schemes and examples are:
Ac for acetyl;
Alloc for allyloxycarbonyl;
Boc for tert-butoxycarbonyl;
DCM for dichloromethane;
DMF for dimethyl formamide;
DMSO for dimethyl sulfoxide;
EtOAc for ethyl acetate;
iPr for isopropyl;
IPA for isopropyl alcohol;
MeOH for methanol;
TEA for triethylamine; and
TFA for trifluoroacetic acid.

The invention further provides methods for the prevention or treatment of diseases or conditions involving aberrant proliferation, differentiation or survival of cells. The invention relates to the treatment of cell proliferative disease, such as cancer, by the administration of a compound of Formula I-V to a patient in need thereof.

In a preferred embodiment, the cancer is selected from glioma, acute myeloid leukemia (AML), Burkitt's leukemia/lymphoma (B-ALL), melanoma and prostate carcinoma. In a preferred embodiment, the disease is selected from Grade I, II, III or IV glioma. In a preferred embodiment, the disease is selected from astrocytomas, oligodendrogliomas, ependymomas and glioblastoma multiforme (GBM).

The invention further relates to a method of treating a disease related to a defect in isocitrate dehydrogenase comprising the step of administering a compound according to any of the above claims to a patient in need thereof, in particular wherein said defect in isocitrate dehydrogenase is a somatic mutation at codon 132 isocitrate dehydrogenase (IDH1) or at codon 172 in isocitrate dehydrogenase 2 (IDH2). The invention further relates to the treatment of Grade I, II, III and IV glioma. The glioma can be selected from astrocytomas, oligodendrogliomas, ependymomas and glioblastoma multiforme (GBM).

The invention further provides methods for the prevention or treatment of diseases related to defects in isocitrate dehydrogenase (IDH1 or IDH2) by administration of a compound of Formula I-III. The invention relates to diseases associated with somatic mutations at codon 132 isocitrate dehydrogenase (IDH1), and at codon 172 and 140 in isocitrate dehydrogenase 2 (IDH2). The invention further relates to the treatment of patients with one more mutations at codons 132 of IDH1 and 172 or 140 of IDH2. The invention further relates to the treatment of diseases associated with mutations to IDH1 selected from R132H, R132C, R132S, R132L, and R132G. The invention further relates to treatment of diseases associated with mutations to 1DH2 selected from R172M, R172G, R172K and R140Q. In one embodiment, the disease associated with the above mentioned mutations is a cell proliferative disease, in particular cancer. In a preferred embodiment, the cell proliferative disease is selected from glioma, acute myeloid leukemia (AML), Burkitt's leukemia/lymphoma (B-ALL), melanoma and prostate carcinoma. In a preferred embodiment, the disease is selected from Grade I, II, III or IV glioma. In a preferred embodiment, the disease is selected from astrocytomas, oligodendrogliomas, ependymomas and glioblastoma multiforme (GBM).

In one embodiment, the invention relates to the inhibition of IDH1/2 by administration of a compound of Formula I-V. In one embodiment, the compound of Formula I-V inhibits the wild type IDH1. In one embodiment, the compound of Formula I-V inhibits wild type IDH2.

In one embodiment, the invention relates to the administration of a compound of Formula I-V in patient that exhibit abnormal 2-hydroxyglutarate (2-HG) production. In one embodiment, the patient exhibit an increase in 2-HG production of more than about 20 fold, or more than about 40 fold or more than about 50 fold or more than about 100 fold or more than about 200 fold compared to normal tissue. The increased 2-HG production can be localized to tumor tissue. In one embodiment, the abnormal 2-HG production is due to a mutation in 1DH1 or 1DH2.

In one embodiment, the invention relates to a method of treating a disease related to a defect in isocitrate dehydrogenase comprising the step of administering a compound according to a compound of Formula I-V to a patient in need thereof, wherein the compound selectively inhibit mutant of IDH1 or a mutant of IDH2 over the respective wild type IDH. In one embodiment, a compound of Formula I-V selectively inhibits a mutant of IDH1 over the wild type IDH1. In one embodiment, the ratio of inhibitory activity against an IDH1 mutant over the wild type IDH1 is about 2 to about 1000, preferably about 5 to about 500, preferably about 10 to about 100, preferably about 25 to about 100. In one embodiment, the mutation to IDH1 is selected from R132H, R132C, R132S, R132L, and R132G. In one embodiment, a compound of Formula I-V selectively inhibits a mutant of IDH2 over the wild type IDH2. In one embodiment, the ratio of inhibitory activity against an IDH2 mutant over the wild type IDH2 is about 2 to about 1000, preferably about 5 to about 500, preferably about 10 to about 100, preferably about 25 to about 100. In one embodiment, the mutation to IDH2 is selected from R172M, R172G, R172K and R140Q.

The invention further relates to the use of a compound of Formula I in the manufacture of a medicament. The invention further relates to the use of a compound of Formula I for the treatment of a cell proliferative disease and the use of a compound of Formula I in the manufacture of a medicament for the treatment of a cell proliferative disease.

In one embodiment, the invention relates to the administration of a compound of Formula I-V in combination with a second pharmacological agent for the treatment of a cell proliferative disease. In one embodiment, the second pharmacological agent is selected from vatalanib (PTK-787/ZK222584), SU-5416, SU-6668, SU-11248, SU-14813, AZD-6474, AZD-2171, CP-547632, CEP-7055, AG-013736, IM-842 or GW-786034, gefitinib, erlotinib, HKI-272, CI-1033 or GW-2016, iressa (ZD-1839), tarceva (OSI-774), PKI-166, EKB-569, herceptin, BAY-43-9006, BAY-57-9006, atrasentan, rituximab, cetuximab, bevacizumab, bivatuzumab mertansine, IMC-1C11, erbitux (C-225), DC-101, EMD-72000, vitaxin, imatinib or dasatinib, VEGFtrap, melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, propamidine or stilbamidine, an anthramycin, an aziridine, a nitrosourea or a derivative thereof, cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, a histonedeacetylase inhibitor such as SAHA, MD-275, trichostatin A, CBHA, LAQ824, or valproic acid, an anti-cancer drug from plants such as paclitaxel (taxol), docetaxel or taxotere, navelbine, vinblastin, vincristin, vindesine, vinorelbine, colchicine or a derivative thereof, maytansine, an ansamitocin or rhizoxin, phomopsin, dolastatin, an epipodophyllotoxin or a derivative of podophyllotoxin, etoposide, teniposide, a steganacin, combretastatin, amphetinile, procarbazine, bortezomib, asparaginase, pegylated asparaginase (pegaspargase), a thymidine-phosphorylase inhibitor, a gestagen, an estrogen, estramustine (T-66), megestrol, an anti-androgen, flutamide, casodex, anandron or cyproterone acetate, aminogluthetimide, anastrozole, formestan, exemestane, letrozole, leuprorelin, buserelin, goserelin, triptorelin, an anti-estrogen, tamoxifen or its citrate salt, droloxifene, trioxifene, raloxifene, zindoxifene, an estrogen receptor antagonist such as fulvestrant, a derivative of 17.beta.-estradiol, ICI 164,384, ICI 182,780, aminoglutethimide, formestane, fadrozole, finasteride, ketoconazole, a LH-RH antagonist, leuprolide, a steroid, prednisone, prednisolone, methylprednisolone, dexamethasone, budenoside, fluocortolone, triamcinolone, interferon.beta., IL-10, IL-12, an anti-TNF.alpha. antibody, etanercept, TNF-.alpha. (tasonermin), thalidomide and its R- and S-enantiomers and its derivatives, revimid (CC-5013), a leukotrien antagonist, mitomycin C, BMY-42355, AZQ or EO-9, a 2-nitroimidazole misonidazole, NLP-1 or NLA-1, a nitroacridine, a nitroquinoline, a nitropyrazoloacridine, RSU-1069, RB-6145, CB-1954, nitromin, an anti-CD3 or anti-CD25 antibody, a tolerance induction agent, minodronic acid and its derivatives (YM-529, Ono-5920, YH-529), zoledronic acid monohydrate, ibandronate sodium hydrate, clodronate disodium, metronidazole, misonidazole, benznidazole, nimorazole, RSU-1069, SR-4233, bromodeoxyuridine, iododeoxyuridine, WR-2721, porfimer, photofrin, a benzoporphyrin derivative, a pheophorbide derivative, merocyanin 540 (MC-540), tin etioporpurin, an anti-template, an anti-sense RNA or DNA, oblimersen, a non-steroidal inflammatory drug, acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam, nimesulide, meloxicam, celecoxib, rofecoxib, a pharmaceutically acceptable salt of a non-steroidal inflammatory drug, a cytotoxic antibiotic, an antibody targeting the surface molecules of cancer cells, apolizumab, 1D09C3, TIMP-1, TIMP-2, Zinc, an inhibitor of oncogenes, P53, R.sup.b, heterocyclic complexes of lanthanides, PUVA, an inhibitor of the transcription factor complex ESX/DRIP130/Sur-2, an inhibitor of HER-2 expression, the heat shock protein HSP90 modulator geldanamycin and its derivative 17-allylaminogeldanamycin or 17-AAG, therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone.

In one embodiment, the invention further provides for the use of one or more compounds of the invention in the manufacture of a medicament for halting or decreasing diseases involving aberrant proliferation, differentiation, or survival of cells. In one embodiment, the invention relates to a method of treating cancer in a subject in need of treatment comprising administering to said subject a therapeutically effective amount of a compound of the invention.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as $(C_1-C_6)$ alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound", "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genito urinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semisolid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

EXAMPLES

Example 1: Synthesis of (4R,5R)-8-(cyclopent-1-en-1-yl)-2-((S)-1-hydroxypropan-2-yl)-4-methyl-5-((methyl(pyridin-3-ylmethyl)amino)methyl)-2,3,4,5-tetrahydrobenzo[b][1,4,5]oxathiazocine 1,1-dioxide

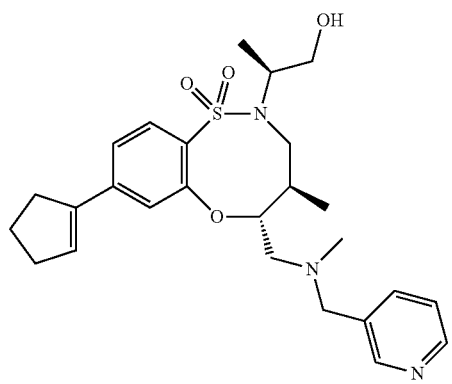 [SMILES: C[C@@H]1CN([C@@H](C)CO)S(=O)(=O)c2ccc(C3=CCCC3)cc2O[C@H]1CN(C)Cc1cccnc1]

Scaffold Loading:

To a flame-dried flask containing silicon-functionalized Lanterns was added a freshly prepared solution of TfOH in anhydrous DCM (9.0 equiv, 5 g of TfOH/100 mL of DCM) was added. Each flask was shaken at RT for 10 min at which time the Lanterns had turned bright orange. The deep red TfOH solution was removed via cannula and anhydrous 2,6-lutidine (12.0 equiv relative to Si) was added. Once the Lantern color had changed from orange to white, (9H-fluoren-9-yl)methyl(((4R,5R)-8-bromo-2-((S)-1-hydroxypropan-2-yl)-4-methyl-1,1-dioxido-2,3,4,5-tetrahydrobenzo[b][1,4,5]oxathiazocin-5-yl)methyl)(methyl)carbamate, the scaffold, (1.2 equiv. relative to Si) was added as a solution in anhydrous DCM (0.4 mL/Lantern) and the reaction mixture was shaken for 48 h overnight. The loading mixture was removed and set aside (to recover any unreacted alcohol) and the Lanterns were washed with the following solvents for 30 min intervals: DCM, THF, 3:1 THF/IPA, 3:1 THF/H$_2$O, DMF, 3:1 THF/H$_2$O, 3:1 THF/IPA, THF, DCM. The Lanterns were then dried on a lyophilizer overnight and carried on to the next step.

Fmoc Removal:

To a flask containing Lanterns was added a solution of 20% piperidine in DMF (0.8 mL/Lantern). After shaking at rt for 30 min, the piperidine solution was removed and the Lanterns were washed with the following solvents for 30 min intervals: DMF, 3:1 THF/H$_2$O, 3:1 THF/IPA, THF, DCM. QC analysis of an aliquot cleaved from the lantern shows no remaining starting material. The Lanterns were then dried on a lyophilizer overnight and carried on to the next step.

N-Capping/Aldehydes:

To a flask containing Lanterns was added DMF with 2% AcOH (0.800 mL/Lantern) followed by 4-pyridinecarboxaldehyde (20 equiv). The reaction mixture was shaken at rt for 1 hr then sodium triacetoxyborohydride (20 equiv) was added and shaking was continued. After 3 days the reaction mixture was removed and the Lanterns were washed with the following solvents for 30 min intervals: DMF, 3:1 THF/H$_2$O, 3:1 THF/IPA, THF, DCM. QC analysis of an aliquot cleaved from the lantern shows no remaining starting material. The Lanterns were then dried on a lyophilizer overnight and carried on to the next step.

Cross-Coupling/Suzuki:

To each flask containing Lanterns was added ethanol (0.800 mL/Lantern) followed by cyclopent-1-en-1-ylboronic acid (20 equiv), triethylamine (40 equiv) and Pd(PPh$_3$)$_2$Cl$_2$ (1 equiv). The resulting mixture was degassed with a stream of N$_2$ before shaking at 60° C. After 4 days, the reaction mixture was removed and the Lanterns were washed with following solvents for 30 min intervals: DCM, DMF, NaCN solution (0.1M) in 1:1 THF/H$_2$O, DMF, 3:1 THF/H$_2$O, 3:1 THF/IPA, THF, DCM. QC analysis of an aliquot cleaved from the lantern shows no remaining starting material.

Cleavage Protocol:

To a 96-well plate containing Lanterns was added a 15% solution of HF/pyridine in stabilized THF (350 µL/Lantern). After 2 h the cleavage solution was quenched with TMSOMe (700 µL/Lantern) and the contents of each well were transferred to a pre-weighed 2-mL vial. The Lanterns were washed with an additional 200 µL of stabilized THF (or THF/MeOH) and the solution was transferred to the 2-mL vial. The samples were concentrated on a GENEVAC® solvent evaporation system overnight without heating to afford the title compound (4R,5R)-8-(cyclopent-1-en-1-yl)-2-((S)-1-hydroxypropan-2-yl)-4-methyl-5-((methyl(pyridin-3-ylmethyl)amino)methyl)-2,3,4,5-tetrahydrobenzo[b][1,4,5]oxathiazocine 1,1-dioxide (7.5 mg, 86% yield). LCMS RT 0.81 min, observed [M+1]$^+$485.23, calculated [M+1]$^+$485.245). Loading masses for each alcohol was determined on a FLEXIWEIGH® system.

Example 2: Synthesis of 1-(4-fluorophenyl)-3-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl) urea

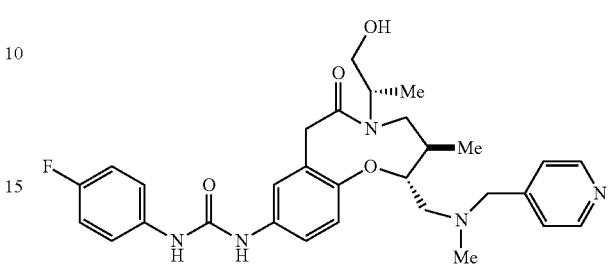

Scaffold Loading:

To a flame-dried flask containing silicon-functionalized Lanterns was added a freshly prepared solution of TfOH in anhydrous DCM (9.0 equiv, 5 g of TfOH/100 mL of DCM) was added. Each flask was shaken at RT for 10 min at which time the Lanterns had turned bright orange. The deep red TfOH solution was removed via cannula and anhydrous 2,6-lutidine (12.0 equiv relative to Si) was added. Once the Lantern color had changed from orange to white, allyl(((2R,3R)-9-((((9H-fluoren-9-yl)methoxy)carbonyl)amino)-5-((S)-1-hydroxypropan-2-yl)-3-methyl-6-oxo-2,3,4,5,6,7-hexahydrobenzo[h][1,5]oxazonin-2-yl)methyl)(methyl) carbamate, the scaffold (1.2 equiv. relative to Si) was added as a solution in anhydrous DCM (0.4 mL/Lantern) and the reaction mixture was shaken for 48 h overnight. The loading mixture was removed and set aside (to recover any unreacted alcohol) and the Lanterns were washed with the following solvents for 30 min intervals: DCM, THF, 3:1 THF/IPA, 3:1 THF/H$_2$O, DMF, 3:1 THF/H$_2$O, 3:1 THF/IPA, THF, DCM. The Lanterns were then dried on a lyophilizer overnight and carried on to the next step.

Fmoc Removal:

To a flask containing Lanterns was added a solution of 20% piperidine in DMF (0.8 mL/Lantern). After shaking at rt for 30 min, the piperidine solution was removed and the Lanterns were washed with the following solvents for 30 min intervals: DMF, 3:1 THF/H$_2$O, 3:1 THF/IPA, THF, DCM. QC analysis of an aliquot cleaved from the lantern shows no remaining starting material. The Lanterns were then dried on a lyophilizer overnight and carried on to the next step.

N-Capping/Isocyanates:

To a flask containing Lanterns was added DCM (0.8 mL/Lantern) followed by 4-fluorophenyl isocyanate (15 equiv). The Lanterns were shaken at rt overnight and then washed with the following solvents for 30 min intervals: DCM, DMF, 3:1 THF/H$_2$O, 3:1 THF/IPA, THF, DCM. QC analysis of an aliquot cleaved from the lantern shows no remaining starting material (a stereoisomer is shown). The Lanterns were then dried on a lyophilizer overnight and carried on to the next step.

Alloc Removal:

To the reaction vessel containing Lanterns, THF (0.8 mL/Lantern) was added, followed by Pd(PPh$_3$)$_4$ (1 equiv) and 1,3-dimethylbarbituric acid (30 equiv). The flask was sealed and shaken at rt for 1 day. The reaction mixture was removed and the Lanterns were washed with DMF until the washings were clear (without any yellow color). Subsequently the Lanterns were washed with the following solvents for 30 min intervals: 3:1 THF/H$_2$O, 3:1 THF/IPA, THF, DCM. QC analysis of an aliquot cleaved from the lantern shows no remaining starting material. The Lanterns were then dried on a lyophilizer overnight and carried on to the next step.

N-Capping/Aldehydes:

To a flask containing Lanterns was added DMF with 2% AcOH (0.800 mL/Lantern) followed by 4-pyridinecarboxaldehyde (20 equiv). The reaction mixture was shaken at rt for 1 hr then sodium triacetoxyborohydride (20 equiv) was added and shaking was continued. After 3 days the reaction mixture was removed and the Lanterns were washed with the following solvents for 30 min intervals: DMF, 3:1 THF/H$_2$O, 3:1 THF/IPA, THF, DCM. QC analysis of an aliquot cleaved from the lantern shows no remaining starting material.

Cleavage Protocol:

To a 96-well plate containing Lanterns was added a 15% solution of HF/pyridine in stabilized THF (350 µL/Lantern). After 2 h the cleavage solution was quenched with TMSOMe (700 µL/Lantern) and the contents of each well were transferred to a pre-weighed 2-mL vial. The Lanterns were washed with an additional 200 µL of stabilized THF (or THF/MeOH) and the solution was transferred to the 2-mL vial. The samples were concentrated on a GENEVAC® solvent evaporation system overnight without heating to afford the title compound 1-(4-fluorophenyl)-3-((2R,3R)-5-((S)-1-hydroxypropan-2-yl)-3-methyl-2-((methyl(pyridin-4-ylmethyl)amino)methyl)-6-oxo-2,3,4,5,6,7-hexahydrobenzo[h][1,5]oxazonin-9-yl)urea (7.5 mg, 84% yield). LCMS RT 0.69 min, observed [M+1]$^+$ 549.28, calculated [M+1]$^+$ 549.28). Loading masses for each alcohol was determined on a FLEXIWEIGH® system.

Example 3: Synthesis of (4R,5R)-2-((S)-1-hydroxypropan-2-yl)-4-methyl-5-((methyl(pyridin-3-ylmethyl)amino)methyl)-8-phenyl-2,3,4,5-tetrahydrobenzo[b][1,4,5]oxathiazocine 1,1-dioxide Scaffold Loading:

To a flame-dried flask containing silicon-functionalized Lanterns was added a freshly prepared solution of TfOH in anhydrous DCM (9.0 equiv, 5 g of TfOH/100 mL of DCM) was added. Each flask was shaken at RT for 10 min at which time the Lanterns had turned bright orange. The deep red TfOH solution was removed via cannula and anhydrous 2,6-lutidine (12.0 equiv relative to Si) was added. Once the Lantern color had changed from orange to white, (9H-fluoren-9-yl)methyl(((4R,5R)-8-bromo-2-((S)-1-hydroxypropan-2-yl)-4-methyl-1,1-dioxido-2,3,4,5-tetrahydrobenzo[b][1,4,5]oxathiazocin-5-yl)methyl)(methyl)carbamate, the scaffold (1.2 equiv. relative to Si) was added as a solution in anhydrous DCM (0.4 mL/Lantern) and the reaction mixture was shaken for 48 h overnight. The loading mixture was removed and set aside (to recover any unreacted alcohol) and the Lanterns were washed with the following solvents for 30 min intervals: DCM, THF, 3:1 THF/IPA, 3:1 THF/H$_2$O, DMF, 3:1 THF/H$_2$O, 3:1 THF/IPA, THF, DCM. The Lanterns were then dried on a lyophilizer overnight and carried on to the next step.

Fmoc Removal:

To a flask containing Lanterns was added a solution of 20% piperidine in DMF (0.8 mL/Lantern). After shaking at rt for 30 min, the piperidine solution was removed and the Lanterns were washed with the following solvents for 30 min intervals: DMF, 3:1 THF/H$_2$O, 3:1 THF/IPA, THF, DCM. QC analysis of an aliquot cleaved from the lantern shows no remaining starting material. The Lanterns were then dried on a lyophilizer overnight and carried on to the next step.

N-Capping/Aldehydes:

To a flask containing Lanterns was added DMF with 2% AcOH (0.800 mL/Lantern) followed by 4-pyridinecarboxaldehyde (20 equiv). The reaction mixture was shaken at rt for 1 hr then sodium triacetoxyborohydride (20 equiv) was added and shaking was continued. After 3 days the reaction mixture was removed and the Lanterns were washed with the following solvents for 30 min intervals: DMF, 3:1 THF/H$_2$O, 3:1 THF/IPA, THF, DCM. QC analysis of an aliquot cleaved from the lantern shows no remaining starting material. The Lanterns were then dried on a lyophilizer overnight and carried on to the next step.

Cross-Coupling/Suzuki:

To each flask containing Lanterns was added ethanol (0.800 mL/Lantern) followed by phenylboronic acid (20 equiv), triethylamine (40 equiv) and Pd(PPh$_3$)$_2$Cl$_2$ (1 equiv). The resulting mixture was degassed with a stream of N$_2$ before shaking at 60° C. After 4 days, the reaction mixture was removed and the Lanterns were washed with following solvents for 30 min intervals: DCM, DMF, NaCN solution (0.1M) in 1:1 THF/H$_2$O, DMF, 3:1 THF/H$_2$O, 3:1 THF/IPA, THF, DCM. QC analysis of an aliquot cleaved from the lantern shows no remaining starting material.

Cleavage Protocol:

To a 96-well plate containing Lanterns was added a 15% solution of HF/pyridine in stabilized THF (350 µL/Lantern). After 2 h the cleavage solution was quenched with TMSOMe (700 µL/Lantern) and the contents of each well were transferred to a pre-weighed 2-mL vial. The Lanterns were washed with an additional 200 µL of stabilized THF (or THF/MeOH) and the solution was transferred to the 2-mL vial. The samples were concentrated on a GENEVAC® solvent evaporation system overnight without heating to afford the title compound (4R,5R)-2-((S)-1-hydroxypropan-2-yl)-4-methyl-5-((methyl(pyridin-3-ylmethyl)amino)methyl)-8-phenyl-2,3,4,5-tetrahydrobenzo[b][1,4,5]oxathiazocine 1,1-dioxide (3.1 mg, 31% yield). LCMS RT 0.78 min, observed [M+1]$^+$ 495.22, calculated [M+1]$^+$ 495.22). Loading masses for each alcohol was determined on a FLEXIWEIGH® system.

Compounds 1-53 were synthesized following similar procedure as above. The synthetic characterization data (LCMS) for Compounds 1-53 is given in Table 2.

TABLE 2

| Compound No. | Observed [M + 1]$^+$ | Expected (M + H)$^+$ |
| --- | --- | --- |
| 1. | 485.23 | 485.235 |
| 2. | 549.28 | 549.275 |
| 3. | 495.22 | 495.219 |
| 4. | 553.26 | 553.261 |
| 5. | 537.33 | 537.332 |
| 6. | 527.25 | 527.245 |
| 7. | 559.23 | 559.225 |
| 8. | 483.22 | 483.219 |
| 9. | 509.23 | 509.235 |
| 10. | 485.23 | 485.235 |
| 11. | 527.25 | 527.245 |
| 12. | 499.25 | 499.25 |
| 13. | 485.23 | 485.235 |
| 14. | 522.32 | 522.321 |
| 15. | 551.34 | 551.336 |
| 16. | 509.23 | 509.235 |
| 17. | 487.26 | 487.258 |
| 18. | 568.26 | 568.261 |

TABLE 2-continued

| Compound No. | Observed [M + 1]+ | Expected (M + H)+ |
|---|---|---|
| 19. | 499.21 | 499.214 |
| 20. | 527.25 | 527.245 |
| 21. | 527.25 | 527.245 |
| 22. | 498.30 | 498.308 |
| 23. | 610.44 | 610.203 |
| 24. | 562.51 | 562.303 |
| 25. | 533.24 | 533.288 |
| 26. | 524.3 | 524.324 |
| 27. | 618.33 | 618.341 |
| 28. | 484.25 | 484.293 |
| 29. | 566.45 | 566.253 |
| 30. | 552.72 | 552.355 |
| 31. | 532.26 | 532.292 |
| 32. | 582.56 | 582.308 |
| 33. | 600.50 | 600.280 |
| 34. | 576.53 | 576.282 |
| 35. | 551.53 | 551.298 |
| 36. | 481.52 | 481.281 |
| 37. | 518.52 | 518.277 |
| 38. | 550.36 | 550.283 |
| 39. | 586.73 | 586.339 |
| 40. | 557.48 | 557.288 |
| 41. | 610.54 | 610.314 |
| 42. | 615.59 | 615.366 |
| 43. | 572.50 | 572.287 |
| 44. | 556.53 | 556.330 |
| 45. | 572.50 | 572.301 |
| 46. | 539.40 | 539.335 |
| 47. | 588.57 | 588.355 |
| 48. | 527.31 | 527.335 |
| 49. | 635.38 | 635.429 |
| 50. | 658.41 | 658.397 |
| 51. | 695.49 | 695.403 |
| 52. | 522.26 | 522.344 |
| 53. | 672.49 | 672.413 |

Example 4

A biochemical assay to identify small molecules that inhibit the neomorphic activity of purified IDH1-R132H was used to identify compounds of interest. C-terminally His8-tagged IDH1-R132H protein was expressed in the *E. coli* Rosetta strain and purified by metal chelate affinity chromatography. The ability of IDH1-R132H to convert α-KG to 2-HG using NADPH is assayed by measuring consumption of NADPH in a diaphorase-coupled assay. Resazurin is a dark blue reagent that has little intrinsic fluorescence. In the presence of NADPH, Resazurin is reduced by diaphorase to resorufin, which is highly fluorescent with an excitation peak at 579 nm and an emission peak at 584 nm (FIGS. 1A-G).

To validate the above assay, a set of compounds was screened in a multi-well format in duplicate. The average signal-to-background ratio was about 10; the Z' factor ranged from 0.7 to 0.85 and CV was <8% for each of the four plates. The scale-up was *facile* and robust, with an average Z' of about 0.74 for 101 plates, and yielding over hundred hits with >=30% inhibition in both replicates. A more stringent cutoff of >=40% inhibition in both replicates, corresponding to >4 times the sum of the standard deviations of the negative and positive controls, yielded a smaller set.

Figure 2B:
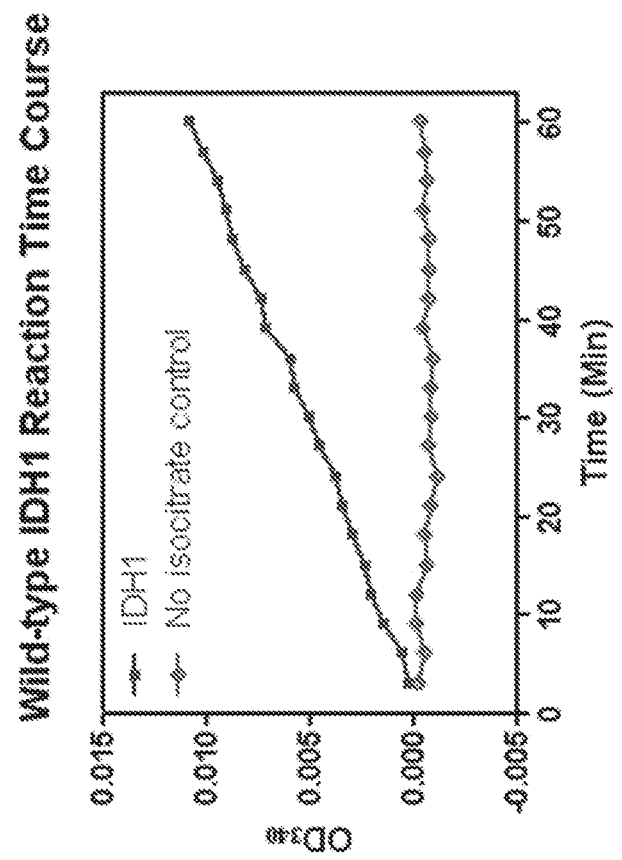
FIG. 2(A-B): Both (A) consumption of NADPH by IDH1-R132H, and (B) production of NADPH by wild-type IDH1 can be monitored by measuring absorbance at 340 nm.
Figure 2A:
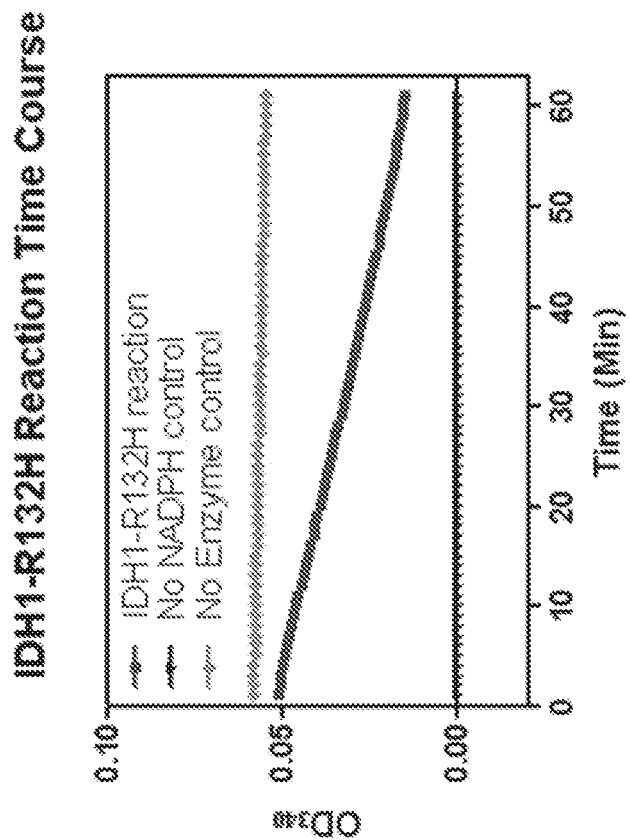

To identify assay artifacts, such as compounds that activate diaphorase directly, another assay was developed as an alternative method to measure the activity of IDH1-R132H based on absorbance at 340 nm by NADPH (FIG. 2A-B). The assay solution contained 100 mM Tris.HCl pH 7.4, 150 mM NaCl, 5 mM MnCl2, 0.03% BSA, 20 uM NADPH, 0.4 mM α-Ketoglutarate and 87 nM of recombinant IDH1-R132H. Absorbance is measured on a SpectraMax spectrophotometer (Molecular Devices) in kinetic mode.

Compound Selectivity Test: To define their selectivity, confirmed inhibitors of IDH1-R132H were tested in dose for their ability to inhibit: (i) wild-type IDH1, (ii) another α-Ketoglutarate-dependent enzyme, the histone demethylase GASC1, and, (iii) another NADP+-dependent dehydrogenase, G6PDH. Selectivity over the following criteria was studied:

(i) wild-type IDH1. The ability of the compound to inhibit IDH1-R132H compared to wild-type IDH1.

(ii, iii) Selectivity over GASC1 and G6PDH. Ideal compounds should not inhibit either GASC1 or G6PDH (IC50 difference >20-fold).

Step Description of Assay Conditions:
1. Dispense 5 µl of compounds to black 1536-well plates using Echo liquid handling system.
2. Dispense 2.5 µl of assay buffer to positive control wells of assay plates using Multidrop Combi dispenser.
3. Dispense 2.5 µl of enzyme mix to assay wells using Multidrop Combi dispenser
4. Incubate at room temperature (about 20-25° C.) for 20 min.
5. Dispense 2.5 µl of substrate mix to initiate the reaction using Multidrop Combi dispenser.
6. Incubate at room temperature for 50 min. Pre-read to identify fluorescent compounds.
7. Dispense 2.5 µl of detection mix using Multidrop Combi dispenser.
8. Incubate at room temperature for 30 min.
9. Read plates on Envision (Ex 535, Em 595).

The activity of Compounds to inhibit IDH1 (wild type) and IDH1-R132H is given in Table 3.

TABLE 3

| Example No. | $IC_{50}$ IDH1 (R132H) | $IC_{50}$ IDH1 (Wild Type) | GASC1 | G6PDH |
|---|---|---|---|---|
| 1 | I | I | ND | IV |
| 2 | I | IV | IV | IV |
| 3 | I | IV | IV | IV |
| 4 | I | IV | ND | IV |
| 5 | I | IV | ND | IV |
| 6 | I | IV | ND | IV |
| 7 | I | IV | ND | IV |
| 8 | I | IV | ND | IV |
| 9 | I | IV | IV | IV |
| 10 | I | IV | ND | IV |
| 11 | III | III | IV | ND |
| 12 | II | IV | IV | IV |
| 13 | III | II | ND | IV |
| 14 | III | IV | IV | IV |
| 15 | II | III | II | IV |
| 16 | II | III | IV | IV |
| 17 | III | IV | I | IV |
| 18 | III | III | ND | ND |
| 19 | II | III | ND | ND |
| 20 | II | IV | IV | IV |
| 21 | III | III | IV | IV |
| 22 | III | IV | ND | IV |
| 23 | II | | ND | ND |
| 24 | I | | ND | ND |
| 25 | I | | ND | ND |
| 26 | I | | ND | ND |
| 27 | I | | ND | ND |
| 28 | III | | ND | ND |
| 29 | II | | ND | ND |
| 30 | I | | ND | ND |
| 31 | I | | ND | ND |
| 32 | III | | ND | ND |
| 33 | II | | ND | ND |
| 34 | I | | ND | ND |

TABLE 3-continued
| Example No. | IC$_{50}$ IDH1 (R132H) | IC$_{50}$ IDH1 (Wild Type) | GASC1 | G6PDH |
|---|---|---|---|---|
| 35 | III | | ND | ND |
| 36 | II | | ND | ND |
| 37 | I | | ND | ND |
| 38 | I | | ND | ND |
| 39 | I | | ND | ND |
| 40 | III | | ND | ND |
| 41 | II | | ND | ND |
| 42 | II | | ND | ND |
| 43 | II | | ND | ND |
| 44 | II | | ND | ND |
| 45 | I | | ND | ND |
| 46 | I | | ND | ND |
| 47 | III | | ND | ND |
| 48 | I | | ND | ND |
| 49 | I | | ND | ND |
| 50 | I | | ND | ND |
| 51 | I | | ND | ND |
| 52 | II | | ND | ND |
| 53 | I | | ND | ND |
Protocol for the Synthesis of Example-52
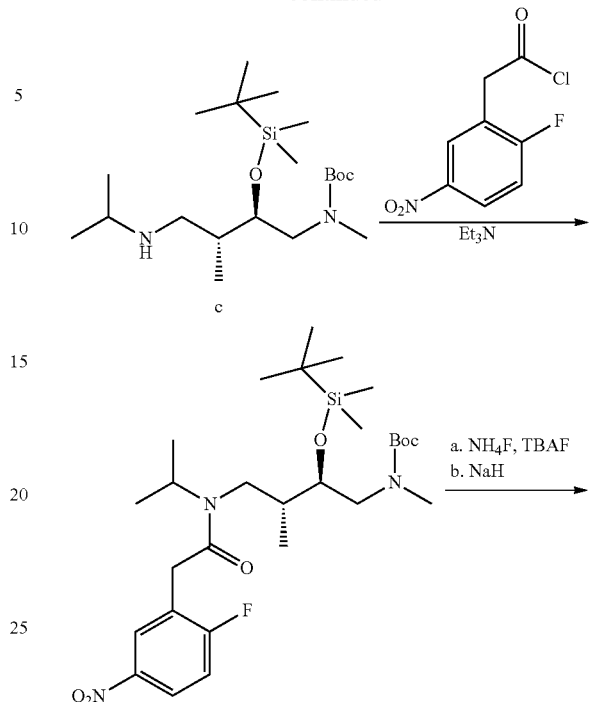
Example-52
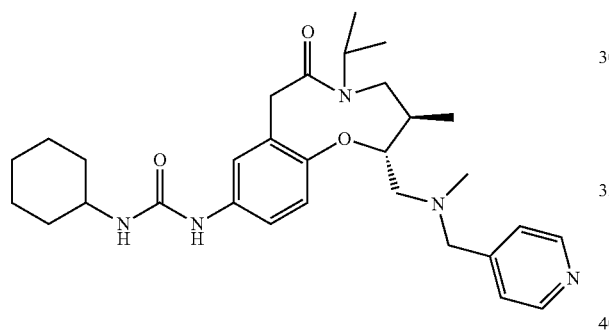
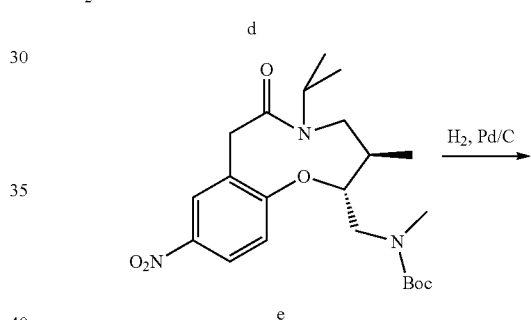
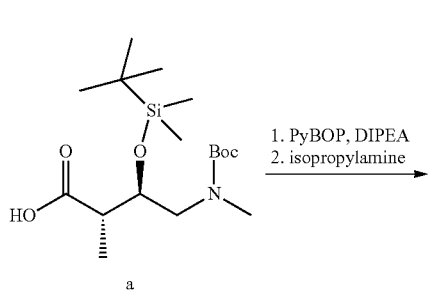
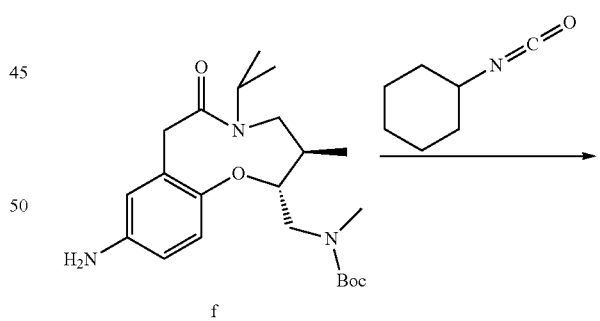
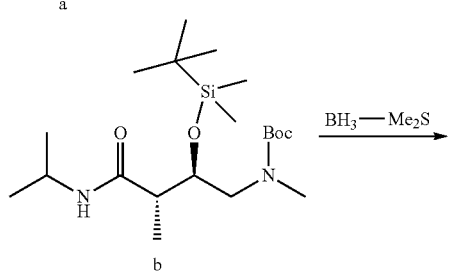
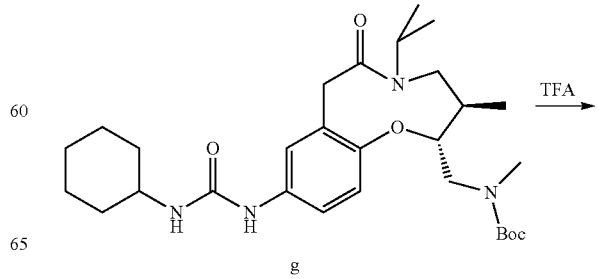

-continued

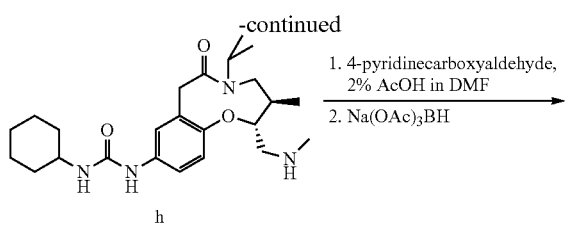
h 1. 4-pyridinecarboxyaldehyde, 2% AcOH in DMF
2. Na(OAc)₃BH

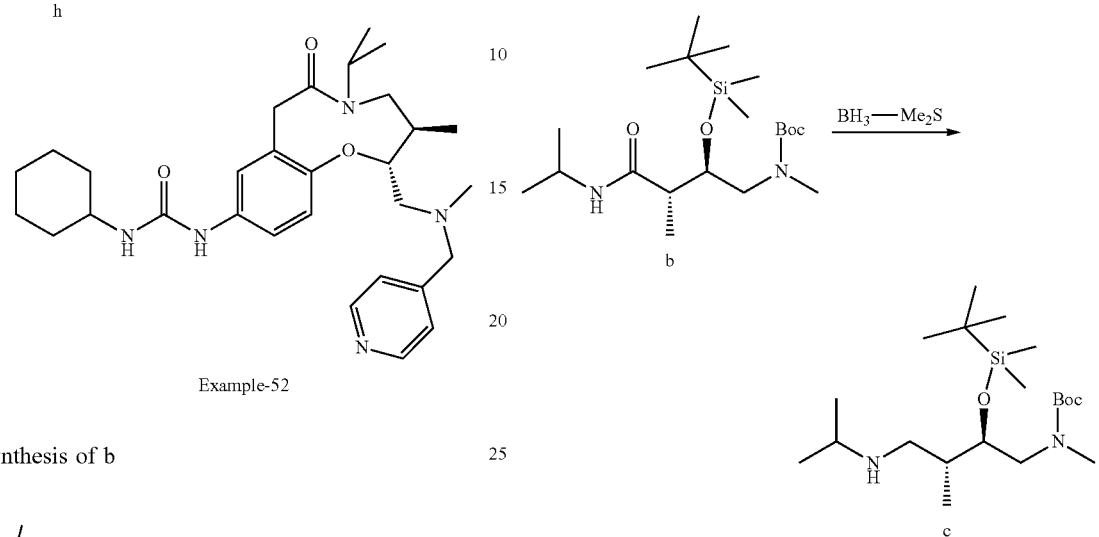

Example-52

Step 1: Synthesis of b

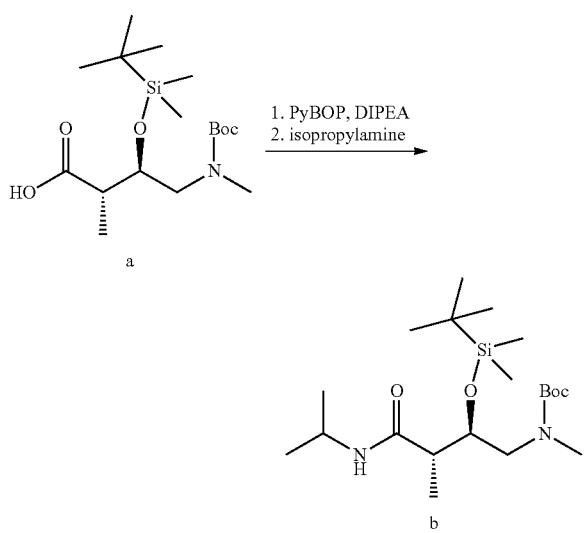
a

1. PyBOP, DIPEA
2. isopropylamine

Compound a was synthesized according to published procedure (Marcaurelle et al. *J. Am. Chem. Soc.* 2010, 132, 16962-16976). The remaining reagents for the following reaction are commercially available. To an oven-dried round-bottom flask equipped with a magnetic stirrer was added a (945 mg, 2.61 mmol, 1.0 equiv) and 10 mL dichloromethane. PyBOP (1.50 g, 2.88 mmol, 1.1 equiv) and diisopropyl ethylamine (1.01 g, 7.84 mmol, 3.0 equiv) were added. The resulting mixture was cooled in an ice bath before isopropylamine (185 mg, 3.14 mmol, 1.2 equiv) was added as a solution in dichloromethane (3 mL) dropwise over 20 minutes. The mixture was stirred for three days at room temperature. The reaction was quenched with water and extracted with dichloromethane. The combined organic extracts were dried over magnesium sulfate, filtered, and concentrated to yield a white solid. The soluble portions of the mixture were taken up in diethyl ether and the insoluble phosphoramide byproducts were removed via filtration. The solvent was removed in vacuo and the crude product was isolated. Flash chromatography on silica gel (0-50% Ethyl acetate in hexanes) gave the product (540 mg, 51%).

Step 2: Synthesis of c

BH₃—Me₂S b c

To an oven-dried 2-necked round-bottom flask equipped with a magnetic stirbar and condenser was added b (530 mg, 1.32 mmol, 1 equiv) in 15 mL tetrahydrofuran (final concentration 0.05 M). Borane-dimethylsulfide complex (500 mg, 5.68 mmol, 5.0 equiv) was added dropwise via syringe and the reaction was heated at 65° C. for 5 hr. The flask was placed on an ice bath and excess hydride was quenched by addition of methanol until bubbling stopped. The mixture was concentrated to an oil and evaporated three times with methanol to remove excess B(OMe)₃. The oil was redissolved in a mixture of aqueous sodium potassium tartrate (10 mL, 0.5 M) and methanol (10 mL) and the resulting slurry was heated at reflux (85° C.) for 12 hours to disrupt the boron-nitrogen complex. Volatiles were removed under reduced pressure and the resulting aqueous mixture was extracted with ethyl acetate. The combined organic extracts were washed once with brine, dried over magnesium sulfate, filtered, and concentrated to provide the desired amine c as a colorless oil in quantitative crude yield (527.6 mg). The material was taken on without purification.

Step 3: Synthesis of d

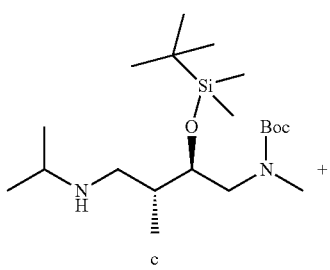
c

-continued

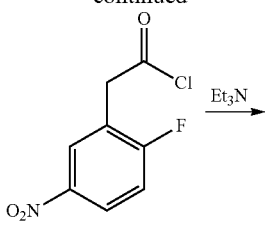

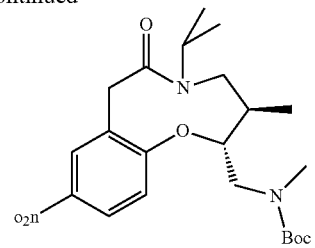

e

To a flame-dried 50 mL flask that had been purged with nitrogen was added ammonium fluoride (171 mg, 4.61 mmol, 5.0 equiv) followed by d (526 mg, 0.922 mmol, 1.0 equiv) in tetrahydrofuran (14 mL, final concentration 0.07 M) and tetrabutylammonium fluoride (1.21 g, 4.61 mmol, 5.0 equiv). The mixture was stirred at room temperature overnight. The reaction was quenched with saturated aqueous ammonium chloride. The organic and aqueous layers were separated and the aqueous layer was extracted with ethyl acetate. The combined organic layers were washed with acetic acid solution (1.0 M in water) and brine and dried over magnesium sulfate. The mixture was filtered and the filtrate was concentrated. Flash chromatography on silica gel (20-60% EtOAc in hexanes) yielded the deprotected alcohol (215 mg). This intermediate was dissolved in THF (15 mL, final concentration 0.03 M) and placed in a flame-dried round-bottom flask with stirbar that had been purged with nitrogen. Sodium hydride (94 mg, 2.36 mmol, 5.0 equiv) was added in one portion and the resulting mixture was allowed to stir overnight at room temperature. The reaction was quenched with not-quite-saturated aqueous ammonium chloride solution. The organic and aqueous layers were separated and the aqueous layer was extracted with ethyl acetate. The combined organic extracts were dried over magnesium sulfate and filtered. The filtrate was concentrated to yield the crude product. Flash chromatography on silica gel (50-70% EtOAc in hexanes) afforded the product as a white crystalline solid (122 mg, 30%).

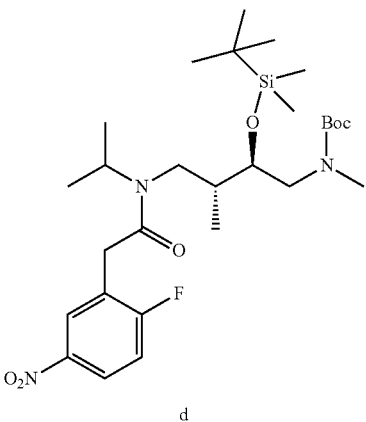

d

To a flame-dried round-bottom flask equipped with stirbar and purged with nitrogen was added c (427 mg, 1.10 mmol, 1.0 equiv) in dichloromethane (final volume 15 mL, concentration 0.04 M). The solution cooled in an ice bath and triethylamine (556 mg, 5.49 mmol, 5.0 equiv) and 2-fluoro-5-nitrophenylacetic acid chloride (598 mg, 2.75 mmol, 2.5 equiv)(prepared as described in Marcuarelle et. al. *J. Am. Chem. Soc.* 2010, 132, 16962-16976) were added via syringe. The reaction mixture took on a dark red-orange color. The vessel was warmed to room temperature and allowed to stir overnight. The reaction was quenched with water and extracted with dichloromethane. The combined organic extracts were dried over magnesium sulfate and concentrated to yield the crude product. The material was purified by flash chromatography on silica gel (0-50% EtOAc in hexanes) to give the product d (526 mg, 84%).

Step 4: Synthesis of e $^1$H NMR (300 MHz, CDCl$_3$, 22° C.) δ 8.18 (d, J=3 Hz, 1H), 8.06 (dd, J=3, 9 Hz, 1H), 7.09 (d, J=9 Hz, 1H), 4.56 (m, 1H), 4.13 (m, 1H), 3.64 (m, 2H), 3.47 (m, 3H), 2.92 (s, 3H), 2.17 (m, 1H), 1.70 (m, 1H), 1.40 (s, 9H), 1.22 (m, 6H), 0.98 (d, J=7 Hz, 3H). $^{13}$C NMR (300 MHz, CDCl$_3$, 22° C.) δ 162.8, 144.0, 131.4, 127.7, 123.9, 123.2, 80.2, 52.3, 51.5, 37.4, 36.2, 28.3, 21.2, 19.8, 15.8.

Step 5: Synthesis of f

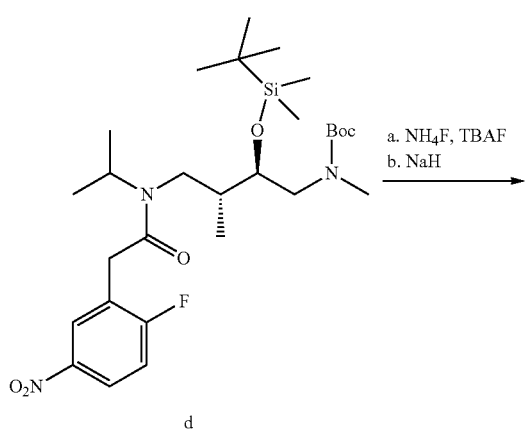

d a. NH$_4$F, TBAF
b. NaH

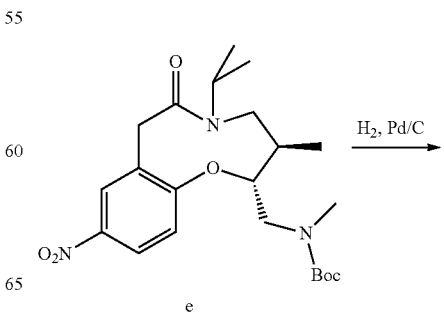

e

H$_2$, Pd/C

-continued

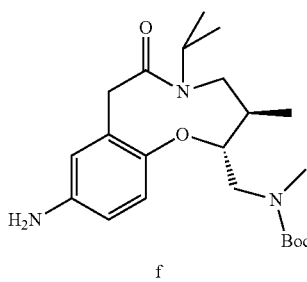

f

Step 7: Synthesis of h

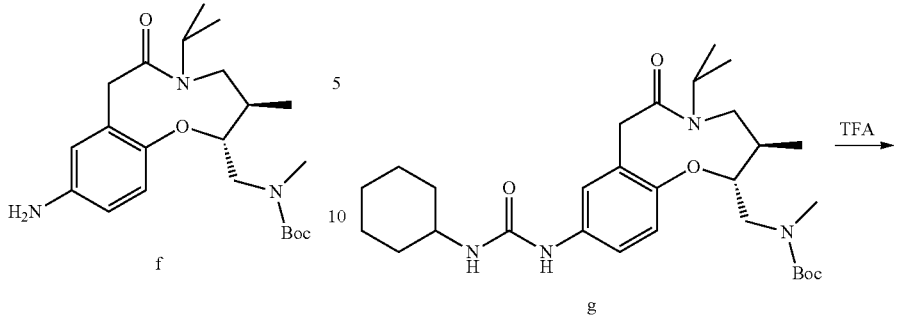

To a flame-dried flask equipped with a stirbar was added 10% palladium on carbon (28.2 mg, 26 µmol, 0.1 equiv), followed by purging of the flask with nitrogen. e (115 mg, 256 µmol, 1.0 equiv) was added as a solution in ethanol (11 mL, final concentration 0.025 M). The mixture was heated to 35° C. and a hydrogen atmosphere was applied via balloon. The reaction was allowed to progress for two hours, after which the mixture was removed from heat and filtered through Celite and the solvent was removed in vacuo to afford the crude product (95 mg, crude yield 88%). The material was taken on crude.

Step 6: Synthesis of g

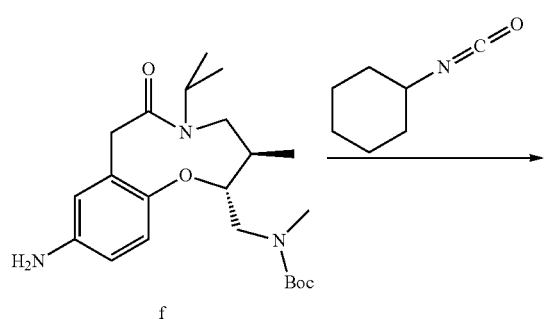

To a small vial equipped with a stirbar was added g (10.4 mg, 20 µmol, 1.0 equiv) in dichloromethane (600 µL, 0.02 M). Trifluoroacetic acid (444 mg, 3.89 mmol, 200 equiv) was added and the mixture was stirred for 30 minutes. The mixture was then concentrated in vacuo and mixed with saturated aqueous sodium bicarbonate. The resulting aqueous mixture was extracted with dichloromethane; the combined organic extracts were dried over sodium sulfate. The solution was decanted and the solvent was removed by evaporation under a stream of dry nitrogen. The material was taken on crude.

Step 8: Synthesis of Example-52

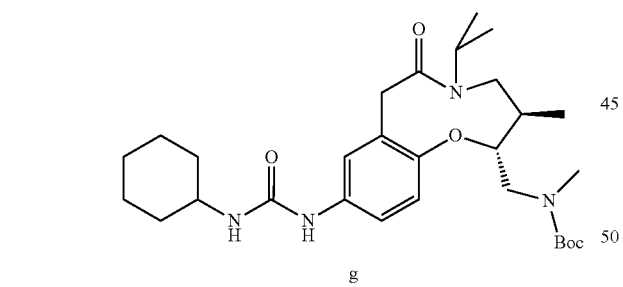

g

To a flame-dried 5 mL flask with stirbar that had been purged with nitrogen was added f (9.2 mg, 23 µmol, 1.0 equiv) and 500 µL dichloromethane. Cyclohexyl isocyanate (12.8 mg, 102 µmol, 4.5 equiv) was added and the mixture was stirred for four days. Extra dichloromethane was periodically added to replace that which evaporated over the course of the reaction. The reaction was quenched with water and extracted with methylene chloride. The combined organic extracts were dried over sodium sulfate; the solution was decanted and concentrated in vacuo to afford crude product. Flash chromatography on silica gel (0-10% MeOH in dichloromethane) provided the product (10.4 mg, 86%).

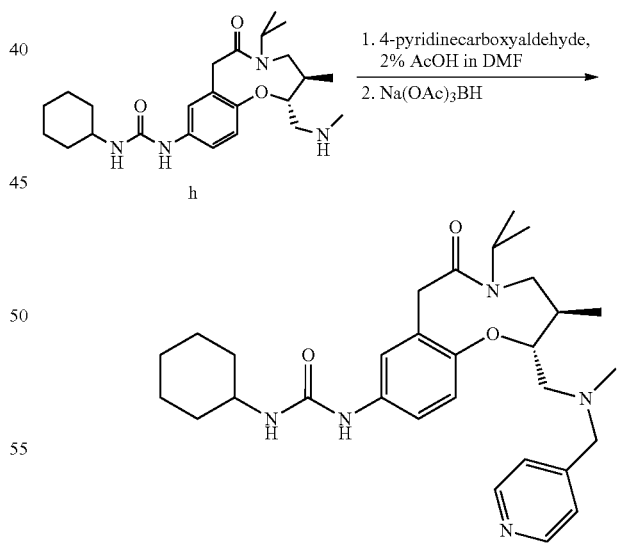

Example-52

To a vial equipped with a stirbar was added 9 (9.6 mg, 22 µmol, 1.0 equiv) dissolved in 2% acetic acid in dimethylformamide (612 µL, 0.036 M). Isonicotinaldehyde (5.7 mg, 53 µmol, 2.4 equiv) was added via syringe and the reaction was allowed to proceed for 90 minutes. Sodium triacetoxyborohydride (9.0 mg, 42 µmol, 1.9 equiv) was added and the mixture was stirred for two days. The solvent was removed in vacuo at 50° C. and the residue was taken up in saturated aqueous sodium bicarbonate solution. The aqueous mixture was extracted with dichloromethane; the combined organic extracts were dried over sodium sulfate. The solution was decanted and concentrated in vacuo. The residue was purified by high-pressure liquid chromatography to yield the product (4.9 mg, 42%).

$^1$H NMR (300 MHz, CDCl$_3$, 22° C.) δ 7.43 (m, 2H), 7.04 (m, 2H), 6.94 (m, 1H), 5.45 (m, 1H), 4.78 (m, 1H), 4.17 (m, 1H), 3.75 (m, 1H), 3.51 (m, 2H), 3.34 (m, 1H), 3.11 (m, 1H), 2.79 (m, 1H), 2.59 (m, 1H), 2.41 (m, 1H), 2.22 (s, 3H), 1.88 (m, 5H), 1.56 (m, 6H), 1.23 (m, 6H), 0.94 (m, 3H).

Synthesis of Example-50

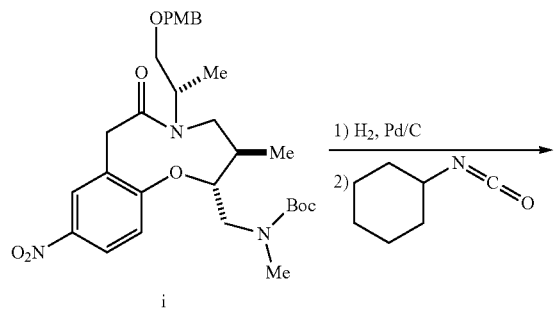

i

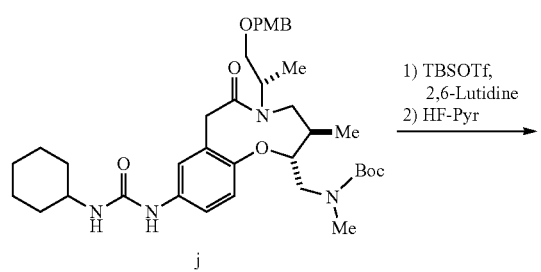

j

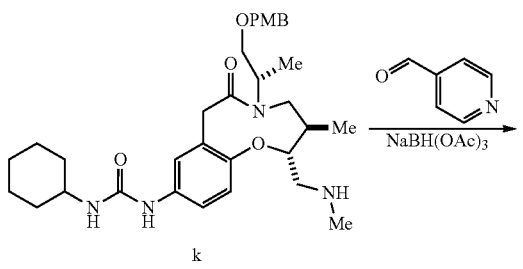

k

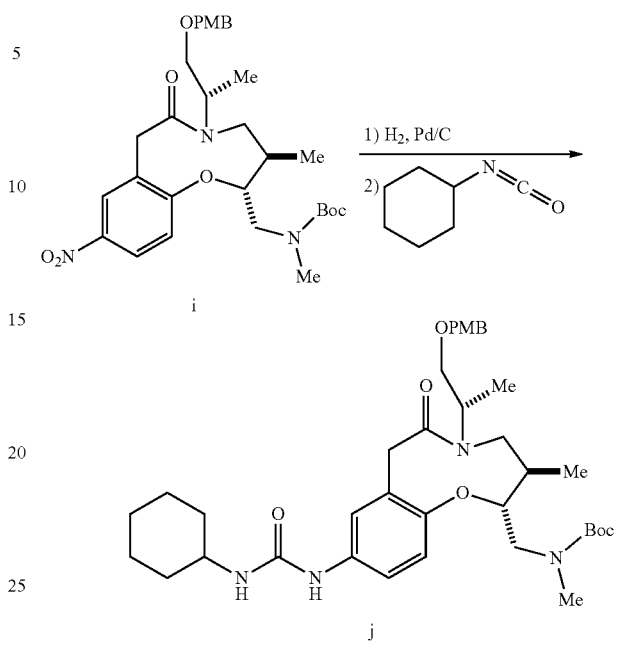

Example-50

Step 1 and 2—Reduction and N-Capping with Isocyanates

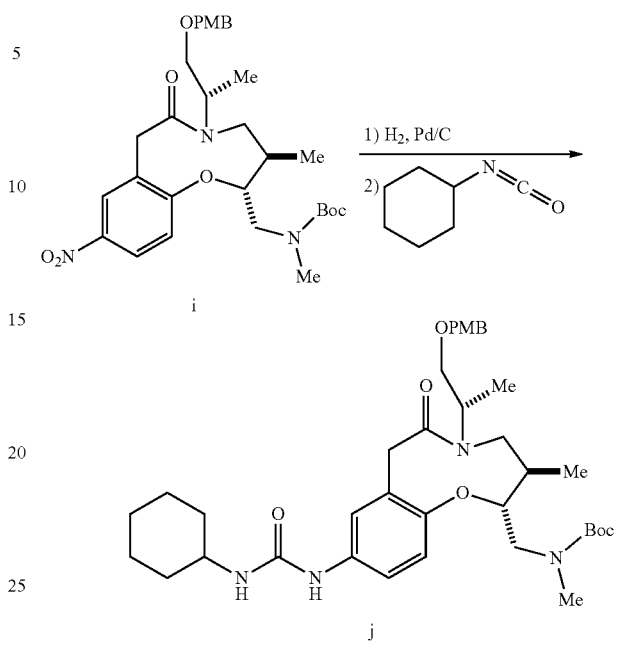

i j

Lactam i (1 equiv.) and palladium (10% on activated carbon, 0.1 equiv.) were stirred in EtOH (25 mM) at 35° C. under a hydrogen atmosphere. The reaction was monitored by LCMS for complete consumption of starting material (1-2 h). The mixture was cooled, filtered through Celite and concentrated to give the aniline derivative j.

The crude product was dried under vacuum and then dissolved in DCM (150 mM) and transferred into a dried round-bottom flask flushed with nitrogen. Cyclohexyl isocyanate (1.5 equiv.) was added with a syringe. It was stirred overnight at room temperature. The mixture was concentrated and the product was isolated by column chromatography (DCM/MeOH gradient from 0 to 20% MeOH). Yield: 96%.

$[α]_D^{20}$=−2.3° (c 1.0, CHCl3). IR (cm$^{-1}$)=3346, 2927, 2853, 2361, 2342, 1692, 1611, 1551, 1497, 1451, 1393, 1365, 1249, 1217, 1149, 1086, 819. $^1$H NMR (300 MHz, CDCl$_3$-d) δ=7.34 (s, 1H), 7.24-7.16 (m, 3H), 6.86 (d, J=8 Hz, 2H), 6.67 (m, 1H), 5.52 (s, 1H), 4.44 (s, 2H), 4.15 (m, 1H), 3.81-3.79 (m, 6H), 3.61-3.59 (m, 4H), 3.36-3.31 (m, 2H), 2.99-2.90 (m, 3H), 2.61 (s, 3H), 2.09 (m, 1H), 1.90 (m, 2H), 1.69-1.55 (m, 4H), 1.43 (s, 9H), 1.35 (d, J=7 Hz, 4H) 1.25 (s, 3H), 0.87-0.83 (m, 3H). $^{13}$C NMR (75 MHz, CDCl$_3$-d) δ=172.3, 159.5, 155.7, 152.5, 136.4, 130.7, 129.6, 124.4, 123.02, 120.0, 114.1, 80.2, 77.6, 73.2, 72.8, 59.2, 55.6, 48.8, 41.4, 38.0, 36.0, 34.1, 34.0, 30.0, 28.8, 26.1, 25.3, 25.2, 23.0, 15.4. HRMS (ESI) calcd for C$_{37}$H$_{54}$N$_4$O$_7$ [M+H]$^+$: 667.3993. Found: 667.843.

Step 3—Boc Removal

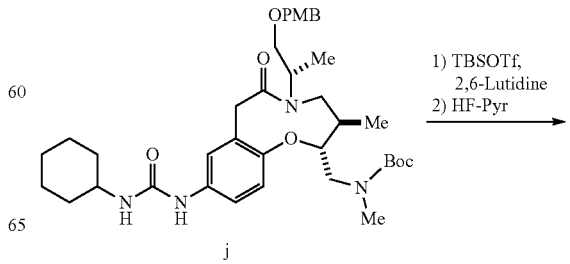

j

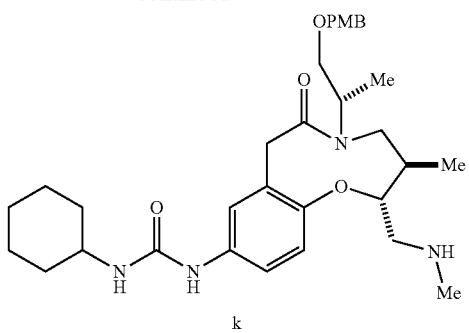

k 2,6-Lutidine (1.26 mL, 10.8 mmol, 4 equiv.) and TBSOTf (1.86 mL, 8.1 mmol, 3 equiv.) were added to a solution of j (1.8 g, 2.7 mmol, 1 equiv.) in DCM (27 mL, 0.1 M) at room temperature and stirred overnight. The reaction was quenched with saturated NH$_4$Cl solution and extracted with EtOAc. The combined organic extracts were dried over MgSO4, filtered, and concentrated to the crude silyl carbamate.

The resulting oil was dissolved in THF (22.5 mL, 1.2 M) and subsequently HF/pyridine (70% HF; 360 uL, 1 equiv. HF) was added. The mixture was stirred for 30 min, quenched with saturated NH$_4$Cl and extracted with EtOAc. The combined organic extracts were dried over MgSO4, filtered, and concentrated. Product k was used without further purification. Yield: 98%.

$[\alpha]_D^{20}$=−25.7° (c 1.0, CHCl3). IR (cm$^{-1}$) 3342, 2927, 2853, 2361, 1610, 1551, 1513, 1498, 1249, 1218, 1085, 1034, 820. $^1$H NMR (300 MHz, CDCl$_3$-d) δ=7.55 (s, 1H), 7.26-7.24 (m, 3H), 6.87 (d, J=8 Hz, 2H) 6.44 (m, 1H), 5.76 (m, 1H), 4.46 (s, 3H), 4.38 (m, 1H), 4.15 (d, J=14 Hz, 1H), 3.86 (m, 5H), 3.59-3.30 (m, 4H), 3.09 (d, J=13 Hz, 1H), 2.81 (d, J=11 Hz, 1H), 2.58-2.35 (m, 6H), 1.91-1.54 (m, 6H), 1.34-0.84 (m, 10H). $^{13}$C NMR (75 MHz, CDCl$_3$-d) δ=172.7, 159.5, 155.9, 151.4, 136.5, 130.8, 130.0, 129.6, 125.0, 123.2, 119.7, 114.1, 89.0, 73.1, 72.7, 55.6, 54.0, 51.9, 48.6, 37.6, 37.4, 34.1, 33.2, 30.0, 26.1, 25.3, 15.6. HRMS (ESI) calcd for C$_{32}$H$_{46}$N$_4$O$_5$ [M+H]$^+$: 567.3468. Found: 567.4246.

Step 4—Reductive Amination

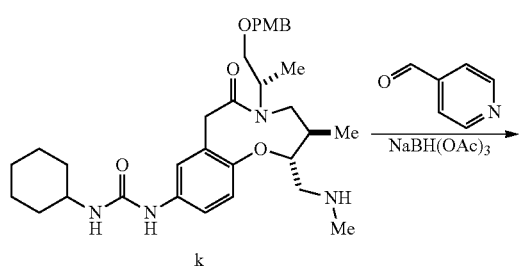

k

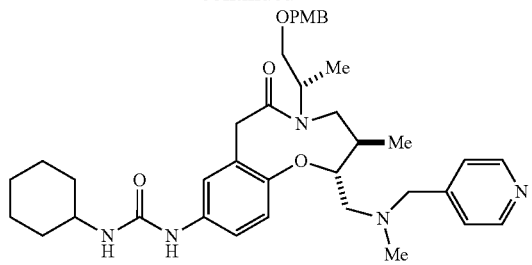

Example-50

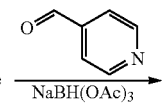

k

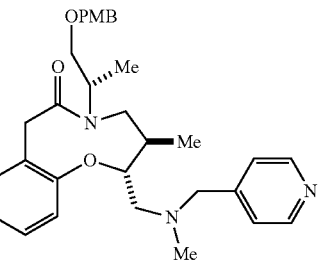

Example-50

Starting material k (0.7 g, 1.24 mmol, 1 equiv.) was diluted in DMF (containing 2% Acetic acid; 88 mM). Isonicotinic aldehyd (0.128 mL, 1.36 mmol, 1.1 equiv.) was added and the mixture was stirred for 1 h at room temperature. Subsequently sodium triacetoxyborohydride (340 mg, 1.61 mmol, 1.3 equiv.) was added and the mixture was stirred for 3 days. The solvents were evaporated in vacuo and product Example-50 was purified by column chromatography (DCM/MeOH gradient from 0 to 20% MeOH). Yield: 93%.

$[\alpha]_D^{20}$=−6.2° (c 1.0, CHCl3). IR (cm$^{-1}$) 3349, 2929, 2852, 1604, 1551, 1497, 1451, 1414, 1248, 1217, 1084, 820. $^1$H NMR (300 MHz, CDCl$_3$-d) δ=8.51 (d, J=5 Hz, 2H), 7.53 (s, 1H), 7.22-7.14 (m, 4H), 6.85 (d, J=8 Hz, 2H), 6.68 (dd, J$_1$=33 Hz, J$_2$=8 Hz, 2H), 5.69 (d, J=8 Hz, 1H), 4.43-4.34 (m, 3H), 4.14 (d, J=13 Hz, 1H), 3.89-3.29 (m, 12H), 3.06 (d, J=11 Hz, 1H), 2.72 (d, J=13 Hz, 1H), 2.53 (d, J=13 Hz, 1H), 2.39 (m, 1H), 2.19 (s, 3H), 1.90-1.53 (m, 6H), 1.33-0.88 (m, 10H). $^{13}$C NMR (75 MHz, CDCl$_3$-d) δ=172.6, 159.5, 155.9, 151.8, 150.1, 149.0, 136.6, 130.7, 130.0, 129.5, 124.6, 124.0, 123.6, 119.5, 114.2, 89.4, 73.1, 72.8, 62.6, 59.2, 55.6, 53.3, 48.7, 44.2, 37.5, 34.6, 34.1, 26.1, 25.2, 15.9, 15.6. HRMS (ESI) calcd for C$_{38}$H$_{51}$N$_5$O$_5$ [M+H]$^+$: 658.3890. Found: 658.3772.

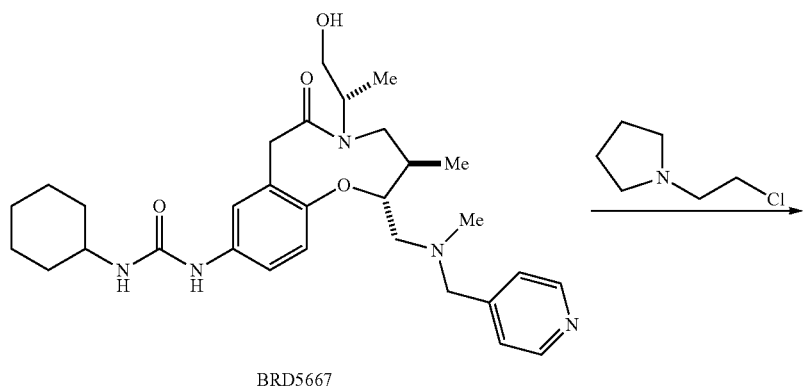
BRD5667
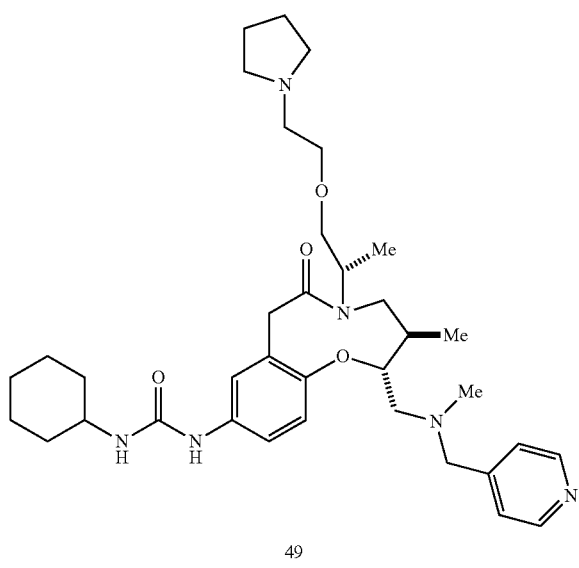
49
To a solution of BRD5667 in DMF (10 mg in 0.372 mL, 50 mM) at room temperature was added sodium hydride (1.3 mg, 0.055 mmol). The mixture was stirred for 10 minutes and 4-(2-chloroethyl)pyrrolidine hydrochloride (4.4 mg, 0.026 mmol) was added to the reaction mixture. The mixture was stirred at 40° C. for 24 h. Yield after HPLC purification: 0.494 mg.
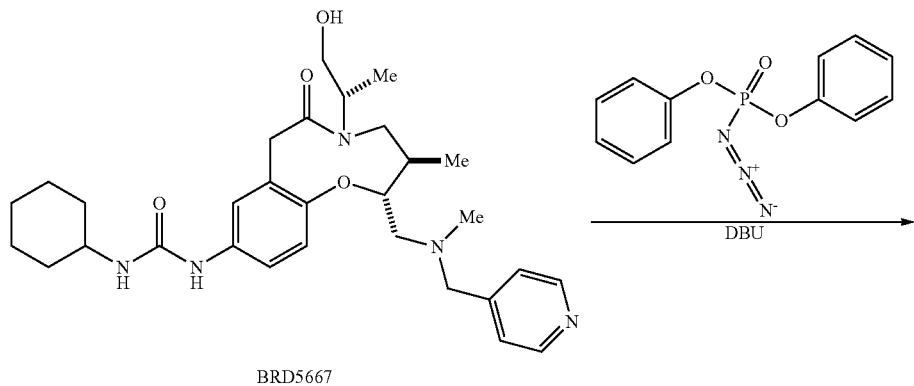
BRD5667

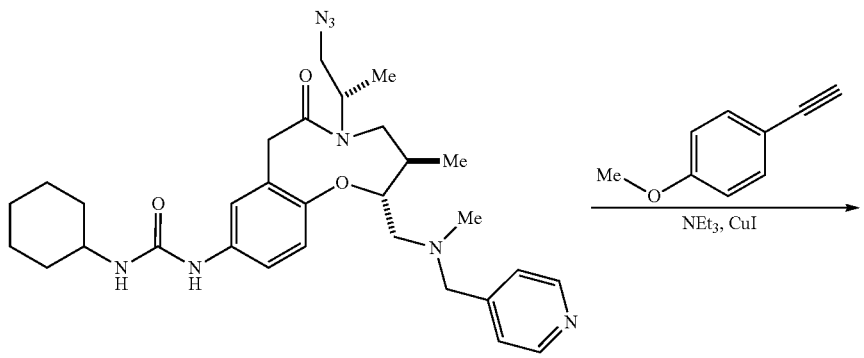

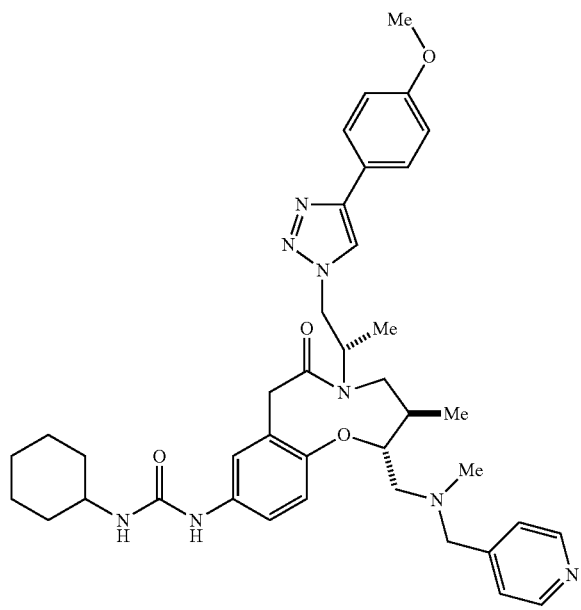

51

BRD5667 was distilled azeotropically three times with 20% dichloromethane in benzene and lyophilized overnight.

To a solution of BRD5667 in anhydrous tetrahydrofuran (83.3 mg in 3.87 mL, 40 mM) under argon was added DBU (0.093 mL, 0.62 mmol) followed by diphenyl phosphorazidate (0.1 mL, 0.465 mmol). The mixture was stirred for 24 h. The solvent was removed under vacuum and the azide was purified by column chromatography (0-20% MeOH in DCM). Yield after purification: 10 mg, 11%.

The azide (10 mg, 0.018 mmol) was diluted in tetrahydrofuran (0.35 mL, 50 mM) in a dried LCMS vial. Triethylamine (10 uL, 0.07 mmol), the alkyne (7 uL, 0.05 mmol), and copper(I) iodide (0.34 mg, 0.0018 mmol) were added. It was stirred overnight at room temperature. After filtration, the solvent was removed and the product was purified by HPLC. Yield after HPLC purification: 0.674 mg.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of Formula (TB) or Formula (IC), or a pharmaceutically acceptable salt thereof:

Formula IB

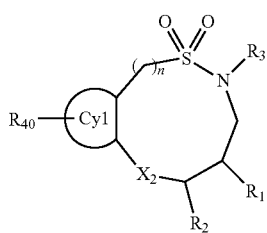

Formula IC

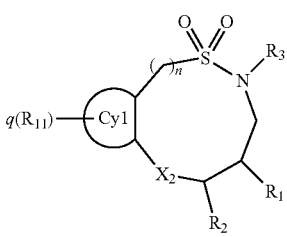

wherein:
n is 0;
q is 1;
$X_2$ is —O—
Cy1 is:

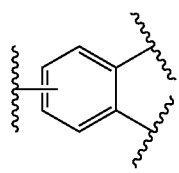

$R_1$ is $C_1$-$C_6$ alkyl;
$R_2$ is:

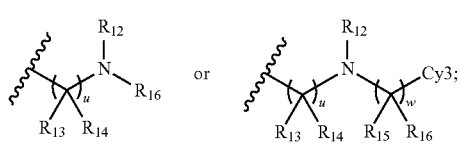

$R_{12}$ is hydrogen, $C_1$-$C_6$ alkyl, substituted $C_1$-$C_6$ alkyl, $CONR_{20}R_{21}$, $C(O)R_{20}$, or $C(O)OR_{21}$;
$R_{13}$, $R_{14}$, and $R_{15}$ are each independently hydrogen;

$R_{16}$ is hydrogen, halogen, aliphatic, substituted aliphatic, aryl, substituted aryl, heteroaryl or substituted heteroaryl;
alternatively, when two of the $R_{13}$, $R_{14}$, $R_{15}$, and $R_{16}$ groups are attached to a carbon atom, together said two groups and said carbon atom may form a carbonyl or an optionally substituted vinyl group;
u is 1;
w is 0, 1, 2, 3, 4, 5 or 6;
Cy3 is optionally substituted cycloalkyl, optionally substituted cycloalkenyl, optionally substituted heterocyclyl, optionally substituted aryl or optionally substituted heteroaryl;
$R_3$ is selected from:

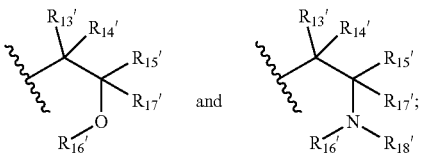

each $R_{13}'$, $R_{14}'$ and $R_{15}'$ is independently hydrogen, $C_1$-$C_6$ alkyl, or substituted $C_1$-$C_6$ alkyl;
each of $R_{16}'$ and $R_{17}'$ is independently hydrogen, $C_1$-$C_6$ alkyl, or substituted $C_1$-$C_6$ alkyl;
$R_{11}$ is:

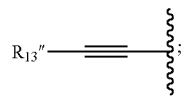

$R_{13}''$ is hydrogen, halogen, —$OR_{20}$, —$SR_{20}$, —$NR_{20}R_{21}$, —$CF_3$, —CN, —$NO_2$, —$N_3$, —$C(O)R_{20}$, —$C(O)OR_{20}$, —$C(O)NR_{20}R_{21}$, acyl, alkoxy, substituted alkoxy, alkylamino, substituted alkylamino, substituted or unsubstituted alkylthio, substituted or unsubstituted alkylsulfonyl, aliphatic, substituted aliphatic, aryl or substituted aryl;
$R_{40}$ is selected from the group consisting of:

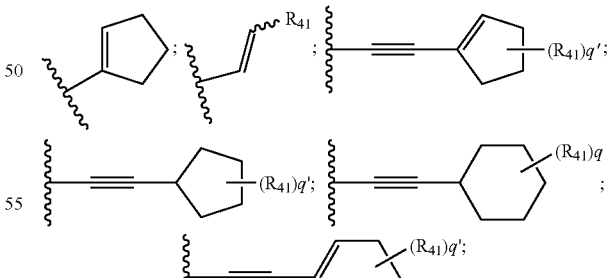

and
$R_{41}$ is hydrogen, halogen, aliphatic, substituted aliphatic, aryl, substituted aryl, —$OR_{20}$, —$SR_{20}$, —$NR_{20}R_{21}$, —$CF_3$, —CN, —$NO_2$, —$N_3$, —$C(O)R_{20}$, —$C(O)OR_{20}$, —$C(O)NR_{20}R_{21}$, acyl, alkoxy, substituted alkoxy, alkylamino, substituted alkylamino, substituted or unsubstituted alkylthio, substituted or unsubstituted alkylsulfonyl;

q' is 1;

and $R_{20}$ and $R_{21}$ are each independently hydrogen, halogen, aliphatic, substituted aliphatic, aryl or substituted aryl.

2. The compound of claim 1, wherein $R_1$ is methyl, ethyl or propyl.

3. The compound of claim 2, wherein $R_1$ is methyl.

4. The compound of claim 1, wherein $R_{12}$ is $C_1$-$C_6$ alkyl or substituted $C_1$-$C_6$ alkyl.

5. The compound of claim 1, wherein $R_2$ is:

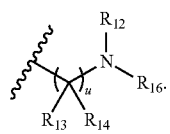

6. The compound of claim 1, wherein $R_3$ is:

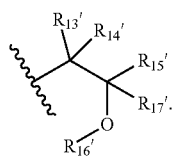

7. The compound of claim 6, wherein $R_3$ is

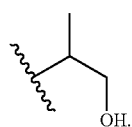

8. The compound of claim 1, wherein $R_{11}$ is a moiety selected from those shown in Table B:

TABLE B

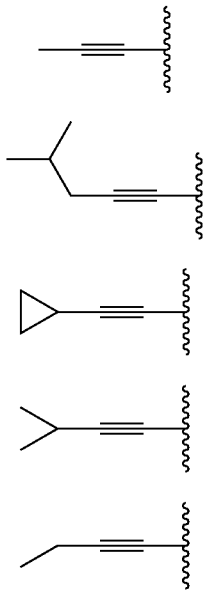

TABLE B-continued

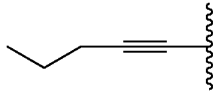

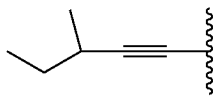 [SMILES: *C#CC(C)CC]

9. The compound of claim 1, wherein w is 0, 1 or 2.

10. The compound of claim 1 selected from those shown in Table 1, or a pharmaceutically acceptable salt thereof:

TABLE 1

1

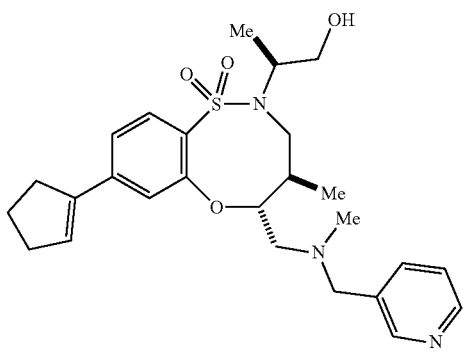 [SMILES: C[C@@H]1CN([C@@H](C)CO)S(=O)(=O)c2ccc(C3=CCCC3)cc2O[C@H]1CN(C)Cc1cccnc1]

(4R,5R)-8-(cyclopent-1-en-1-yl)-2-((S)-1-hydroxypropan-2-yl)-4-methyl-5-((methyl(pyridin-3-ylmethyl)amino)methyl)-2,3,4,5-tetrahydrobenzo[b][1,4,5]oxathiazocine 1,1-dioxide

4

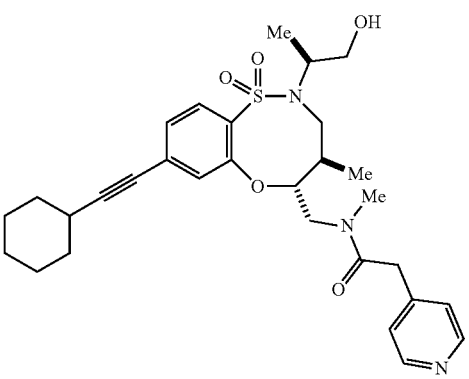 [SMILES: C[C@@H]1CN([C@@H](C)CO)S(=O)(=O)c2ccc(C#CC3CCCCC3)cc2O[C@H]1CN(C)C(=O)Cc1ccncc1]

N-(((4R,5R)-8-(cyclohexylethynyl)-2-((S)-1-hydroxypropan-2-yl)-4-methyl-1,1-dioxido-2,3,4,5-tetrahydrobenzo[b][1,4,5]oxathiazocin-5-yl)methyl)-N-methyl-2-(pyridin-4-yl)acetamide TABLE 1-continued

6

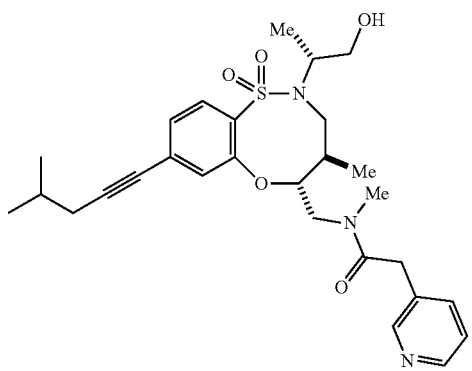 [SMILES: CC(C)CC#Cc1ccc2c(c1)O[C@@H](CN(C)C(=O)Cc1cccnc1)[C@H](C)CN([C@H](C)CO)S2(=O)=O]

N-(((4R,5R)-2-((R)-1-hydroxypropan-2-
yl)-4-methyl-8-(4-methylpent-1-yn-1-yl)-1,1-
dioxido-2,3,4,5-tetrahydrobenzo[b][1,4,5]oxathiazocin-
5-yl)methyl)-N-methyl-2-(pyridin-3-yl)acetamide

8

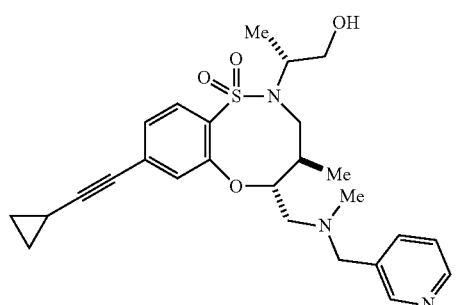

(4R,5R)-8-(cyclopropylethynyl)-2-((R)-1-hydroxypropan-
2-yl)-4-methyl-5-((methyl(pyridin-3-ylmethyl)amino)methyl)-
2,3,4,5-tetrahydrobenzo[b][1,4,5]oxathiazocine
1,1-dioxide

10

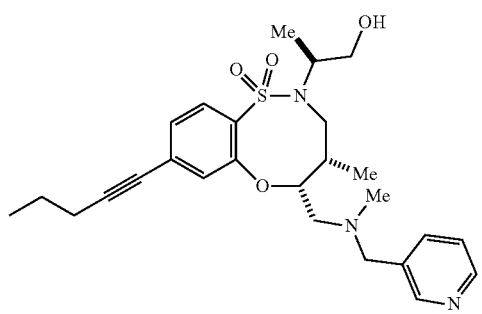 [SMILES: CCCC#Cc1ccc2c(c1)O[C@@H](CN(C)Cc1cccnc1)[C@@H](C)CN([C@@H](C)CO)S2(=O)=O]

(4S,5R)-2-((S)-1-hydroxypropan-2-yl)-4-methyl-5-
((methyl(pyridin-3-ylmethyl)amino)methyl)-8-
(pent-1-yn-1-yl)-2,3,4,5-
tetrahydrobenzo[b][1,4,5]oxathiazocine 1,1-dioxide TABLE 1-continued

11

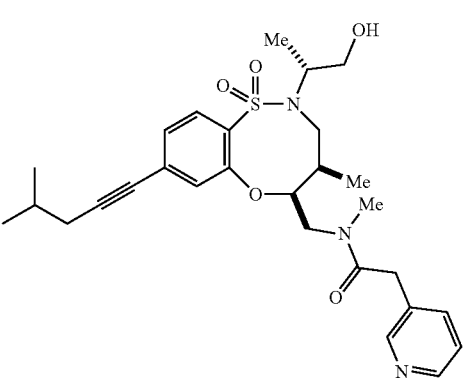 [SMILES: CC(C)CC#Cc1ccc2c(c1)O[C@H](CN(C)C(=O)Cc1cccnc1)[C@H](C)CN([C@H](C)CO)S2(=O)=O]

N-((((4R,5S)-2-((R)-1-hydroxypropan-2-yl)-4-
methyl-8-(4-methylpent-1-yn-1-yl)-1,1-
dioxido-2,3,4,5-tetrahydrobenzo[b][1,4,5]oxathiazocin-
5-yl)methyl)-N-methyl-2-(pyridin-3-yl)acetamide

13

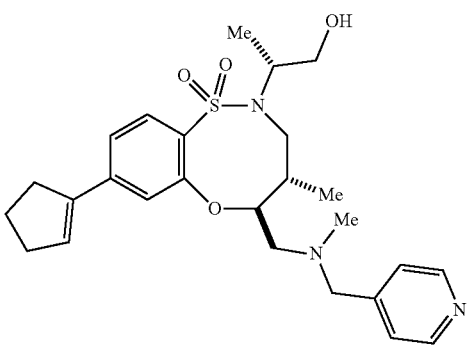 [SMILES: C[C@H](CO)N1C[C@H](C)[C@@H](CN(C)Cc2ccncc2)Oc2cc(C3=CCCC3)ccc2S1(=O)=O]

(4S,5S)-8-(cyclopent-1-en-1-yl)-2-((R)-1-hydroxypropan-
2-yl)-4-methyl-5-((methyl(pyridin-4-ylmethyl)amino)methyl)-
2,3,4,5-tetrahydrobenzo[b][1,4,5]oxathiazocine
1,1-dioxide

18

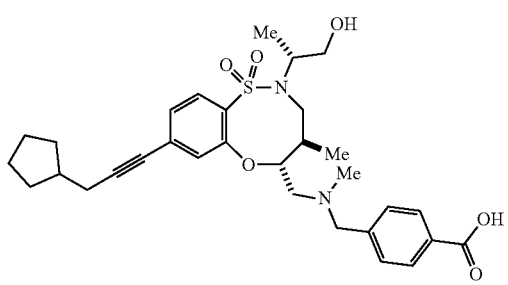 [SMILES: C[C@@H]1CN([C@H](C)CO)S(=O)(=O)c2ccc(C#CCC3CCCC3)cc2O[C@H]1CN(C)Cc1ccc(C(=O)O)cc1]

4-(((((4R,5R)-8-(3-cyclopentylprop-1-yn-1-yl)-
2-((R)-1-hydroxypropan-2-yl)-4-
methyl-1,1-dioxido-2,3,4,5-tetrahydrobenzo[b][1,4,5]
oxathiazocin-5-yl)methyl)(methyl)amino)methyl)
benzoic acid

TABLE 1-continued

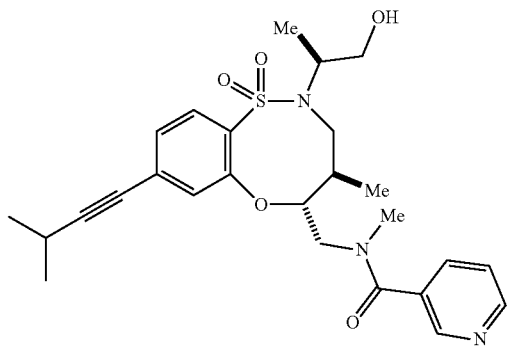 [SMILES: CC(C)C#Cc1ccc2c(c1)O[C@@H](CN(C)C(=O)c1cccnc1)[C@H](C)CN([C@@H](C)CO)S2(=O)=O]

N-(((4R,5R)-2-((S)-1-hydroxypropan-2-yl)-4-methyl-8-(3-methylbut-1-yn-1-yl)-1,1-dioxido-2,3,4,5-tetrahydrobenzo[b][1,4,5]oxathiazocin-5-yl)methyl)-N-methylnicotinamide

21

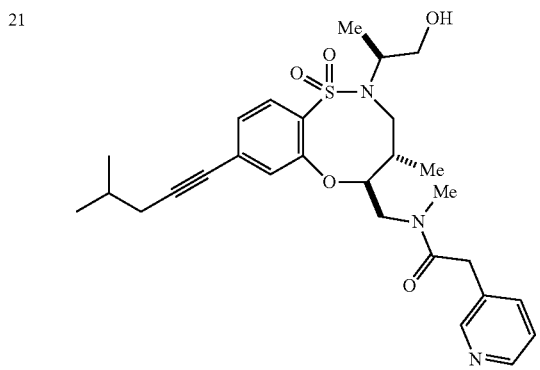

N-(((4S,5S)-2-((S)-1-hydroxypropan-2-yl)-4-methyl-8-(4-methylpent-1-yn-1-yl)-1,1-dioxido-2,3,4,5-tetrahydrobenzo[b][1,4,5]oxathiazocin-5-yl)methyl)-N-methyl-2-(pyridin-3-yl)acetamide.

11. A pharmaceutical composition comprising a pharmaceutically acceptable carrier and a compound of claim 1.

12. The compound of claim 1, wherein the compound has the Formula (IC).

13. The compound of claim 1, wherein the compound has the Formula (TB).

14. The compound of claim 12, wherein $R_3$ is

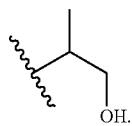

15. The compound of claim 14, wherein $R_1$ is methyl.

16. The compound of claim 13, wherein $R_3$ is

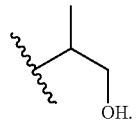 [SMILES: *C(C)CO]

17. The compound of claim 16, wherein $R_1$ is methyl.

18. The compound of claim 15, wherein $R_2$ is:

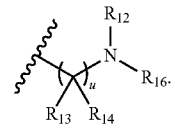

19. The compound of claim 18, wherein $R_{12}$ is $CONR_{20}R_{21}$, $C(O)R_{20}$, or $C(O)OR_{21}$.

20. The compound of claim 19, wherein $R_{16}$ is $C_1$-$C_6$ alkyl.

21. The compound of claim 1, wherein $R_{12}$ is $CONR_{20}R_{21}$, $C(O)R_{20}$, or $C(O)OR_{21}$.

22. The compound of claim 21, wherein $R_{16}$ is $C_1$-$C_6$ alkyl.

23. The compound of claim 1, wherein $R_{13}''$ is aryl or substituted aryl.

24. The compound of claim 23, wherein $R_{13}''$ is phenyl or substituted phenyl.

25. The compound of claim 17, wherein $R_2$ is:

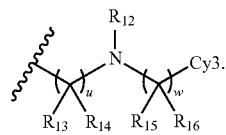

26. The compound of claim 25, wherein w is 1.

27. The compound of claim 26, wherein $R_{12}$ is $C_1$-$C_6$ alkyl or substituted $C_1$-$C_6$ alkyl.

28. The compound of claim 27, wherein Cy3 is an optionally substituted aryl or an optionally substituted heteroaryl.

29. A method of ameliorating a cell proliferative disease in a patient in need thereof comprising the step of administering a compound according to claim 1 to said patient, wherein the cell proliferative disease is selected from glioma, acute myeloid leukemia (AML), Burkitt's leukemia/lymphoma (B-ALL), melanoma, and prostate cancer.

30. The method according to claim 29, wherein said glioma is selected from astrocytomas, oligodendrogliomas, ependymomas and glioblastoma multiforme.

* * * * *

UNITED STATES PATENT AND TRADEMARK OFFICE
CERTIFICATE OF CORRECTION

PATENT NO. : 9,944,633 B2
APPLICATION NO. : 14/818009
DATED : April 17, 2018
INVENTOR(S) : Mahmud Hussain et al.

It is certified that error appears in the above-identified patent and that said Letters Patent is hereby corrected as shown below:

Column 94, Claim 1, Line 66: please delete "(TB)" and replace with --(IB)--;

Column 101, Claim 13, Line 45: please delete "(TB)" and replace with --(IB)--.

Signed and Sealed this
Seventeenth Day of July, 2018

Andrei Iancu
*Director of the United States Patent and Trademark Office*